(12) United States Patent
Duer et al.

(10) Patent No.: US 8,747,751 B2
(45) Date of Patent: Jun. 10, 2014

(54) SYSTEM AND METHOD FOR NUCLEIC ACIDS SEQUENCING BY PHASED SYNTHESIS

(75) Inventors: Reuven Duer, Thousand Oaks, CA (US); James Herron, Salt Lake City, UT (US)

(73) Assignee: PLC Diagnostics, Inc., Chatsworth, CA (US)

( * ) Notice: Subject to any disclaimer, the term of this patent is extended or adjusted under 35 U.S.C. 154(b) by 552 days.

(21) Appl. No.: 12/481,799

(22) Filed: Jun. 10, 2009

(65) Prior Publication Data
US 2009/0312188 A1 Dec. 17, 2009

(30) Foreign Application Priority Data
Jun. 16, 2008 (GB) .................................. 0811002.5

(51) Int. Cl.
*G02B 27/56* (2006.01)
*G02B 6/10* (2006.01)
*G02B 6/24* (2006.01)
*C12Q 1/68* (2006.01)
*C12N 15/10* (2006.01)

(52) U.S. Cl.
CPC *G02B 27/56* (2013.01); *G02B 6/24* (2013.01); *C12Q 1/6869* (2013.01); *C12N 15/1068* (2013.01)
USPC ... 422/82.11; 422/82.08; 435/6.1; 435/288.7; 385/12; 385/14; 385/15; 385/30; 385/50

(58) Field of Classification Search
CPC .......................... C12Q 1/6869; C12N 15/1068
USPC .......... 385/12, 14, 15, 30, 40; 435/6.1, 288.7; 422/82.08, 82.11
See application file for complete search history.

(56) References Cited

U.S. PATENT DOCUMENTS

| | | | |
|---|---|---|---|
| 4,394,060 A | 7/1983 | Verber et al. |
| 4,444,879 A | 4/1984 | Foster et al. |
| 4,478,485 A | 10/1984 | Khoe et al. |

(Continued)

FOREIGN PATENT DOCUMENTS

| | | | |
|---|---|---|---|
| EP | 598213 B1 | 7/1997 |
| EP | 0737308 B1 | 3/1998 |

(Continued)

OTHER PUBLICATIONS

Sun et al., "Synthesis of Novel Fluorinated Coumarins: Excellent UV-Light Excitable Fluorescent Dyes", 1998, Bioorganic & Medicinal Letters, 8:3107-3110.*

(Continued)

*Primary Examiner* — Christopher M Babic
*Assistant Examiner* — Jeremy C Flinders
(74) *Attorney, Agent, or Firm* — Shay Glenn LLP

(57) ABSTRACT

A system and methods of sequencing a nucleic acid by detecting the identity of a fluorescent nucleotide analogue incorporated at the 3' end of a growing nucleic acid strand are provided. The system may include a substrate comprising a plurality of substantially parallel excitation waveguides, and a plurality of substantially parallel collection waveguides, the excitation waveguides and collection waveguides crossing to form a two-dimensional array of intersection regions, a plurality of optical sensing sites in optical communication with the intersection regions, one or more switchable light sources and a detector coupled to the light dispersive module. Methods of using these systems are also described.

14 Claims, 31 Drawing Sheets

(56) References Cited

U.S. PATENT DOCUMENTS

| | | | |
|---|---|---|---|
| 4,515,430 A | 5/1985 | Johnson |
| 4,651,343 A | 3/1987 | Laor |
| 4,744,623 A | 5/1988 | Prucnal et al. |
| 4,746,179 A | 5/1988 | Dahne et al. |
| 4,799,797 A | 1/1989 | Huggins |
| 4,815,843 A | 3/1989 | Tiefenthaler et al. |
| 4,820,016 A | 4/1989 | Cohen et al. |
| 4,838,631 A | 6/1989 | Chande et al. |
| 4,850,666 A | 7/1989 | Izutsu et al. |
| 4,876,446 A | 10/1989 | Kambe et al. |
| 4,881,789 A | 11/1989 | Levinson |
| 4,889,407 A | 12/1989 | Markle et al. |
| 4,906,837 A | 3/1990 | Doneen et al. |
| 4,940,328 A | 7/1990 | Hartman |
| 4,978,503 A | 12/1990 | Shanks et al. |
| 4,998,792 A | 3/1991 | Boerstler et al. |
| 5,031,987 A | 7/1991 | Norling |
| 5,075,494 A | 12/1991 | Gassen |
| 5,077,878 A | 1/1992 | Armiento et al. |
| 5,081,012 A | 1/1992 | Flanagan et al. |
| 5,120,131 A | 6/1992 | Lukosz |
| 5,121,457 A | 6/1992 | Foley et al. |
| 5,151,480 A | 9/1992 | Podszun et al. |
| 5,173,747 A | 12/1992 | Boiarski et al. |
| 5,208,111 A | 5/1993 | Decher et al. |
| 5,217,568 A | 6/1993 | Tessier et al. |
| 5,344,784 A | 9/1994 | Attridge |
| 5,377,008 A | 12/1994 | Ridgway et al. |
| 5,439,647 A | 8/1995 | Saini |
| 5,440,388 A | 8/1995 | Erickson |
| 5,444,805 A | 8/1995 | Mayer |
| 5,455,178 A | 10/1995 | Fattinger |
| 5,479,260 A | 12/1995 | Fattinger |
| 5,494,798 A | 2/1996 | Gerdt et al. |
| 5,496,701 A | 3/1996 | Pollard-Knight |
| 5,512,492 A | 4/1996 | Herron et al. |
| 5,547,839 A | 8/1996 | Dower et al. |
| 5,573,956 A | 11/1996 | Hanning |
| 5,577,137 A | 11/1996 | Groger et al. |
| 5,581,646 A | 12/1996 | Tsukamoto et al. |
| 5,585,639 A | 12/1996 | Dorsel et al. |
| 5,600,744 A | 2/1997 | Takahashi |
| 5,614,386 A | 3/1997 | Metzker et al. |
| 5,621,031 A | 4/1997 | Leimann et al. |
| 5,623,561 A | 4/1997 | Hartman |
| 5,631,170 A | 5/1997 | Attridge |
| 5,635,608 A | 6/1997 | Haugland et al. |
| 5,640,234 A | 6/1997 | Roth et al. |
| 5,671,303 A * | 9/1997 | Shieh et al. .................. 385/12 |
| 5,677,196 A | 10/1997 | Herron et al. |
| 5,677,769 A | 10/1997 | Bendett |
| 5,710,000 A | 1/1998 | Sapolsky et al. |
| 5,712,937 A | 1/1998 | Asawa et al. |
| 5,728,529 A | 3/1998 | Metzker et al. |
| 5,734,768 A | 3/1998 | Kim et al. |
| 5,737,457 A | 4/1998 | Saini et al. |
| 5,800,992 A | 9/1998 | Fodor et al. |
| 5,814,565 A | 9/1998 | Reichert et al. |
| 5,822,472 A | 10/1998 | Danielzik et al. |
| 5,830,766 A | 11/1998 | Attridge et al. |
| 5,832,165 A | 11/1998 | Reichert et al. |
| 5,841,914 A | 11/1998 | Shieh et al. |
| 5,846,842 A | 12/1998 | Herron et al. |
| 5,861,242 A | 1/1999 | Chee et al. |
| 5,872,243 A | 2/1999 | Gee et al. |
| 5,919,712 A | 7/1999 | Herron et al. |
| 5,961,924 A | 10/1999 | Reichert et al. |
| 5,998,796 A * | 12/1999 | Liu et al. .................. 250/458.1 |
| 6,027,880 A | 2/2000 | Cronin et al. |
| 6,040,403 A | 3/2000 | Starzewski |
| 6,057,466 A | 5/2000 | Starzewski |
| 6,108,463 A | 8/2000 | Herron et al. |
| 6,110,749 A | 8/2000 | Obremski et al. |
| 6,137,117 A | 10/2000 | Feldstein et al. |
| 6,141,465 A | 10/2000 | Bischel et al. |
| 6,191,852 B1 | 2/2001 | Paffhaen et al. |
| 6,222,619 B1 | 4/2001 | Herron et al. |
| 6,228,575 B1 | 5/2001 | Gingeras et al. |
| 6,239,876 B1 | 5/2001 | Brandenberg |
| 6,242,267 B1 | 6/2001 | Herron et al. |
| 6,287,871 B1 | 9/2001 | Herron et al. |
| 6,316,274 B1 | 11/2001 | Herron et al. |
| 6,335,793 B1 | 1/2002 | Freeman et al. |
| 6,340,598 B1 | 1/2002 | Herron et al. |
| 6,350,413 B1 | 2/2002 | Reichert et al. |
| 6,361,947 B1 | 3/2002 | Dong et al. |
| 6,384,912 B2 | 5/2002 | Kraus et al. |
| 6,389,186 B1 | 5/2002 | DiGiovanni et al. |
| 6,395,558 B1 | 5/2002 | Duveneck et al. |
| 6,396,995 B1 | 5/2002 | Stuelpnagel et al. |
| 6,437,345 B1 | 8/2002 | Bruno-Raimondi et al. |
| 6,465,241 B2 | 10/2002 | Haronian et al. |
| 6,469,785 B1 | 10/2002 | Duveneck et al. |
| 6,483,096 B1 | 11/2002 | Kunz et al. |
| 6,492,468 B1 | 12/2002 | Chen et al. |
| 6,498,041 B1 | 12/2002 | Tabacco et al. |
| 6,522,408 B1 | 2/2003 | Bruck et al. |
| 6,611,634 B2 | 8/2003 | Herron et al. |
| 6,618,536 B1 | 9/2003 | Heideman et al. |
| 6,632,609 B2 | 10/2003 | Lizardi |
| 6,661,938 B2 | 12/2003 | Lim et al. |
| 6,713,264 B2 | 3/2004 | Luttermann et al. |
| 6,759,663 B2 | 7/2004 | Tsipouras et al. |
| 6,777,244 B2 | 8/2004 | Pepper et al. |
| 6,785,432 B2 | 8/2004 | Letant et al. |
| 6,801,677 B1 | 10/2004 | Grace et al. |
| 6,830,936 B2 | 12/2004 | Anderson et al. |
| 6,847,746 B2 | 1/2005 | Uchiyama |
| 6,911,344 B1 | 6/2005 | Reichert et al. |
| 6,947,634 B2 | 9/2005 | Tanaka et al. |
| 6,951,715 B2 | 10/2005 | Cunningham et al. |
| 6,956,651 B2 | 10/2005 | Lackritz et al. |
| 6,961,490 B2 | 11/2005 | Maisenhoelder et al. |
| 6,974,673 B2 | 12/2005 | Lockhart |
| 6,979,567 B2 | 12/2005 | Herron et al. |
| 6,987,898 B2 | 1/2006 | Tran et al. |
| 7,046,893 B2 | 5/2006 | Dorn et al. |
| 7,057,031 B2 | 6/2006 | Olejnik et al. |
| 7,058,255 B2 | 6/2006 | Fang |
| 7,101,945 B2 | 9/2006 | Dorn et al. |
| 7,122,012 B2 | 10/2006 | Bouton et al. |
| 7,175,811 B2 | 2/2007 | Bach et al. |
| 7,203,386 B2 | 4/2007 | Krol et al. |
| 7,227,147 B2 | 6/2007 | Riehle et al. |
| 7,248,771 B2 * | 7/2007 | Schmidt et al. .................. 385/129 |
| RE39,772 E | 8/2007 | Herron et al. |
| 7,292,336 B2 | 11/2007 | Cunningham et al. |
| 7,308,166 B1 | 12/2007 | Peng et al. |
| 7,349,080 B2 | 3/2008 | Aklian |
| 7,358,079 B2 | 4/2008 | Schürmann-Mader et al. |
| 7,373,063 B2 | 5/2008 | Nakata et al. |
| 7,396,675 B2 | 7/2008 | Pawlak et al. |
| 7,410,784 B2 | 8/2008 | Hatch |
| 7,444,053 B2 | 10/2008 | Schmidt et al. |
| 7,447,391 B2 | 11/2008 | Peled et al. |
| 7,483,140 B1 | 1/2009 | Cho et al. |
| 7,545,494 B2 | 6/2009 | Haiml et al. |
| 7,627,201 B2 | 12/2009 | Tiefenthaler |
| 7,708,945 B1 | 5/2010 | Abel et al. |
| 7,811,754 B2 | 10/2010 | Herron et al. |
| 7,820,983 B2 * | 10/2010 | Lundquist et al. .......... 250/458.1 |
| 7,838,847 B2 | 11/2010 | Lundquist et al. |
| 7,879,598 B2 | 2/2011 | Zesch et al. |
| 7,922,976 B2 | 4/2011 | Dutta et al. |
| 8,187,866 B2 | 5/2012 | Duer |
| 2001/0001021 A1 | 5/2001 | Kraus et al. |
| 2001/0055462 A1 | 12/2001 | Seibel |
| 2002/0045811 A1 | 4/2002 | Kittrell et al. |
| 2002/0097947 A1 | 7/2002 | Lim et al. |
| 2002/0114576 A1 | 8/2002 | Schroeder |
| 2002/0126936 A1 | 9/2002 | Lockhart |
| 2002/0126938 A1 | 9/2002 | Lockhart |
| 2002/0172457 A1 | 11/2002 | Tapalian et al. |
| 2002/0191884 A1 | 12/2002 | Letant et al. |

(56) References Cited

U.S. PATENT DOCUMENTS

| | | |
|---|---|---|
| 2002/0197456 A1 | 12/2002 | Pope |
| 2003/0059853 A1 | 3/2003 | Lockhart |
| 2003/0063851 A1 | 4/2003 | Hillendahl et al. |
| 2003/0091277 A1 | 5/2003 | Mei |
| 2003/0108274 A1 | 6/2003 | Haronian |
| 2003/0108291 A1 | 6/2003 | Duveneck et al. |
| 2003/0138208 A1 | 7/2003 | Pawlak et al. |
| 2003/0169956 A1 | 9/2003 | Lange et al. |
| 2004/0008919 A1 | 1/2004 | Freeman et al. |
| 2004/0020987 A1 | 2/2004 | Nishioka et al. |
| 2004/0022475 A1 | 2/2004 | Pennington |
| 2004/0023396 A1 | 2/2004 | Boyd et al. |
| 2004/0036949 A1 | 2/2004 | Trezza |
| 2004/0046128 A1 | 3/2004 | Abel et al. |
| 2004/0052489 A1 | 3/2004 | Duveneck et al. |
| 2004/0081384 A1 | 4/2004 | Datesman et al. |
| 2004/0105644 A1* | 6/2004 | Dawes ..................... 385/129 |
| 2004/0142370 A1 | 7/2004 | Dosmann et al. |
| 2004/0197044 A1 | 10/2004 | Bloom |
| 2005/0018949 A1 | 1/2005 | Yan |
| 2005/0043139 A1 | 2/2005 | Kennedy |
| 2005/0078903 A1 | 4/2005 | Grace et al. |
| 2005/0088648 A1 | 4/2005 | Grace et al. |
| 2005/0089261 A1 | 4/2005 | Shimazaki |
| 2005/0110989 A1 | 5/2005 | Schermer |
| 2005/0145783 A1 | 7/2005 | Zheng |
| 2005/0153320 A1 | 7/2005 | Herron et al. |
| 2005/0163659 A1 | 7/2005 | Duveneck et al. |
| 2005/0195394 A1 | 9/2005 | Ma et al. |
| 2005/0196102 A1 | 9/2005 | Yamazaki et al. |
| 2005/0201657 A1 | 9/2005 | Tiefenthaler |
| 2005/0201659 A1 | 9/2005 | Strecker |
| 2005/0227231 A1 | 10/2005 | Tcherkassov |
| 2005/0254744 A1 | 11/2005 | Freeman |
| 2006/0008227 A1 | 1/2006 | Schmidt et al. |
| 2006/0014151 A1 | 1/2006 | Ogura et al. |
| 2006/0061754 A1 | 3/2006 | Turner et al. |
| 2006/0072873 A1 | 4/2006 | Tekippe et al. |
| 2006/0073491 A1 | 4/2006 | Joseph et al. |
| 2006/0078889 A1 | 4/2006 | Bhattacharjee et al. |
| 2006/0098927 A1 | 5/2006 | Schmidt et al. |
| 2006/0115230 A1 | 6/2006 | Komoguchi et al. |
| 2006/0183145 A1* | 8/2006 | Turner ..................... 435/6 |
| 2007/0077595 A1 | 4/2007 | Koo et al. |
| 2007/0211985 A1 | 9/2007 | Duer |
| 2007/0222704 A1 | 9/2007 | Huang |
| 2007/0231458 A1 | 10/2007 | Gale |
| 2007/0231880 A1 | 10/2007 | Chang-Yen |
| 2008/0117418 A1 | 5/2008 | Claps et al. |
| 2008/0243181 A1 | 10/2008 | Schneider et al. |
| 2009/0068668 A1 | 3/2009 | Duer |
| 2010/0072396 A1 | 3/2010 | Agranat et al. |
| 2010/0167413 A1 | 7/2010 | Lundquist et al. |
| 2010/0202925 A1 | 8/2010 | Sonnleitner |
| 2010/0248352 A1 | 9/2010 | Song et al. |
| 2010/0256016 A1 | 10/2010 | Blair et al. |
| 2010/0279429 A1 | 11/2010 | Hildenbrand et al. |
| 2010/0302544 A1 | 12/2010 | Duer |
| 2012/0231532 A1 | 9/2012 | Duer |

FOREIGN PATENT DOCUMENTS

| | | | |
|---|---|---|---|
| EP | 517516 | B1 | 12/1999 |
| EP | 671626 | B1 | 1/2000 |
| EP | 918984 | B1 | 6/2001 |
| EP | 901620 | B1 | 1/2002 |
| EP | 0783683 | B1 | 4/2004 |
| EP | 1413876 | A2 | 4/2004 |
| EP | 901623 | B1 | 6/2004 |
| EP | 1441217 | A2 | 7/2004 |
| EP | 1413876 | A3 | 2/2005 |
| EP | 1441217 | A3 | 7/2007 |
| EP | 1315968 | B1 | 2/2008 |
| EP | 1635177 | B1 | 7/2008 |
| EP | 2144947 | B1 | 3/2011 |
| EP | 1356291 | B1 | 5/2011 |
| GB | 2377492 | A | 1/2003 |
| JP | 2008-513782 | A | 5/2008 |
| WO | WO 92/21768 | A1 | 12/1992 |
| WO | WO 94/18544 | A1 | 8/1994 |
| WO | WO 94/27137 | A2 | 11/1994 |
| WO | WO 94/28395 | A1 | 12/1994 |
| WO | WO 95/14225 | A1 | 5/1995 |
| WO | WO 95/33197 | A1 | 12/1995 |
| WO | WO 95/33198 | A1 | 12/1995 |
| WO | WO 96/26432 | A1 | 8/1996 |
| WO | WO97/35176 | A1 | 9/1997 |
| WO | WO 97/35181 | A1 | 9/1997 |
| WO | WO 97/35203 | A1 | 9/1997 |
| WO | WO 97/39370 | A1 | 10/1997 |
| WO | WO 99/14594 | A1 | 3/1999 |
| WO | WO 99/45354 | A2 | 9/1999 |
| WO | WO 99/45354 | A3 | 10/1999 |
| WO | WO 00/75644 | A1 | 12/2000 |
| WO | WO01/55691 | A2 | 8/2001 |
| WO | WO02/37148 | A2 | 5/2002 |
| WO | WO02/40998 | A2 | 5/2002 |
| WO | WO02/46756 | A1 | 6/2002 |
| WO | WO 02/066983 | A2 | 8/2002 |
| WO | WO 03/006625 | A2 | 1/2003 |
| WO | WO 2004/020987 | A1 | 2/2003 |
| WO | WO03/021253 | A2 | 3/2003 |
| WO | WO 02/066983 | A3 | 5/2003 |
| WO | WO 03/062791 | A2 | 7/2003 |
| WO | WO2004/023142 | A2 | 3/2004 |
| WO | WO2004/023143 | A2 | 3/2004 |
| WO | WO 03/062791 | A3 | 6/2004 |
| WO | WO 2005/043139 | A1 | 5/2005 |
| WO | WO 2005/084367 | A2 | 9/2005 |
| WO | WO 2006/135782 | A2 | 12/2006 |
| WO | WO 2007/070869 | A2 | 6/2007 |
| WO | WO 2007/094817 | A2 | 8/2007 |
| WO | WO 2007/123763 | A2 | 11/2007 |
| WO | WO 2008/069973 | A2 | 6/2008 |

OTHER PUBLICATIONS

Levene et al., Science, 2003, 299:682-686.*
Webpage snapshot from Prof Prieve, 2012.*
Ausubel, et al. (Eds.) Current Protocols in Molecular Biology, vols. I, II, and III, (1997).
Ausubel, et al. (Eds.), Short Protocols in Molecular Biology: A Compendium of Methods from Current Protocols in Molecular Biology, 5th Ed., John Wiley & Sons, Inc. (2002).
Batzer, et al. Enhanced evolutionary PCR using oligonucleotides with inosine at the 3'-terminus Nucleic Acid Res. 1991; 19:5081.
Bieche, et al. Quantitation of MYC gene expression in sporadic breast tumors with a real-time reverse transcription-PCR assay. Cancer Res. Jun. 15, 1999;59(12):2759-65.
Chee, et al. Accessing genetic information with high density DNA arrays. Science. 1996; 274:610-614.
Herron, et al. Orientation and Activity of Immobilized Antibodies. In: Biopolymers at Interfaces, 2nd Edition (M. Malmsten, ed.). Surfactant Science Series. Marcel Dekker, New York. 2003; 110:115-163.
Herron, et al. Planar waveguide biosensors for point-of-care clinical and molecular diagnostics. In: Fluorescence Sensors and Biosensors. R. B. Thompson, Ed. CRC Press Taylor & Francis Group. Boca Raton, FL. 2005: 283-332.
Innis, et al. (Eds.) PCR Protocols: A Guide to Methods and Applications, Elsevier Science & Technology Books (1990).
Kreuzer, et al. LightCycler technology for the quantitation of bcr/abl fusion transcripts. Cancer Research. 1999; 59(13):3171-4.
Laurendeau, et al. Quantitation of MYC gene expression in sporadic breast tumors with a real-time reverse transcription-PCR assay. Clin Chem. 1999; 59(12):2759-65.
Laurendeau, et al. TaqMan PCR-based gene dosage assay for predictive testing in individuals from a cancer family with INK4 locus haploinsufficiency. Clin Chem. 1999; 45(7):982-6.

(56) References Cited

OTHER PUBLICATIONS

Ohtsuka, et al. An alternative approach to deoxyoligonucleotides as hybridization probes by insertion of deoxyinosine at ambiguous codon positions. J. Biol. Chem. 1985; 260:2605-2608.

Rossolini, et al. Use of deoxyinosine-containing primers vs degenerate primers for polymerase chain reaction based on ambiguous sequence information. Mol. Cell. Probes. 1994; 8:91-98.

Saizieu, et al. Bacterial transcript imaging by hybridization of total RNA to oligonucleotide arrays. Nat Biotechnol. 1998; 16(1):45-8.

Sambrook, et al., Molecular Cloning: A Laboratory Manual, 3rd Ed., Cold Spring Harbor Laboratory Press (2000).

Burgess et al.; A New Photolabile Protecting Group for Nucleotides; Abstracts of Papers Part 2.; 211th ACS National Meeting, American Chemical Society; New Orleans, LA; Mar. 24-28, 1996.

Hutchison, Clyde A.; DNA sequencing: bench to bedside and beyond; Nucleic Acid Res.; vol. 35; No. 18; pp. 6227-6237; Sep. 2007.

Kaplan et al.;Rapid photolytic release of adenosine 5'-triphosphate from a protected analog: utilization by the sodium:potassium pump of human red blood ghost cells; Biochemistry; vol. 17; pp. 1929-1935; May 1978.

Kulagina et al.; Antimicrobial peptides as new recognition molecules for screening challenging species; (Author Manuscript) Sens. Actuators B. chem.; vol. 121 (1); pp. 150-157; Jan. 2007.

Lockhart et al.; Expression monitoring by hybridization to high-density oligonucleotide arrays; Nature Biotechnology; vol. 14; pp. 1675-1680; Dec. 1996.

McCray et al.; A new approach to time-resolved studies of ATP-requiring biological systems; laser flash photolysis of caged ATP; Proc. Natl. Acad. Sci. USA; vol. 77; No. 12; pp. 7237-7241; Dec. 1980.

Metzker et al.; Termination of DNA synthesis by novel 3'-modified-deoxyribonucleoside 5'-triphosphates; Nucleic Acids Res.; vol. 22; No. 20; pp. 4259-4267; Oct. 1994.

Pillai, Rajasekharan V.N.; V.N.; Photoremovable Protecting Groups in Organic Synthesis ; Synthesis; 1980(1); pp. 1-26; Jan. 1980.

Plowman et al.; Femtomolar Sensitivity using a channel-etched Thin Film Waveguide Fluoroimmunosensor; Biosensors & Bioelectronics; vol. 11(1-2); pp. 149-160; Jan. 1996.

Xu et al.; Protein and chemical microarrays—powerful tools for proteomics; J Biomed Biotechnol; vol. 2003(5); pp. 257-266; Dec. 2003.

Zehavi et al.; J. Light-sensitive glycosides. I. 6-nytroveratryl .beta.-D-glucopyranoside and 2-nitrobenzyl beta.-D-glucopyranoside; J. Organic Chem.; vol. 37(14); pp. 2281-2285; Jul. 1972.

Zourob et al.; Principles of bacterial detection: Biosensors, Recognition Receptors and microsystems; Eds., Springer Science and Business Media, NY; pp. 178-180; Jun. 2008.

* cited by examiner

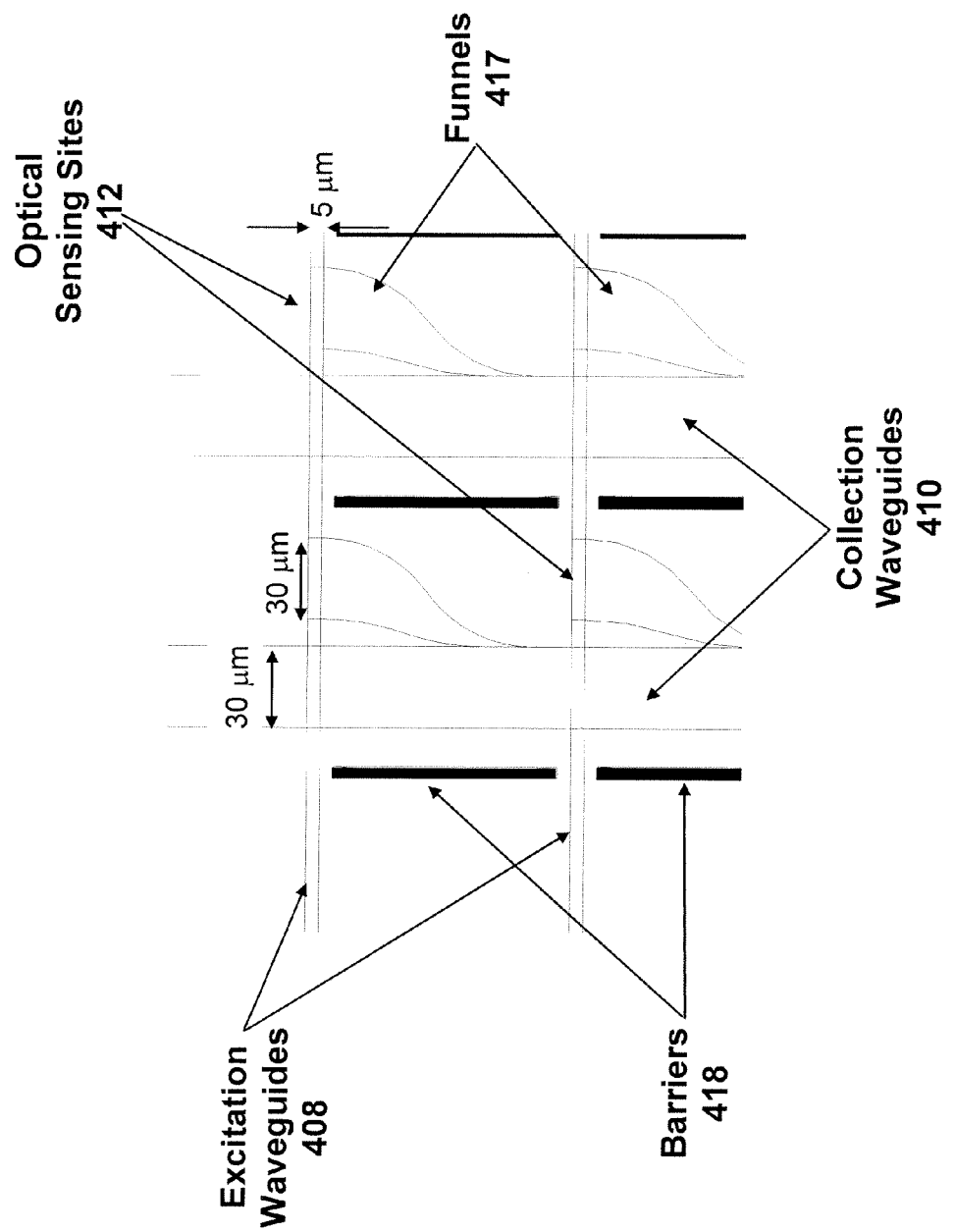

SYSTEM AND METHOD FOR NUCLEIC ACIDS SEQUENCING BY PHASED SYNTHESIS

CROSS-REFERENCE TO RELATED APPLICATIONS

This application claims priority to United Kingdom Patent Application No. 0811002.5, filed on Jun. 16, 2008, now issued as United Kingdom Patent No. 2461026, all of which is fully incorporated herein by reference.

BACKGROUND OF THE INVENTION

The completion of the 'Human Genome' project in 2003 which revealed the sequence of all 3 billion bases of the human DNA has enabled a large number of applications in medical diagnostics, prognostics, therapeutics and more. Many of these rely on re-sequencing part or all of the genome of individuals, creating a need for reliable, fast and affordable DNA sequencing technologies.

In an effort to address this need, several different technologies had been developed in the last few years and new generations of sequencing systems have emerged. All of these new systems are grouped under the Next Generation Sequencing title to distinguish them from the first generation technologies used until and within the 'Human Genome' project (1990-2003).

The most advanced of these Next Generation Sequencing approaches employ solid surfaces (e.g., chips, beads, nanopores etc.) for sequencing reactions. Such surfaces enable lower reagent volume, higher multiplexing, higher accuracy and repeatability and simpler protocols, all of which are critical for meeting the stringent requirements of Next Generation Sequencing.

There remains a pressing need for improved systems for Next Generation Sequencing. An ideal system would provide increased sensitivity, eliminate or reduce washing steps and simplify integration with microfluidic technologies. The present invention satisfies this need and provides related advantages.

SUMMARY OF THE INVENTION

In general, in one aspect a scanning sensor system for sequencing a nucleic acid is provided. The system includes a substrate (e.g., as illustrated in FIG. 1) that includes a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection region at each crossing; a plurality of optical sensing sites arranged in optical communication with the intersection regions; one or more switchable light sources coupled to and in optical communication with the excitation waveguides of the substrate, and including a scanning light source input and a photo-cleaving light source input; a light dispersive module coupled to and in optical communication with the collection waveguides of the substrate, and including an array of elements; a detector coupled to and in optical communication with the light dispersive module.

In one embodiment the scanning light source is coupled to a first switchable light source coupled to and in optical communication with the excitation waveguides at a first side of the substrate and a photo-cleaving light source coupled to a second switchable light source coupled to and in optical communication with the excitation waveguides at a second side of the substrate.

In general, in a further aspect a scanning sensor system for sequencing a nucleic acid includes a substrate including a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection region at each crossing; a plurality of optical sensing sites arranged in optical communication with the intersection regions; a switchable light source in optical communication with the excitation waveguides, and including a scanning light source input; a photo-cleaving light source and light delivery system arranged external to the substrate (e.g., as illustrated in FIG. 2C); a light dispersive module coupled to and in optical communication with the collection waveguides of the substrate, and comprising an array of elements; a detector coupled to and in optical communication with the light dispersive module.

The light delivery system can include a photo-cleaving light source input.

The dispersive module can be configured to disperse light from one or more of the collection waveguides to a plurality of elements in the detector. In one embodiment the dispersive module is configured to disperse light from a given collection waveguide to four or more elements in the detector. In a particular embodiment the dispersive module disperses light to four elements in the detector. In a different embodiment, the dispersive module disperses light five or more elements in the detector.

Light dispersed from the dispersive module can include a plurality of light wavelengths. In one embodiment the plurality of wavelengths includes four or more light wavelengths. In another embodiment the plurality of wavelengths includes five or more wavelengths.

The photo-cleaving light source can emit light having a wavelength ranging between 400 nm and 2000 nm. The photo-cleaving light source input can be coupled to an ultra-violet light source. In one embodiment the ultra-violet light source emits light having a wavelength ranging between 100 nm and 400 nm.

In general, in one aspect a method of sequencing a nucleic acid by detecting the identity of a fluorescent nucleotide analogue incorporated at the 3' end of a growing nucleic acid strand is provided. The method includes the steps of (a) immobilizing a plurality of complexes comprising a template nucleic acid, a primer configured to hybridize to the template and a polymerase, at a plurality of optical sensing sites of a substrate, wherein the substrate is part of a waveguide-based optical scanning system; (b) extending the primer by a single nucleotide with the polymerase and one or more fluorescent nucleotide analogues using a polymerase extension reaction, wherein each type of fluorescent nucleotide analogue includes a unique fluorescent tag optionally configured to inhibit further primer extension and/or a blocking agent at the 3' end and wherein incorporation of the fluorescent nucleotide analogue reversibly terminates the polymerase extension reaction; (c) detecting the unique tag of the fluorescent nucleotide analogue by optically scanning the substrate using the optical scanning system to identify the fluorescent nucleotide analogue incorporated by the polymerase reaction; (d) recording the results of the optical scanning of the substrate; (e) reversing the termination of the polymerase extension reaction by providing a photo-cleaving pulse of light to one or more of the optical sensing sites of the substrate to cleave the fluorescent tag or the blocking agent; and (f) repeating steps (b) through (e).

The primer in one embodiment is immobilized at the plurality of optical sensing sites prior to formation and immobilization of the plurality of complexes. In a particular embodiment the primers are covalently immobilized at the optical sensing sites. In another embodiment the primers are immobilized using a photo-cleavable linker at the optical sensing sites.

The polymerase in one embodiment is immobilized at the plurality of optical sensing sites prior to formation and immobilization of the plurality of complexes. In a specific embodiment the polymerases are covalently immobilized at the optical sensing sites prior to immobilizing the plurality of complexes.

In one embodiment of the method step (b) is performed before step (c) without a washing step between steps (b) and (c). In another embodiment of the method step (f) further includes performing step (e) before repeating step (b) without a washing step between steps (e) and (b).

The nucleic acid being sequenced can be DNA.

In one embodiment the primers are immobilized using a photo-cleavable linker at the optical sensing sites and the polymerases are covalently immobilized at the optical sensing sites prior to formation and immobilization of the plurality of complexes. In a related embodiment prior to step (b) immobilized primer and template duplexes are formed, and a photo-cleaving pulse of light is provided to cleave the photo-cleavable linker and release the duplexes, wherein the released duplexes subsequently bind to the immobilized polymerases and form the immobilized plurality of complexes.

The fluorescent nucleotide analogs can include four different dNTPs, wherein each dNTP is labeled with a different fluorescent tag. In a particular embodiment the fluorescent tags are attached to the dNTPs through a photo-cleavable chemical bond.

In general, in another aspect a method of sequencing a single nucleic acid molecule by detecting the identity of a fluorescent nucleotide analogue after the nucleotide analogue is incorporated into a growing nucleic acid strand is provided. The method includes the steps of (a) immobilizing a complex comprising a template nucleic acid, a primer configured to hybridize to the template and a polymerase, at an optical sensing sites of a substrate, wherein the substrate is part of a waveguide-based optical scanning system; (b) extending the primer by a single nucleotide with the polymerase and one or more fluorescent nucleotide analogues using a polymerase extension reaction, wherein each fluorescent nucleotide analogue comprises a fluorescent tag optionally configured to inhibit further primer extension and/or a blocking agent at the 3' end of the nucleotide analog and wherein incorporation of the fluorescent nucleotide analogue terminates the polymerase extension reaction; (c) detecting the unique label attached to the fluorescent nucleotide analogue by optically scanning the substrate using the optical scanning system to identify the fluorescent nucleotide analogue incorporated by the polymerase reaction; (d) recording the results of the optical scanning of the substrate; (e) providing a photo-cleaving pulse of light to one or more of the optical sensing sites of the substrate to cleave the fluorescent tag and/or the blocking agent; and (f) repeating steps (b) through (e).

The primer can be immobilized at the plurality of optical sensing sites prior to formation and immobilization of the complex. In a particular embodiment the primer is covalently immobilized at the optical sensing sites. In another embodiment the primer is immobilized using a photo-cleavable linker at the optical sensing sites.

The polymerase can be immobilized at the plurality of optical sensing sites prior to formation and immobilization of the complex. In one embodiment the polymerase is covalently immobilized at the optical sensing sites prior to immobilizing the complex.

In one embodiment of the method step (b) is performed before step (c) without a washing step between steps (b) and (c). In another embodiment of the method step (f) further includes performing step (e) before repeating step (b) without a washing step between steps (e) and (b).

The nucleic acid being sequenced can be DNA.

In a particular embodiment of the method the primer is immobilized using a photo-cleavable linker at the optical sensing sites and polymerase is covalently immobilized at the optical sensing sites prior to formation and immobilization of the complex. In one embodiment prior to step (b) immobilized primer and template duplexes are formed, and a photo-cleaving pulse of light is provided to cleave the photo-cleavable linker and release the duplexes, wherein the released duplexes subsequently bind to the immobilized polymerase and form the immobilized complex.

The fluorescent nucleotide analogs can include four different dNTPs, wherein each is labeled with a different fluorescent tag. In one embodiment the fluorescent tags are attached to the dNTPs through a photo-cleavable chemical bond.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4B is a schematic showing an enlarged view of substrate features according to one embodiment.

DETAILED DESCRIPTION OF THE INVENTION

Figure 1:
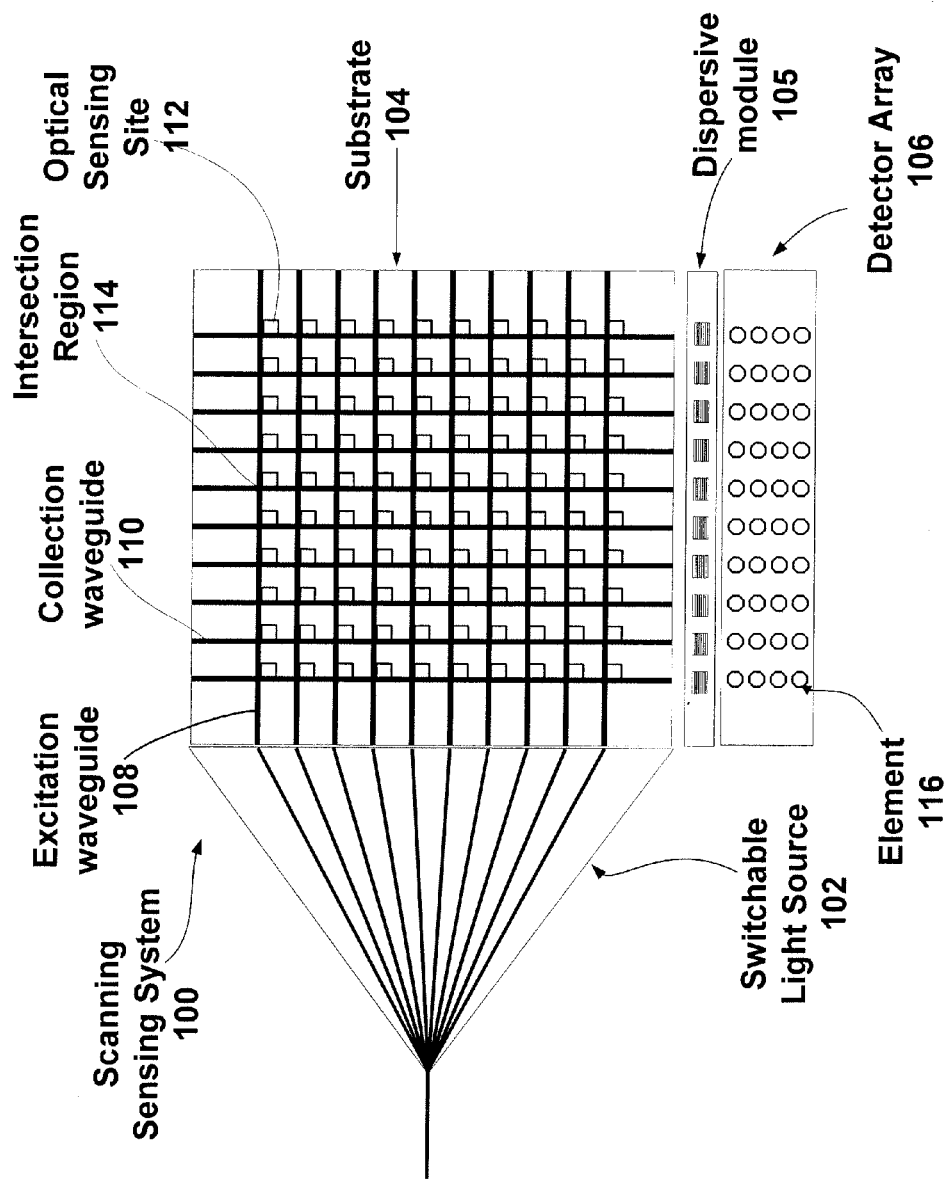
FIG. 1 is a schematic of the scanning sensing system according to one embodiment of the invention including a switchable light source, a substrate, optical sensing sites, a dispersive module and a detector array.

The present invention provides a novel approach for sequencing nucleic acids (DNA, RNA etc.), in which solid phase sequencing reactions are performed on the surface of a microarray chip containing embedded waveguides able to direct light to and from the reaction sites. One advantage of the waveguide-based sensing is the surface selectivity inherent to the technology. Sensing of only the reactions occurring within tens of nanometers off the waveguide's boundary while avoiding the bulk, significantly reduces the detection noise and enables fewer or no washing steps. The present invention also simplifies integration with microfluidic delivery technologies which can use the upper surface of the chip without interfering with the interrogation system.

Nucleic acids can be deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

Herein polymorphism is the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism (SNP) occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Herein an individual is not limited to a human being, but may also include other organisms including but not limited to mammals, plants, bacteria or cells derived from any of the above.

Aspects of the invention may include one or more of the following advantageous features. Dense and accurate integration of optical manipulating elements can be achieved using planar lightwave circuits technology. Applications for planar lightwave circuits as described herein include useful for nucleic acid sequence analysis for applications including but not limited to disease research, biomarkers discovery, SNP association studies including toxicology and disease susceptibility, and diagnostics including identifying patients predisposed to diseases and identifying patients with particular drug sensitivity.

Optical Scanning System

The optical scanning sensing systems disclosed herein relate to those described in U.S. patent application Ser. No. 11/683,808 filed Mar. 8, 2007, now U.S. Pat. No. 7,951,583, and 60/971,878 filed Sep. 12, 2007. A block diagram of one embodiment of the optical scanning system is depicted in FIG. 1.

In one embodiment, as shown in FIG. 1, a switchable light source 102 is coupled to and is in optical communication with one or more of the excitation waveguides 108 at a first edge of a substrate 104. Additionally, a dispersive module 105 and a detector array 106 are coupled to and in optical communication with one or more collection waveguide 110 at a second edge of substrate 104. Although a single detector at one edge of the substrate is shown, it is envisioned that two or more detectors could be coupled to and in optical communication with one or more collection waveguide at various edges of the substrate (not shown). For example, in one embodiment, where the switchable light source is coupled to a first edge of the substrate, a first detector could be coupled to an adjacent edge and be in optical communication with a first end of a collection waveguide, while a second detector could be coupled to another adjacent edge and be in optical communication with a second end of a collection waveguide (not shown). A third detector can be coupled to the edge opposite to the one coupled to the switchable light source and in optical communication with the second end of the excitation waveguides (not shown).

Substrate 104 can include intersection regions 114 where collection waveguides 110 and excitation waveguides 108 cross or intersect.

As shown in FIG. 1, in one embodiment the system 100 can be substantially planar. For example, the switchable light source 102 can be a planar chip. This can be coupled to a planar substrate 104 that is a second chip, that is further coupled to a planar dispersion module 105 that is a third chip and further coupled to detector array 106 that is part of the same or a fourth chip. In a particular embodiment, as shown in FIG. 1, the system 100 is a planar lightwave circuit including four coupled chips. In one embodiment two chips are integrated into a single chip (e.g., an optical switch chip and substrate chip). Such a configuration would be useful in a case where the substrate chip is reusable and can be effectively used for long periods of time. In addition, having two chips integrated on a single substrate solves the problem of maintaining the relative alignment of two chips (e.g., a switchable light source chip and substrate chip).

In the embodiment of FIG. 1, it is envisioned that crossing or intersecting of the excitation waveguides and the collection waveguides can be a direct physical crossing or intersecting, for example, where the excitation waveguides and the collection waveguides are embedded within the substrate in a single or multiple layers. Alternatively, it is envisioned that the crossing or intersecting involves a physical space or distance between the excitation waveguides and the collection waveguides, for example, where the excitation waveguides and the collection waveguides are embedded within the substrate in separate layers. As shown in FIG. 1, the optical sensing sites 112 of the system 100 typically are associated with the intersection regions 114. Typically one optical sensing site 112 is associated with each intersection region 114. As illustrated, in one embodiment the number of intersection regions 114 and optical sensing sites 112 is an arrangement of 100 intersection regions 114 and 100 optical sensing sites 112. It is envisioned that the number of intersection regions and optical sensing regions on a substrate chip can be greater than 10, greater than 100, greater than 1,000, greater than 10,000, greater than 100,000 or greater than 1,000,000. It is further envisioned that the density of intersection regions can be greater than 10 per $cm^2$, greater than 100 per $cm^2$, greater than 1,000 per $cm^2$ greater than 10,000 per $cm^2$, greater than 100,000 per $cm^2$ or greater than 1,000,000 per $cm^2$. In one embodiment the density of intersection regions is greater than 2,000 per $cm^2$.

As further shown in FIG. 1, the crossing or intersecting of the excitation waveguides 108 and the collection waveguides 110 can be substantially perpendicular, for example, at an angle of 90°. Alternatively, in certain embodiments the crossing or intersecting can be angled less than or great than 90°.

It is also envisioned that in the embodiment of FIG. 1, a first light wave generated by the switchable light source in an excitation waveguide induces the sensor to transduce an optical signal resulting in a second light wave in a collection waveguide, the second light wave being detectable by the detector.

As illustrated in FIG. 1, in one advantageous embodiment, the system 100 is a planar two-dimensional scanning system. The system 100 in this embodiment includes a planar switchable light source 102, for example, a planar optical switch or an array of switchable lasers. Furthermore, the switchable light source 102 can provide a dynamic source of light for selective and programmed excitation in respect to individual excitation waveguides 108, providing excitation to all of the optical sensing sites 112 along that excitation waveguide 108. A dynamic light source includes but is not limited to a tunable wavelength and/or tunable bandwidth light source. Additionally, the system 100 of this embodiment provides for planar collection of the emitted light from all the excited sensing sites 112 in the collection waveguides 110, specifically in the plane of the substrate 104, such that the light collection is substantially perpendicular to the direction of the light produced in the excitation waveguides 108.

As shown in FIG. 1, dispersive module 105 can be arranged in optical communication with substrate 104, including, for example, collection waveguides 110. Dispersive module 105 serves to separate different wavelengths present in the light exiting collection waveguides 110 and can be configured to direct each wavelength out of a given excitation waveguide 110 to a separate detector element 116 in the 1D or 2D detector array 106. It is envisioned that where multiple wavelengths are guided through the dispersive module (e.g., four or more colors of light) the module can be arranged such that different wavelengths are provided vertically to a detector array through the module. In this case, the detector array can be a two-dimensional detector array including multiple elements arranged to receive the vertically dispersed light. In an alternative embodiment, the dispersive element can be arranged to provide multiple wavelengths of light horizontally dispersed to a series of detector array elements arranged horizontally to receive the dispersed light from the dispersive module. In this case the detector array can be a one-dimensional detector array. Although dispersive module 105 is shown in FIG. 1 as a separated module, it is anticipated that in a specific embodiment dispersive module 105 can be integrated into a single module with the detector array 106. By way of non-limiting example, the dispersive module 105 can include dispersive gratings of any kind including but not limited to holographic, mechanically ruled, computer generated or UV written gratings as well as prisms, slits and any other kind of dispersive structure known in the field.

It is envisioned that the dispersive module can be configured to separate light exiting collection waveguides into a plurality of different wavelengths. In one exemplary embodiment the light is separated into four different wavelengths, useful, for example, in four color nucleic acid sequencing. In another embodiment, more than four different wavelengths can be separated. For example five or more wavelengths can be separated. In a four color sequencing application additional separated wavelengths (beyond four) can be useful, for example, to aid in calibration and normalization.

Detector array 106 as shown in FIG. 1 can include an array of elements 116. It is envisioned that any number of elements can be optically aligned with dispersive module 105 to receive light of a desired wavelength. In one embodiment as illustrated in FIG. 1, a set of four elements can be aligned with dispersive module 105 such that four different wavelengths of light (e.g., from four different fluorescent dyes) can be detected from a given collection waveguide 110 that results from sequencing-related dye activity at an optical sensing site 112. As discussed for dispersive module 105, five or more wavelengths of light can be employed and as such five or more elements 116 per collection waveguide 110 are envisioned. As such, elements 116 of detector array 106 can be arranged in a variety of useful configurations, for example, four by ten, five by ten, or six by ten. Although a series of ten elements 116 are shown, it is envisioned that any number of elements can be useful including but not limited to ten or more, twenty or more, one hundred or more or even one thousand or more.

It is also envisioned that dispersive module can disperse the different wavelengths emerging from a single collection waveguide horizontally mapping them into different detector elements of a one-dimensional detector array (not shown).

Alternative embodiments of the optical scanning system are disclosed in U.S. patent application Ser. No. 11/683,808 filed Mar. 8, 2007, now U.S. Pat. No. 7,951,583, and 60/971,878 filed Sep. 12, 2007.

A second part of the optical system of the current invention is an optical or photo-cleaving system. The photo-cleaving system includes a light source and optical means to deliver the emitted light to one or more of the optical sensing sites.

In one specific embodiment the light source of the photo-cleaving system emits light with wavelength in the UV (Ultra-Violet) spectral range. In particular non-limiting embodiment, the light source emits UV light with wavelength between 100 nm to 400 nm. In yet another embodiment the wavelength emitted is in the visible or in the Infra-Red spectral range between 400 nm and 2000 nm.

A number of possible embodiments are envisioned for delivering the light from the photo-cleaving light source to the sensing sites 212.

Figure 2A:
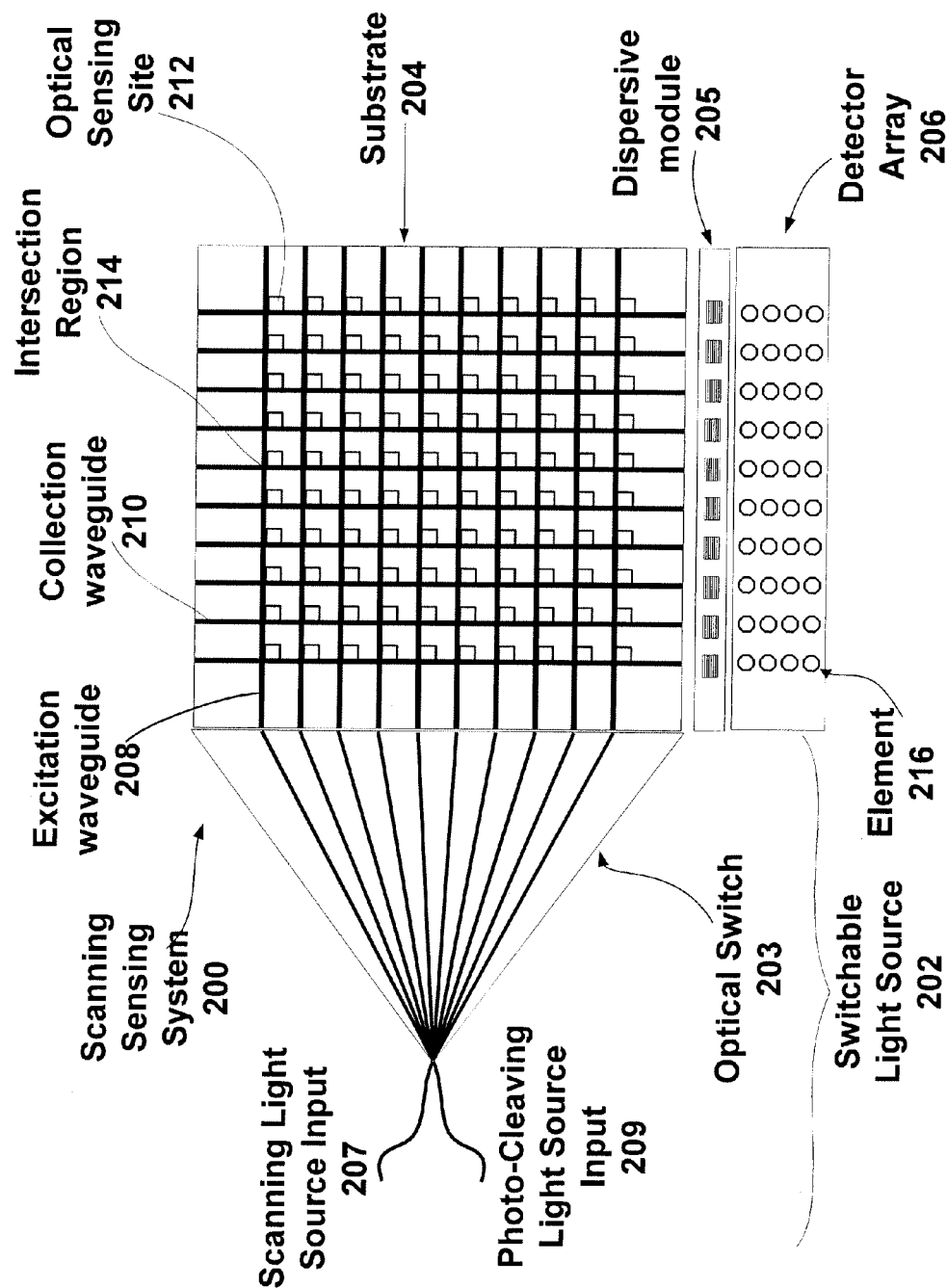
FIG. 2A is a schematic of the scanning sensing system according to another embodiment of the invention including a switchable light source, a substrate, optical sensing sites, a dispersive module and a detector array, wherein the switchable light source includes an optical switch, a scanning light source input and a photo-cleaving light source input.

FIG. 2A depicts a particular embodiment of a scanning sensing system of the present invention. In this embodiment, the light from the photo-cleaving light source is delivered using the same optical switch 203 used for the switchable light source 202 of the optical scanning system 200. In one embodiment the optical switch 203 includes two inputs and N outputs. It is envisioned that two or more inputs can be included in optical switch 203. Optical switch 203 can be configured to switch any of the inputs to any of the outputs. A first light source 207 for optical scanning can be connected as a first input while the photo-cleaving light source input 209 can be connected to a second input of the optical switch 203. The optical switch 203 can serve to couple light from either light source input (207 or 209) to part or all of the excitation waveguides 208 which deliver light to the optical sensing sites 212.

Figure 2B:
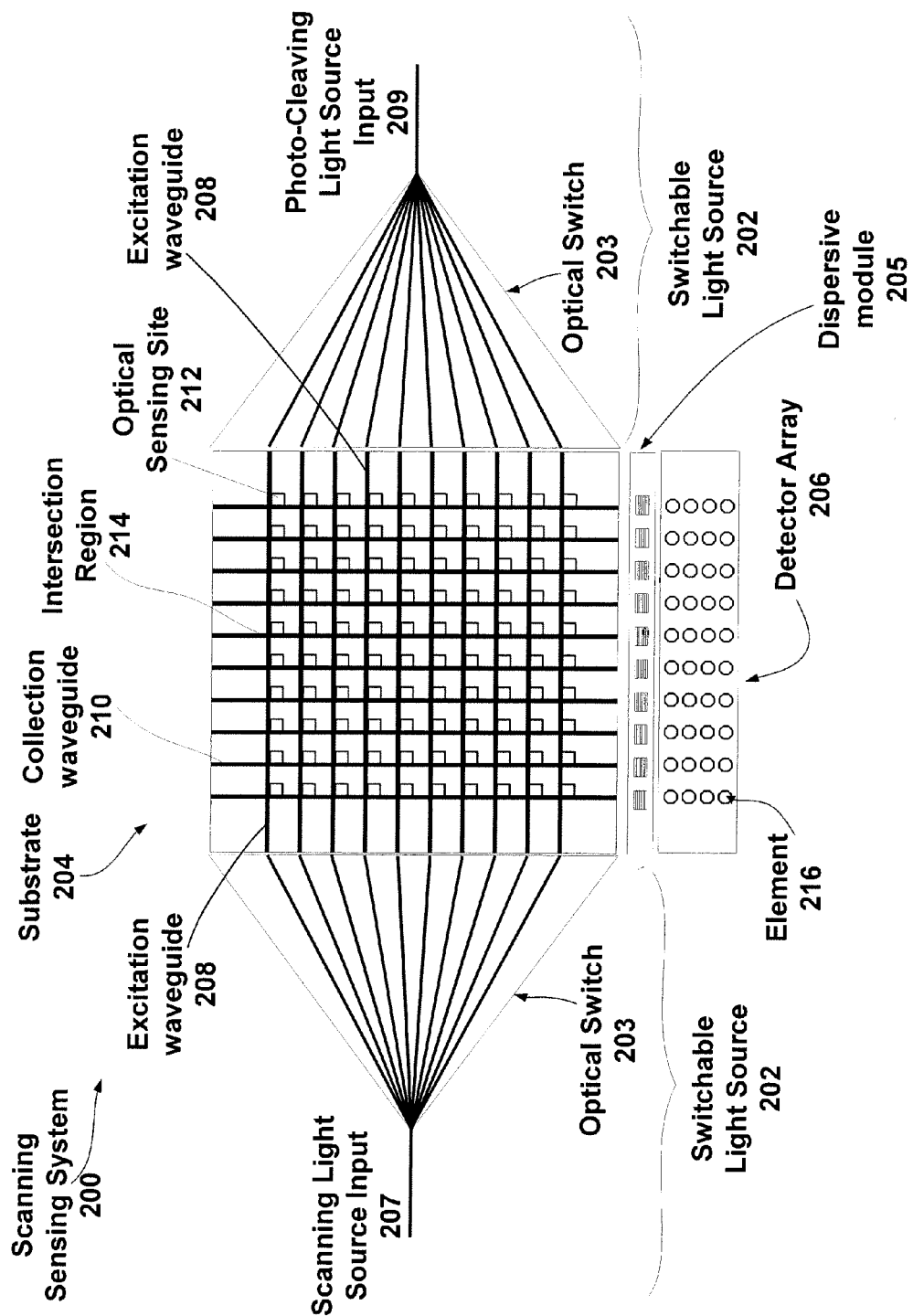
FIG. 2B is a schematic of the scanning sensing system according to another embodiment of the invention including two switchable light sources, a substrate, optical sensing sites, a dispersive module and a detector array, wherein one switchable light source includes an optical switch and a scanning light source input and the other switchable light source includes an optical switch and a photo-cleaving light source input.

FIG. 2B depicts another embodiment of a scanning sensing system of the present invention. In this embodiment the photo-cleaving light source input 209 is connected to a second optical switch 203 coupled to a second edge of substrate 204, for example, an opposite edge of substrate 204. In the case where the second optical switch 203 is disposed opposite the first optical switch 203, both optical switches can individually couple light to one or more excitation waveguides 208, which deliver light to sensing sites 212 in optical communication therewith.

Figure 2C:
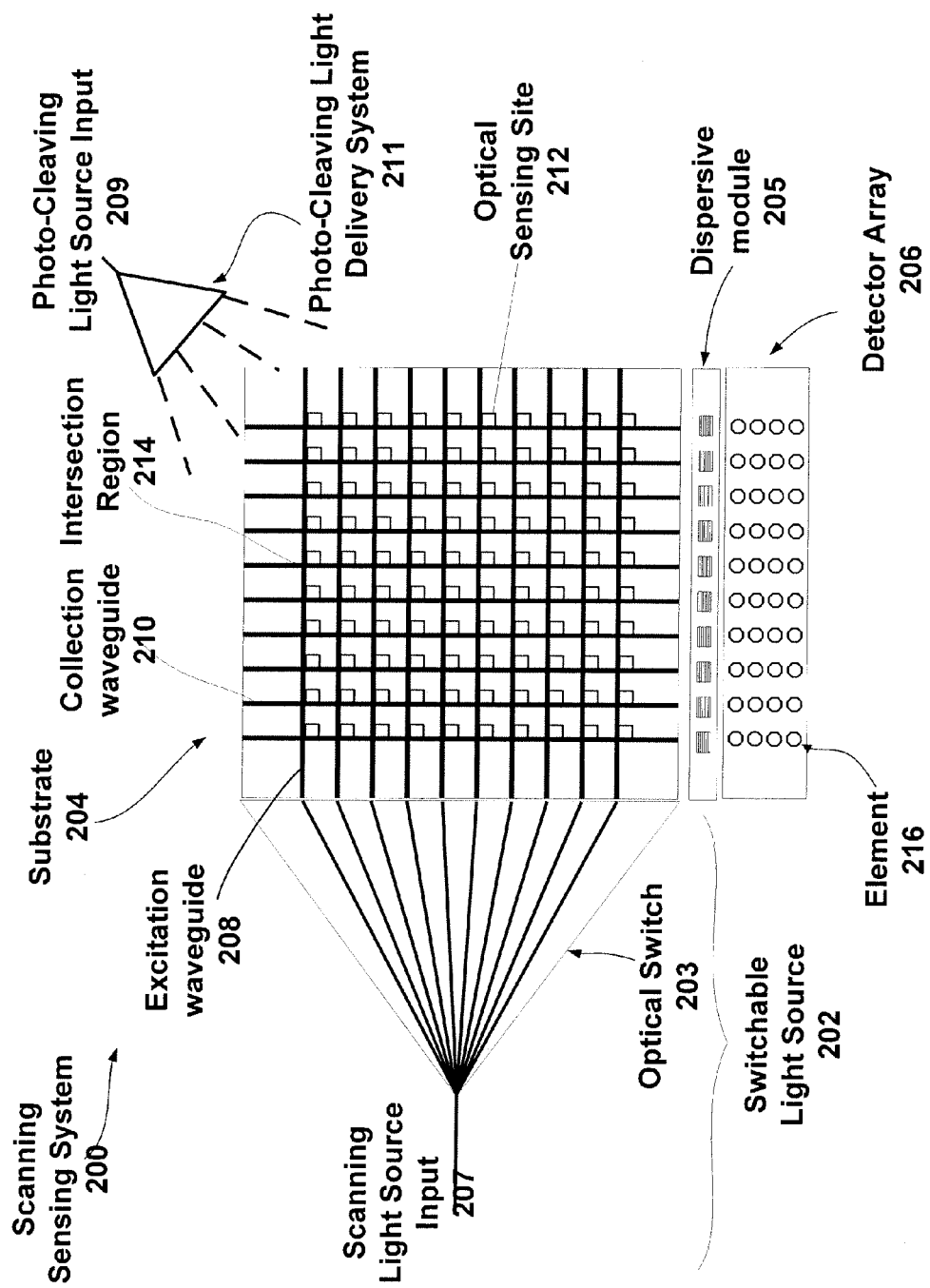
FIG. 2C is a schematic of the scanning sensing system according to one embodiment of the invention including a switchable light source, a substrate, optical sensing sites, a dispersive module, a detector array, a photo-cleaving light source input and a photo-cleaving light delivery system, wherein the switchable light source includes an optical switch and a scanning light source input.

FIG. 2C depicts an additional embodiment of the present invention. In this embodiment the light from the photo-cleaving light source is shined on substrate 204 and sensing sites 212 from above and/or below substrate 204, using a photo-cleaving light delivery system 211. It is anticipated that the photo-cleaving light delivery system may include lenses, mirrors and mechanical means to direct the light to the individual optical sensing sites or to all of the optical sensing sites at once by flooding the entire substrate (not shown).

In the case where photo-cleaving light delivery system, shines the light from below onto the substrate, the substrate can be made of optically transparent material (e.g., glass or plastic) to allow the light to also shine on the optical sensing sites (not shown). In a particular embodiment the substrate can be made of UV-transparent plastic.

Figure 3A:
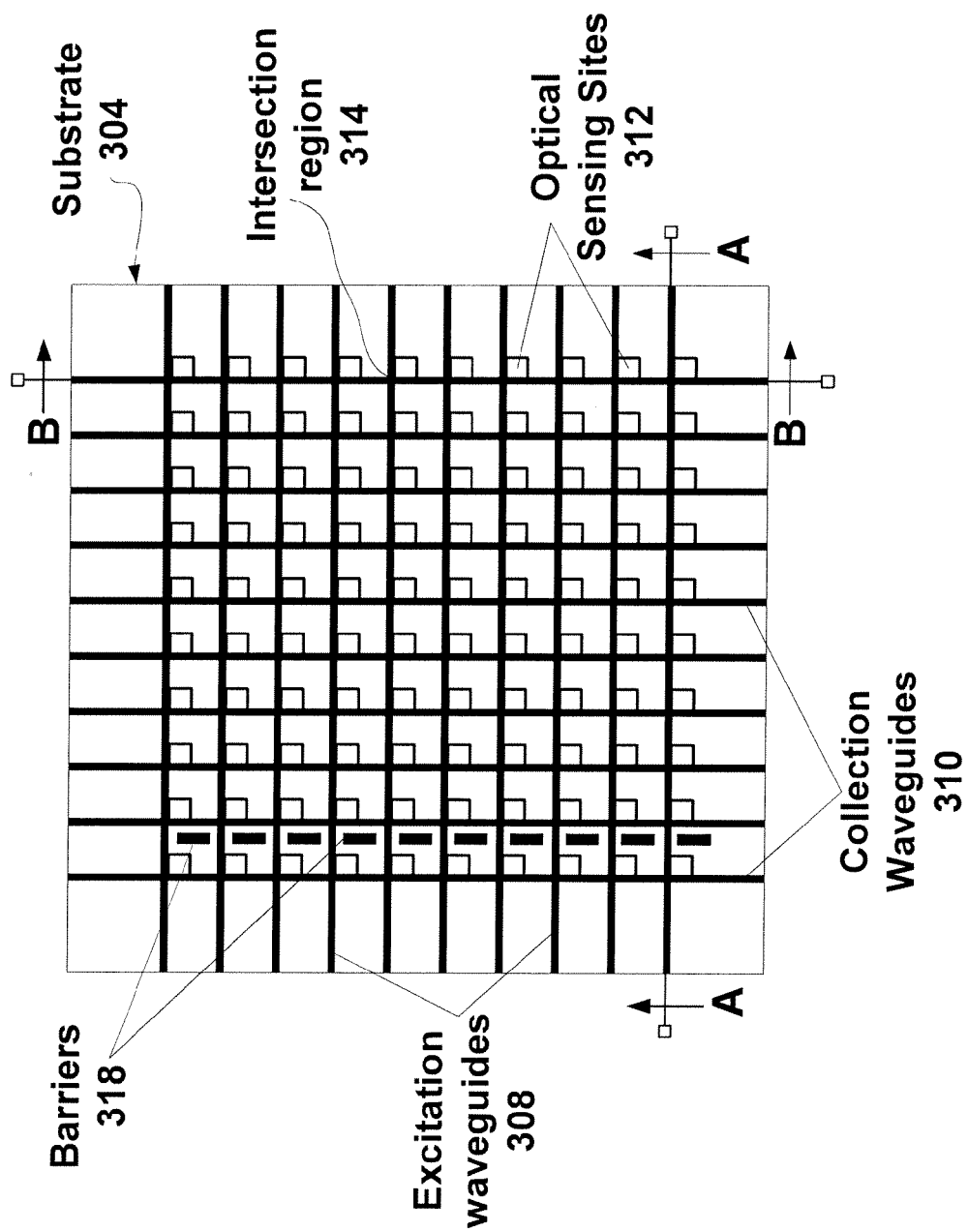
FIG. 3A is a schematic of the substrate of the invention according to another embodiment including excitation and collection optical waveguides in conjunction with optical sensing sites and barriers.

FIG. 3A illustrates an exemplary substrate 304 of the system of the invention further including barriers 318 intended to block stray light within the substrate and reduce crosstalk between the different elements of the substrate. The barriers 318 can be light absorbing or light reflecting. The barriers 318 can be variously sized, shaped and positioned between the collection waveguides 310 and/or the excitation waveguides 308 in any of a number of orientations to achieve a desired optical effect. As shown in FIG. 3A, the barriers 318 can be arranged in a row between two adjacent collection waveguides and proximal to the optical sensing sites 312 and intersection region 314.

Figure 3B:
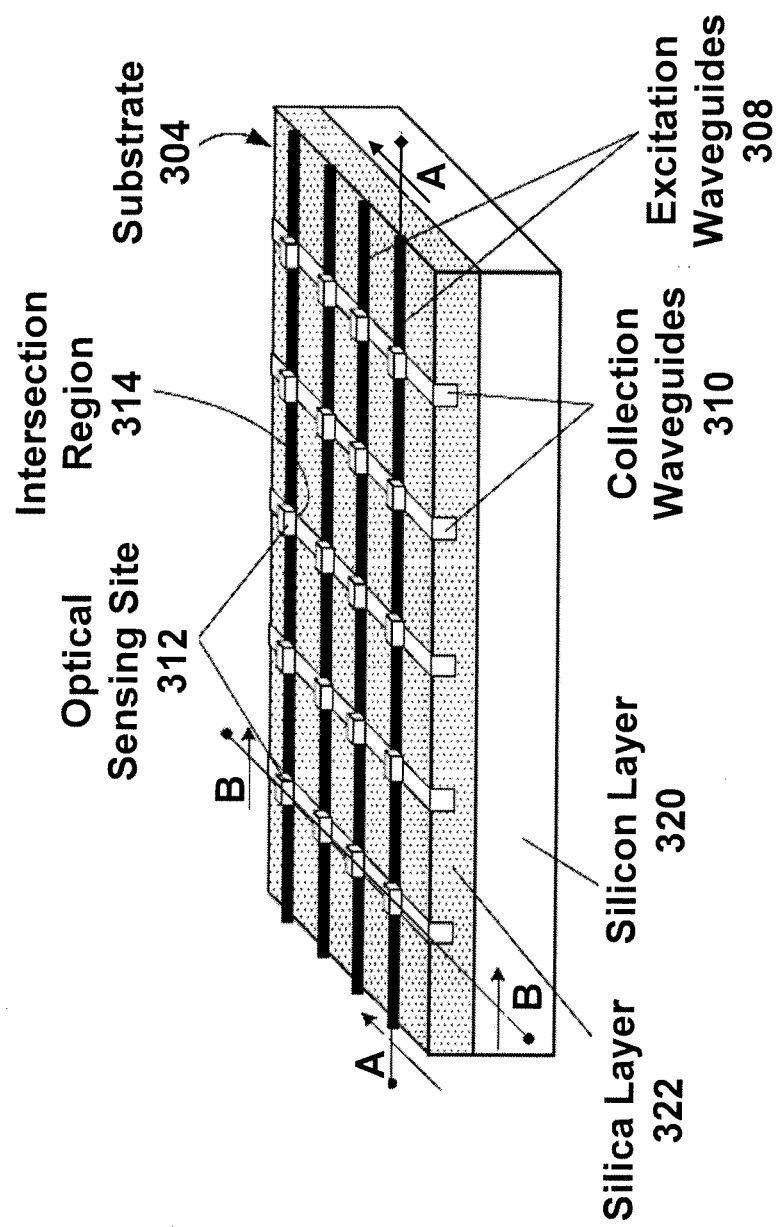
FIG. 3B is a perspective view of the substrate of the embodiment of the invention shown in FIG. 3A including excitation and collection optical waveguides in conjunction with optical sensing sites.

As shown in FIG. 3B, (in this view a top cladding layer is not shown) in one embodiment the substrate 304 can include excitation waveguides 308 and collection waveguides 310 embedded beneath a surface of the substrate 304 in multiple layers. As shown, the excitation waveguides 308 cross, physically intersect, and are in optical communication with the collection waveguides 310 at the intersection regions 314. In the embodiment shown in FIG. 3B, the optical sensing site 312 is positioned at the intersection region 314 above and in optical communication with the excitation waveguides 308. As further shown in FIG. 3B, the substrate 304 includes multiple layers including a Silicon layer 320 and a Silica ($SiO_2$) layer 322, wherein the collection waveguides 310 are embedded within the Silica ($SiO_2$) layer 322.

Figure 3C:
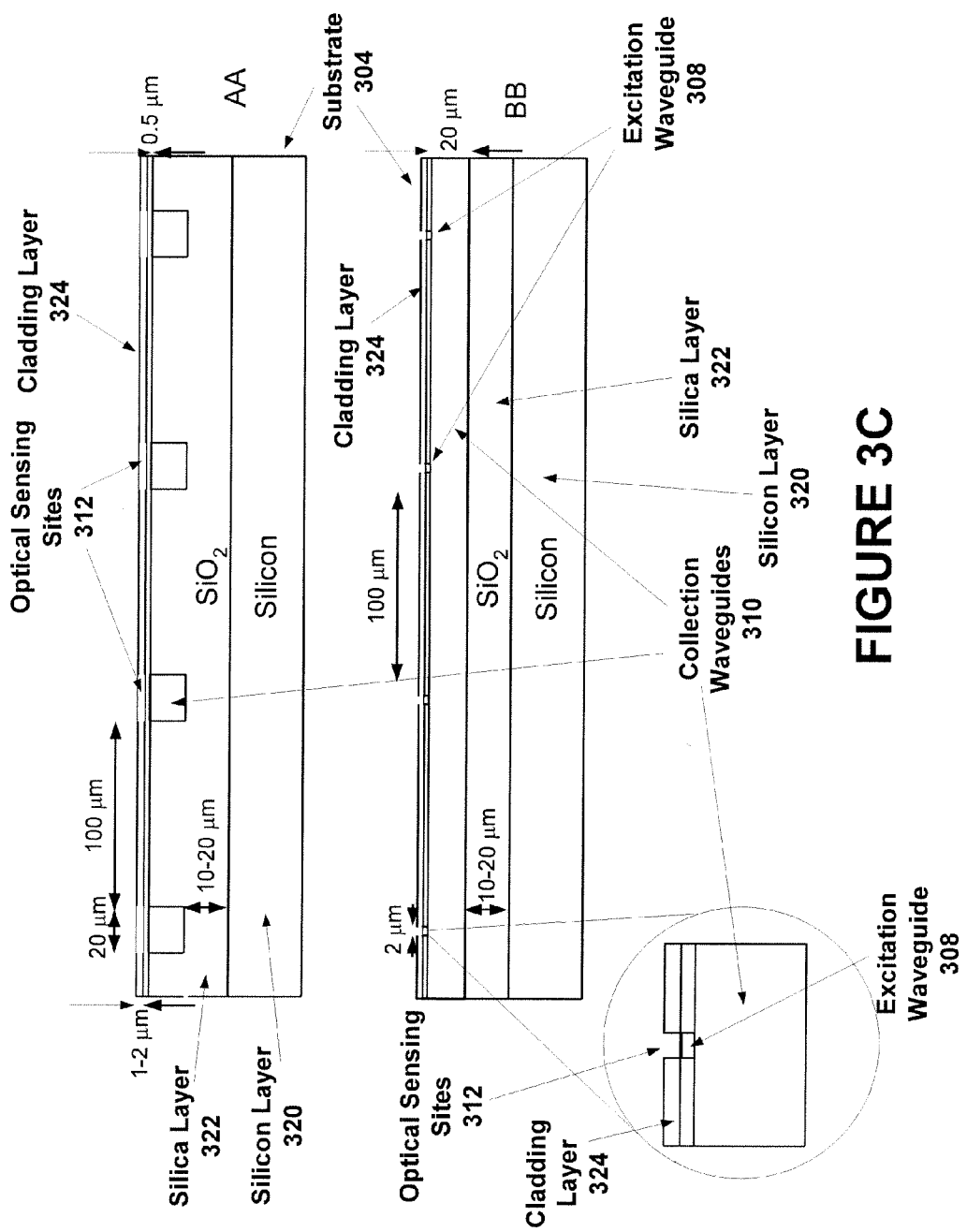
FIG. 3C is a schematic of two cross sectional views (AA and BB) of the substrate shown in FIGS. 3A and 3B.

As shown in FIG. 3C, in another embodiment the substrate can include excitation waveguides 308 and collection waveguides 310 embedded underneath a surface of the substrate 304 in a single layer. As shown, the excitation waveguides 308 cross, physically intersect and are in optical communication with the collection waveguides 310. In contrast to the embodiment shown in FIG. 3B, here the intersection between excitation waveguides 308 and collection waveguides 310 occurs internal to the collection waveguides 310. As further shown in FIG. 3C, the substrate 304 includes multiple layers including a Silicon layer 320, a Silica ($SiO_2$) layer 322, and a cladding layer 324. As shown, the excitation waveguides 308 and collection waveguides 310 can be embedded within the Silica ($SiO_2$) layer 322. Additionally, the optical sensing site 312 can be embedded within both the cladding layer 324 and the Silica ($SiO_2$) layer 322. Optionally, the optical sensing site can be embedded solely within the cladding layer (not shown).

It is envisioned that the excitation waveguides and collection wave guides can be single-mode or multi-mode waveguides. In one embodiment, the excitation waveguides are single-mode and the collection waveguides are multi-mode. It is envisioned that waveguide configurations can include single- or multi-mode configurations in either vertical or lateral orientations within a waveguide. For example, in one specific and non-limiting embodiment, the excitation waveguides 308 can support a single mode in the vertical dimension and multi modes in the lateral dimension. Optionally, as shown in FIG. 3A, the excitation waveguides 308 and the collection waveguides 310 can span the entire substrate from one edge to another edge.

As further shown in FIG. 3C, the substrate 304 components and optical sensing sites 312 can include dimensions. FIG. 3C shows two cross-section views of the substrate 304. View AA is a cross-section view in plane A as indicated in FIG. 3A and FIG. 3B. View BB is a cross-section view in plan B as indicated in FIG. 3A and FIG. 3B. As shown in FIG. 3C, the thickness of the cladding layer 324 above the excitation waveguides can be about 0.1 µm to 20 µm. In one embodiment the cladding layer 324 thickness is about 1-2 µm. By way of a non-limiting example, as shown in FIG. 3C, an opening of the optical sensing site 312 can include the following dimensions: about 20 µm×2 µm. The distance between collection waveguides 310 can range from about 1 µm to 1000 µm. For example, as shown in FIG. 3C, the distance between collection waveguides 310 can be about 100 µm. The distance between collection waveguides 310 and the Silicon layer 320 can be about 1 µm to 100 µm. For example, as shown in FIG. 3C, the distance between collection waveguides 310 and the silicon layer 320 can be about 1-20 µm.

As shown in FIGS. 3B and 3C, the excitation waveguides 308 and collection waveguides 310 can be channel waveguides. Exemplary ranges for waveguide dimensions in the embodiment shown in FIGS. 3B and 3C include about 0.1 to 100 µm thick and about 1 to 100 µm wide. By way of non-limiting example only, the excitation waveguides 208 can include cross-section dimensions of about 0.1 µm×2 µm and the collection waveguides 210 can include cross-section dimensions of about 0.1 µm×20 µm.

Figure 3D:
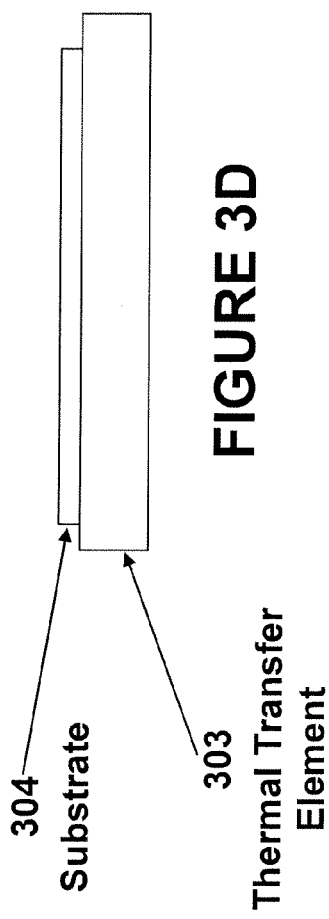
FIG. 3D is a schematic of a side view of the substrate of one embodiment of the invention in relation to the thermal transfer element.

FIG. 3D in a side view illustrates another embodiment of substrate 304 of the invention in relation to a thermal transfer element 303, for example, a thermoelectric cooler (TEC). Thermal transfer element 303 is a temperature control system useful for heating or cooling a chip, for example, substrate 304. Although the thermal transfer element may be referred to herein as a cooling element, it is to be understood that where the thermal transfer element is configured to increase and decrease the temperature of a chip, the component functions essentially as a heating and as a cooling element depending on the induced direction of the electrical current. The thermal transfer element can provide a range of useful temperatures. For example, the thermal transfer element can be configured to provide a temperature in the range between about −40° C. to about 120° C. as desired. The thermal transfer element can be adapted to receive substrate of the invention. The thermal transfer element can be adapted to contact part or all of a surface of the substrate of the invention.

Providing a thermal transfer element in conjunction with the substrate of the invention is useful, for example, for a sequencing reaction using polymerase. Alternatively, it is useful for the amplification of tested sample molecules through processes such as Polymerase Chain Reaction (PCR) as described herein. In use, the embodiment as described for FIG. 3D provides the capability of controlling the temperature of the entire substrate such that as the temperature of the entire substrate 304 can be held constant or cycled using thermal transfer element 303. Thus samples at any optical sensing site can thus be elongated by nucleic acid polymerase enzymes or other elongation methods, and/or amplified by PCR or other nucleic acid amplification methods simultaneously.

Figure 3E:
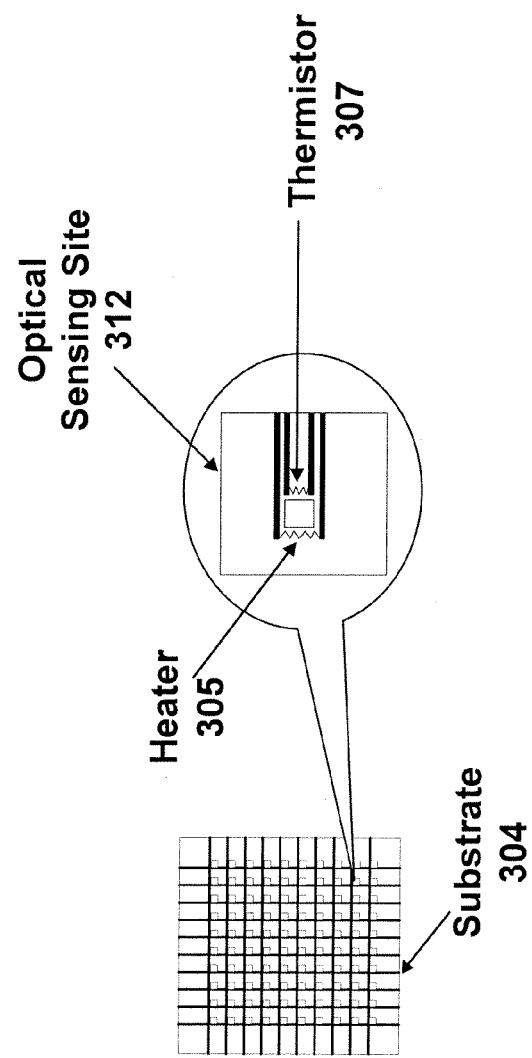
FIG. 3E is a schematic of one embodiment of the substrate of the invention illustrating details of an optical sensing site including a heater and a thermistor.

FIG. 3E illustrates another embodiment of substrate 304 of the invention wherein optical sensing site 312 includes a heater 305 and a thermistor 307. In this embodiment, optical sensing site 312 of substrate 304 can include heater 305, for example, a thin-film heater, in the vicinity of each sensing sites 312. Heater 305 can be adapted to enable individual temperature control for each sensing site 312. In addition to heater 305, thermistor 307 can be located at or near each sensing site 312 thereby providing for measuring the local temperature. In use, this embodiment provides the capability of running the same or any desired different number of cycles and the same or any desired different temperature profiles for each and every sensing site.

Advantageously, the embodiments described for FIGS. 3D and 3E can support real-time nucleic acid sequencing and/or PCR or other nucleic acid amplification methods. As described herein, since optical detection is done from within the substrate, signal detection in these embodiments (see FIGS. 3D and 3E) can be done while the samples are in the process of the sequencing and/or amplification, thereby enabling real time analysis of the process.

Figure 3F:
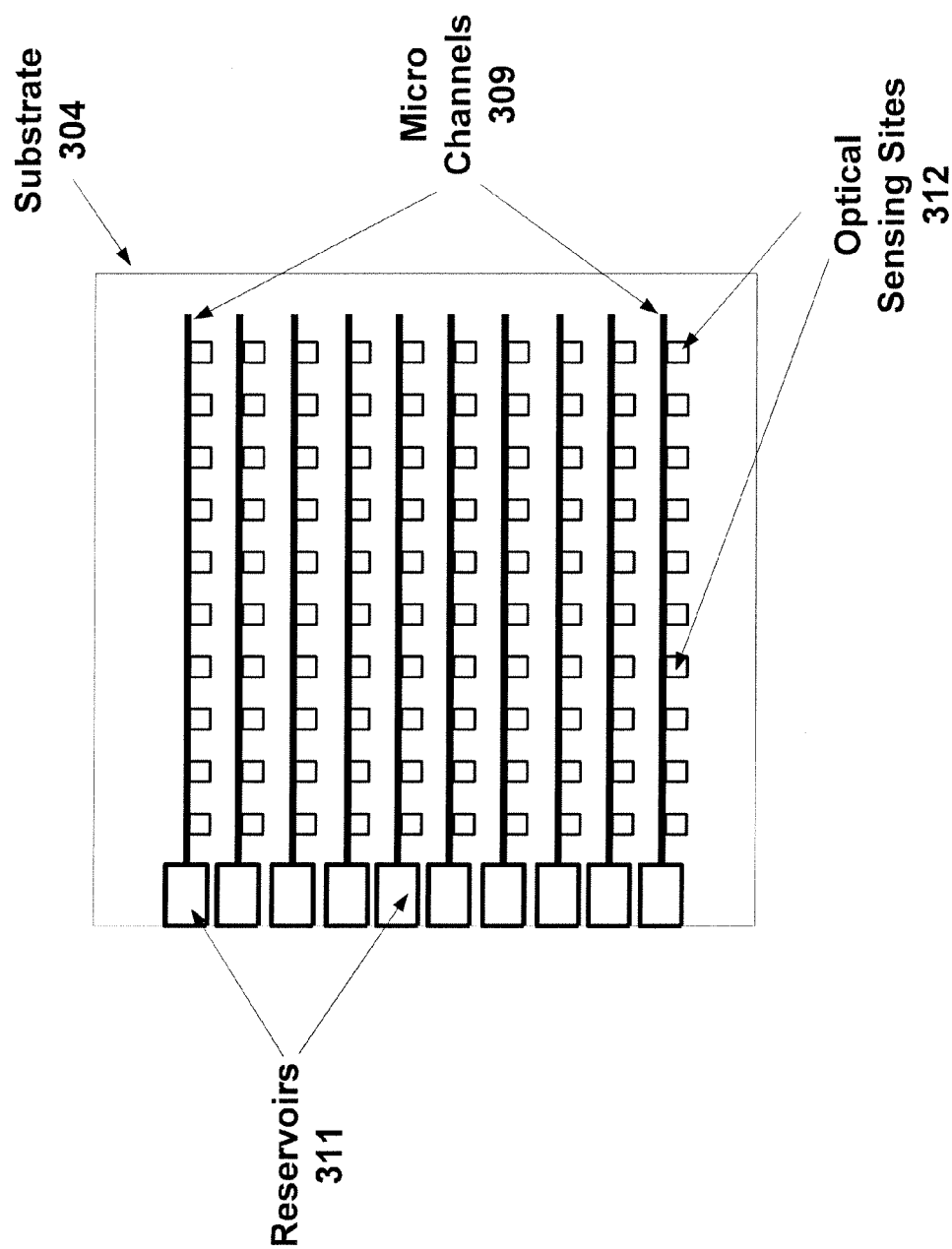
FIG. 3F is a schematic of one embodiment of the substrate of the invention including reservoirs and micro channels in relation to optical sensing sites.

FIG. 3F illustrates yet another embodiment of substrate 304 of the invention wherein substrate 304 additionally includes reservoirs 311 and microchannels 309 in relation to optical sensing sites 312 (note that the waveguides are not shown in this illustration for easier viewing). As such, in this embodiment microfluidics are incorporated into the substrate. Microfluidics can be adapted to drive liquid (in this case the tested sample) using the capillary effect across the substrate. As illustrated in FIG. 3F, this can be achieved by an arrangement of microchannels 309, optionally of varying width, which force the sample from one or more reservoirs 311 to optical sensing sites 312 which can include etched wells to receive the sample. The microchannels can be either etched on the face of the chip itself or can be added as an external structure on a surface of the sensing chip.

In use, it is envisioned that a sample to be tested can be pipetted into a reservoir at one end of the substrate. The sample can then be distributed using the microfluidic system to the optical sensing sites and sensing wells where it is allowed to bind to pre-spotted probes and can subsequently be optically scanned and analyzed. Several reservoirs may be used to separate different samples/patients or for running several parallel tests.

It is envisioned that one or more primer oligonucleotides or nucleic acid polymerase enzymes can be applied to the optical sensing sites using a print head. Furthermore, it is envisioned that delivery of sample to the optical sensing sites of the system comprises delivering the sample using an assay head or flow-cell attached to the upper surface of substrate 304. One possible print head technology is described in U.S. patent application Ser. No. 11/241,060, filed on Sep. 30, 2005, and U.S. patent application Ser. No. 11/632,086, filed on Jul. 6, 2005.

Figure 4A:
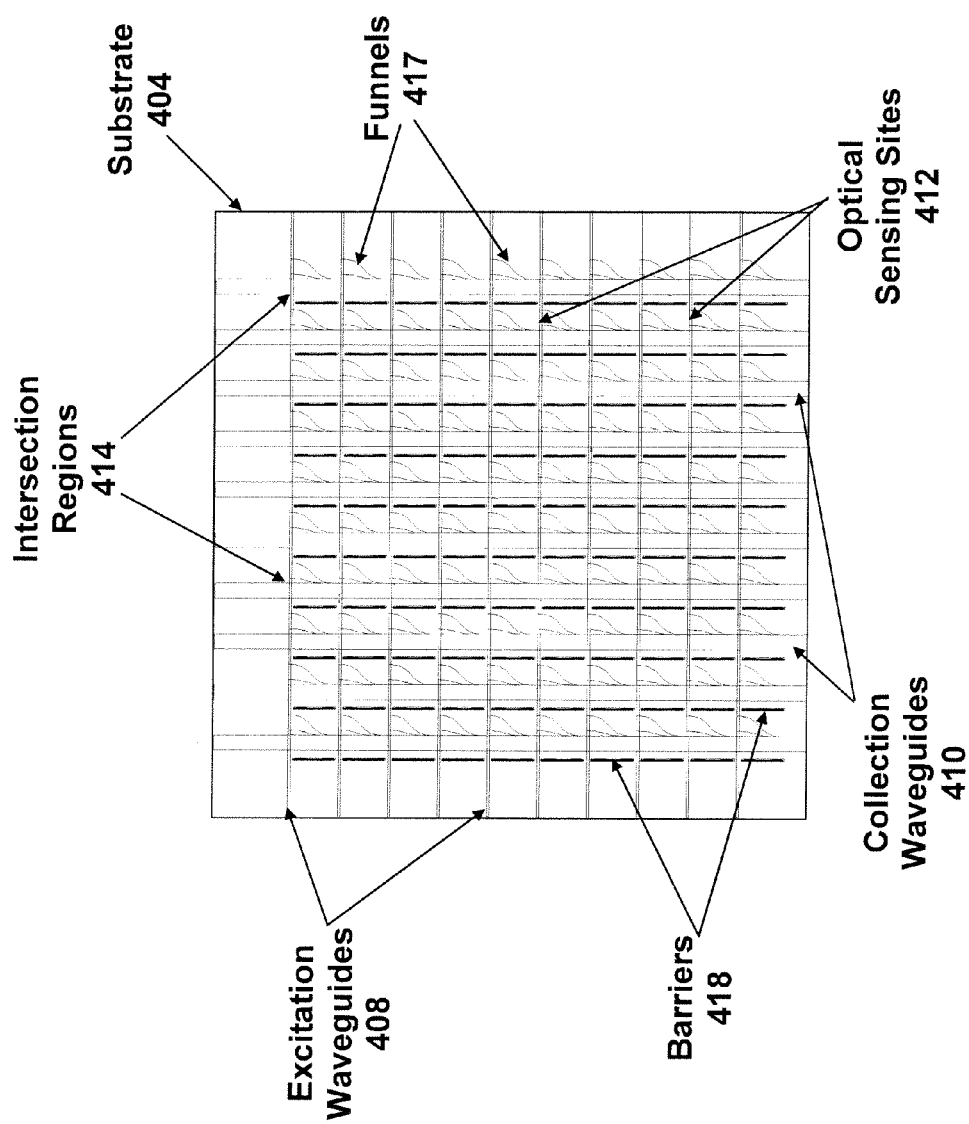
FIG. 4A is a schematic of the substrate of the invention including excitation and collection optical waveguides in conjunction with optical sensing sites, barriers and funnels.

FIG. 4A in a top view illustrates an exemplary substrate 404 of the system of the invention wherein the collection waveguides 410 include funnels 417 (shown in detail in FIG. 4B) for collecting light.

As shown in the example in FIG. 4A, the substrate 404 can include a 10×10 array consisting of 10 excitation waveguides 408 (e.g., 5 µm wide×2 µm deep), 10 collection waveguides 410 (e.g., 30 µm wide×10 µm deep), 100 optical sensing sites 412 (e.g., wells 30 µm long×5 µm wide×10 µm deep), 100 funnels 417 for collecting light from the optical sensing sites 412 and barriers 418 (e.g., light absorbing channels) to reduce crosstalk between the optical sensing sites 412. Although the example shown in FIG. 4A includes a 10×10 array of excitation waveguides 408 and collection waveguides 410, it is envisioned that the substrate can include greater than 10, greater than 100 or greater than 1,000 excitation waveguides 408 and collection waveguides 410.

In the embodiment shown in FIG. 4A, excitation light can be coupled into one or more excitation waveguides 408 on the left hand side of the substrate 404 through, for example, chip-to-chip butt coupling. Excitation light can travel along the excitation waveguides 408 and couple into the optical sensing sites (e.g., wells) through an evanescent field tail. Additionally, the switchable light source can include one or more waveguide and can be evanescently coupled to the substrate through a proximate arrangement of the one or more switchable light source waveguide and one or more excitation waveguide of the substrate. Excited fluorescence generated in the optical sensing site 412 can be collected along the long facet of the optical sensing site 412 into the funnels 417. The funnels 417 can channel the light into the collection waveguides 410. The light in the collection waveguides 410 can be coupled out at the "bottom" of the substrate 404 into a detector array (not shown). Light scattered outside the optical sensing sites 412 can be blocked by a series of barriers 418 (e.g., light absorbers) to avoid crosstalk between parallel collection waveguides 410.

In one embodiment, the substrate shown in FIG. 4A includes two waveguide layers. As illustrated in cross-sectional view in FIG. 4C, a first 2 µm thick bottom layer can include the excitation waveguide 408. The bottom layer can have a higher refractive index in order to increase the evanescent field tail presence in the optical sensing sites. An upper 10 µm thick layer can contain the optical sensing site and the light collection structures (funnels and waveguides). The upper layer can have a lower refractive index than the bottom layer in order to minimize light loss when coupling the light out of the substrate to the detector.

In a particular embodiment of the above, both the excitation and collection waveguides are multimode. Furthermore, the switchable light source (e.g., an optical switch or an array of light generators coupled to an array of waveguides) can include single-mode waveguides, that can be butt-coupled or can evanescently couple to the substrate.

Figure 4C:
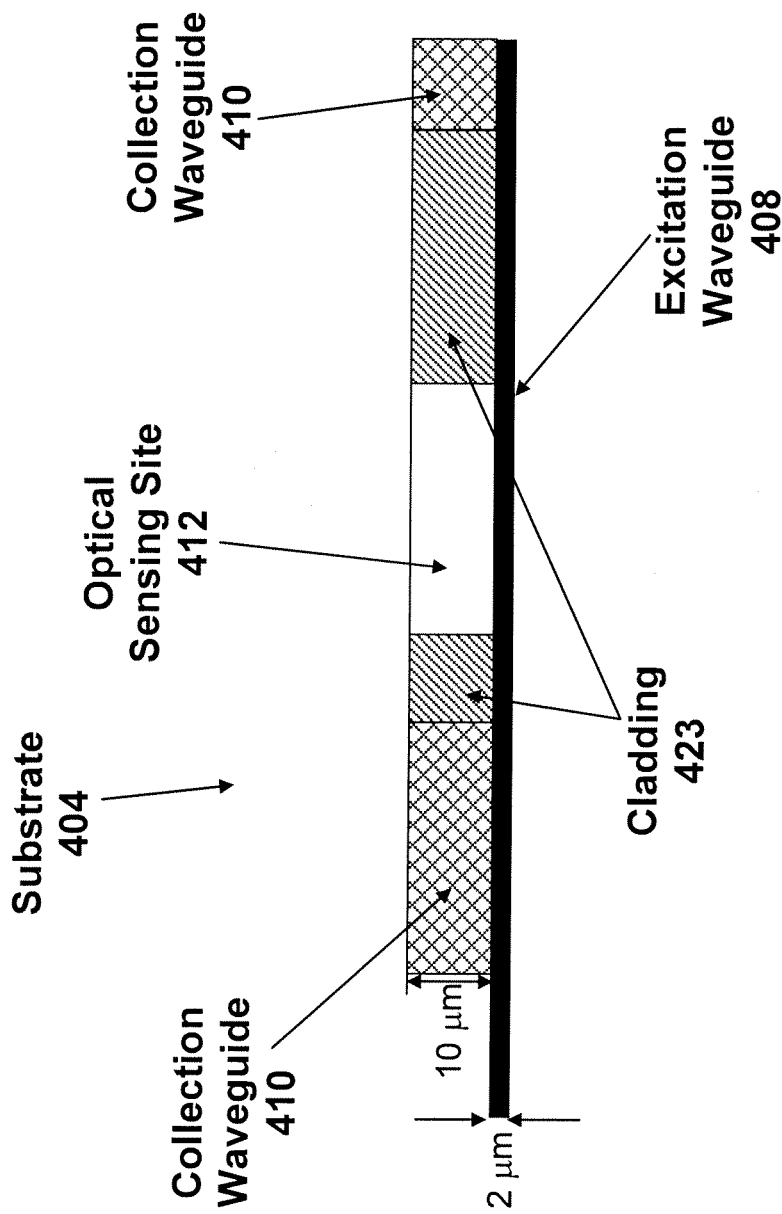
FIG. 4C is a schematic of a cross-sectional view of the substrate according to one embodiment.

As shown in cross-sectional view in FIG. 4C, in order to minimize the loss of light at the waveguide crossing points due to light coupling from the collection waveguides 410 into the excitation waveguides 408, the excitation waveguides 408 can be thinner than the collection waveguides 410. For example, as shown in FIGS. 4B and 4C, the excitation waveguides 408 can have a width of 5 µm (see FIG. 4B) and a height of 2 µm (see FIG. 4C). As further shown, the collection waveguides 410 can have a width of 30 µm (see FIGS. 4A and 4B) and a height of 10 µm (see FIG. 4C).

It is envisioned that light coupled at the waveguides crossing points between the excitation waveguides and the collection waveguides can shine directly into the optical sensing sites, thereby increasing light excitation rather than being lost.

As shown in FIG. 4B, the optical sensing sites can be wells that are narrow (1 µm) and long (30 µm) with light collectable along the long facet. Such a configuration increases the efficiency of light collection. In addition, light excitation coupling into the well can increases due to the long coupling length. The well dimensions (5×30×10 µm$^3$) yield a volume of 1.5 pico-liter. Larger wells are also envisioned in a variety of sizes yielding volumes ranging from about 0.1 pico-liter to 100 micro-liter.

The funnel can have a radii for the collection, confinement and coupling of light into the collection waveguides. Suitable ranges for radii can include from about 100 µm to about 1000 µm.

The barriers 418 as illustrated in FIGS. 4A and 4B, can be trenches filled with light absorbing material (e.g., a metal such as gold). Where the barriers 418 are trenches, the trenches can include openings above the excitation waveguide 408 to avoid loss at the crossing points (not shown).

The overall dimensions of the substrate illustrated in FIG. 4A can be 1.2×1.2 mm$^2$. Margins can optionally be included around the substrate to adjust the overall dimensions as desired.

Figure 5A:
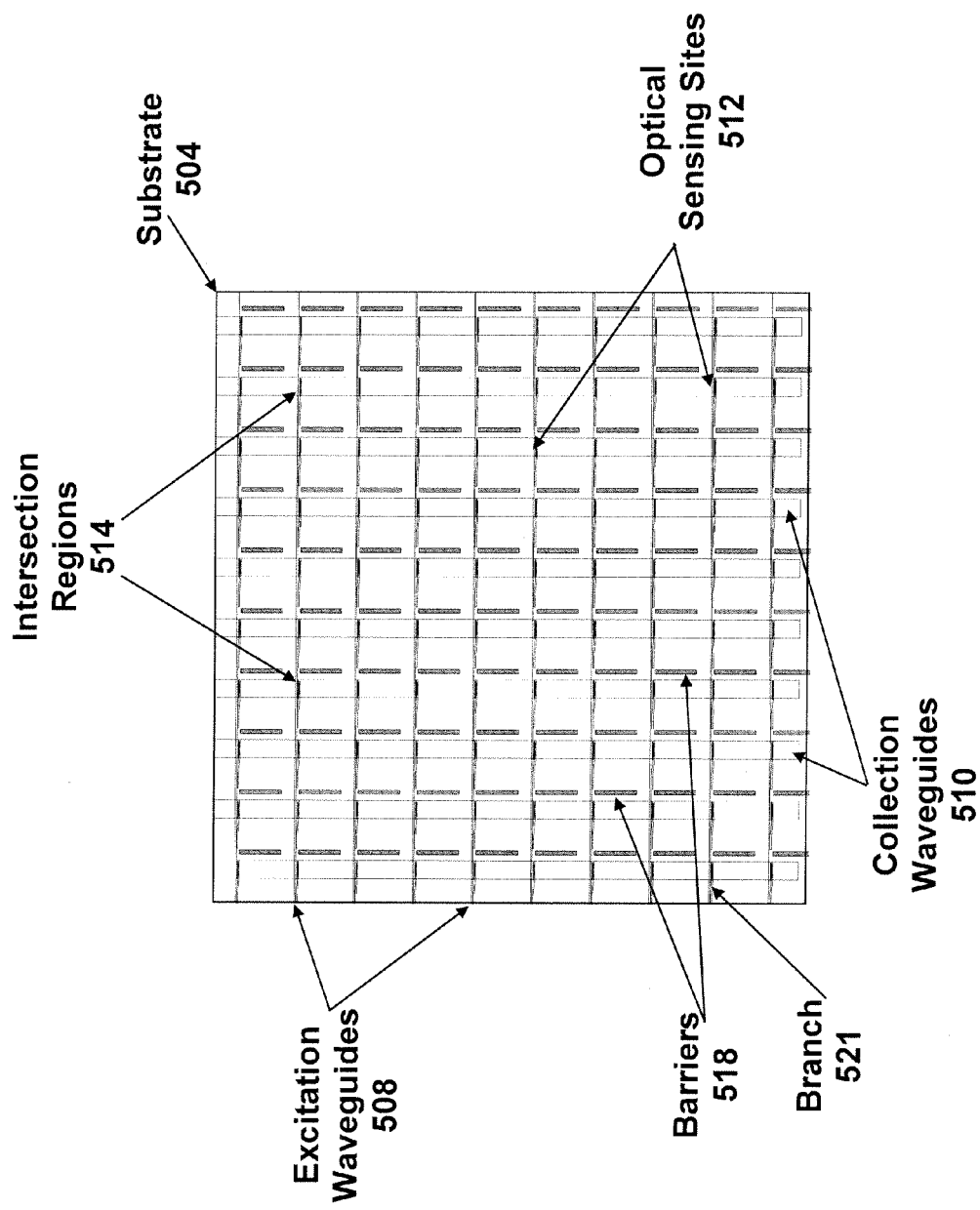
FIG. 5A is a schematic of one embodiment of the substrate of the invention including excitation and collection optical waveguides in conjunction with optical sensing sites, barriers and branches.

FIG. 5A illustrates an exemplary substrate 504 of the system of the invention wherein the excitation waveguides 508 include a plurality of branches 521 (shown in detail in FIG. 5B) for tapping light from the excitation waveguides and coupling it into the sensing wells.

Figure 5B:
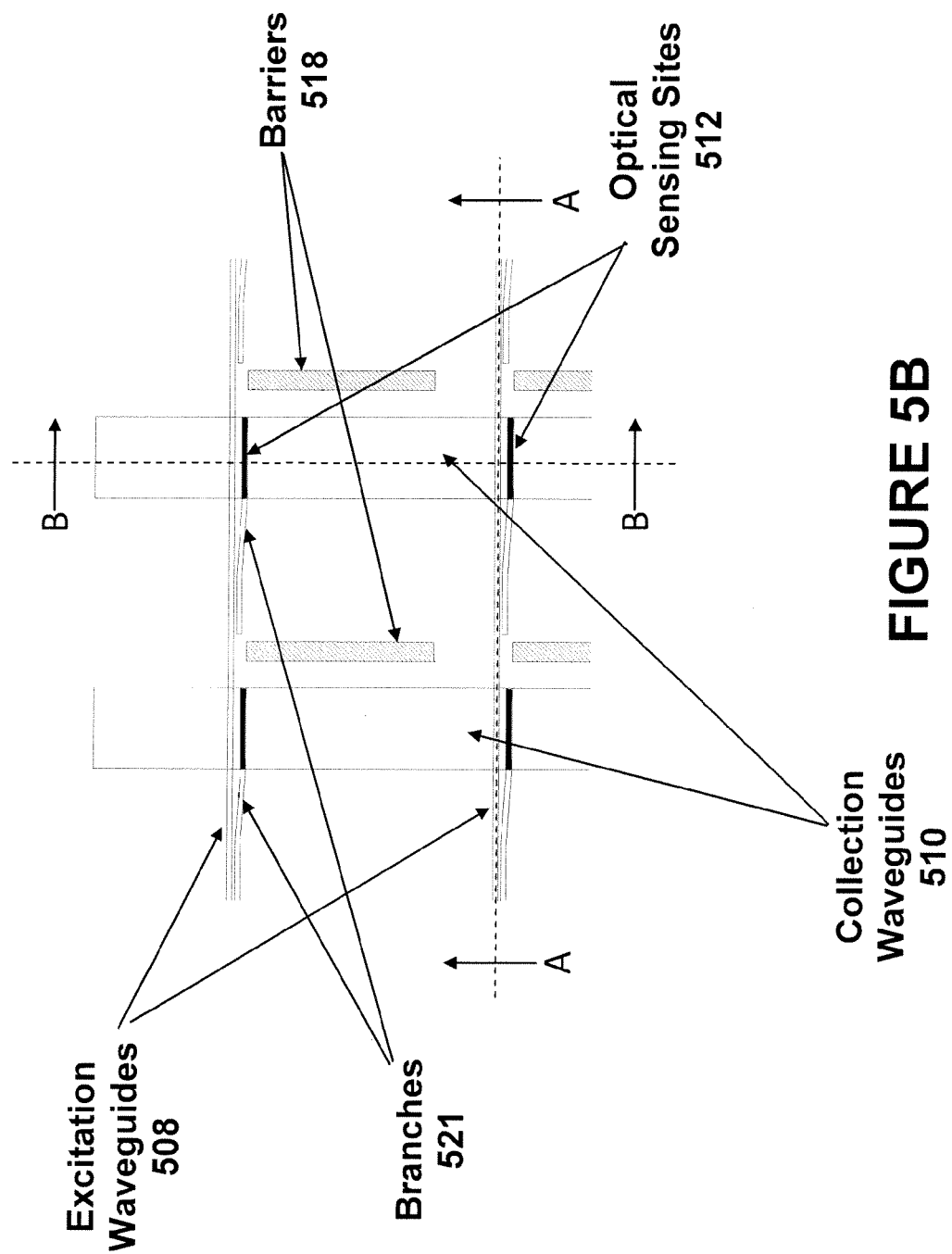
FIG. 5B is a schematic showing an enlarged view of substrate features according to an embodiment as shown in 5A.
Figure 5C:
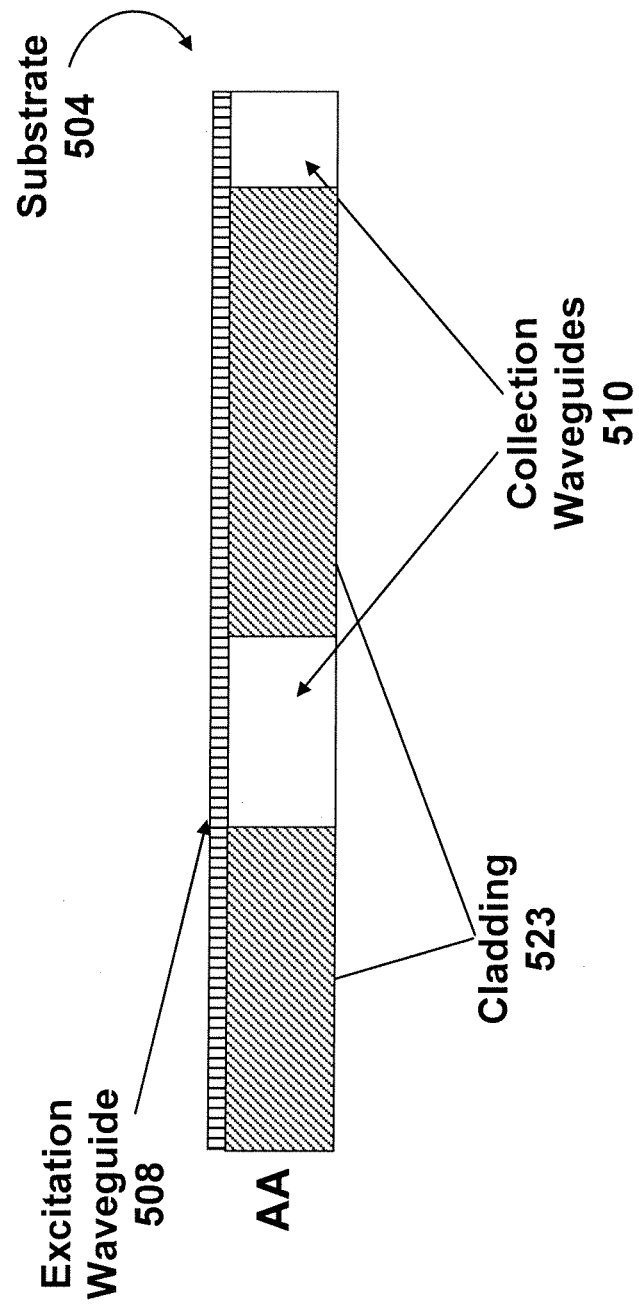
FIG. 5C is a schematic of a cross-sectional view in a plane (AA) of the substrate according to one embodiment.
Figure 5D:
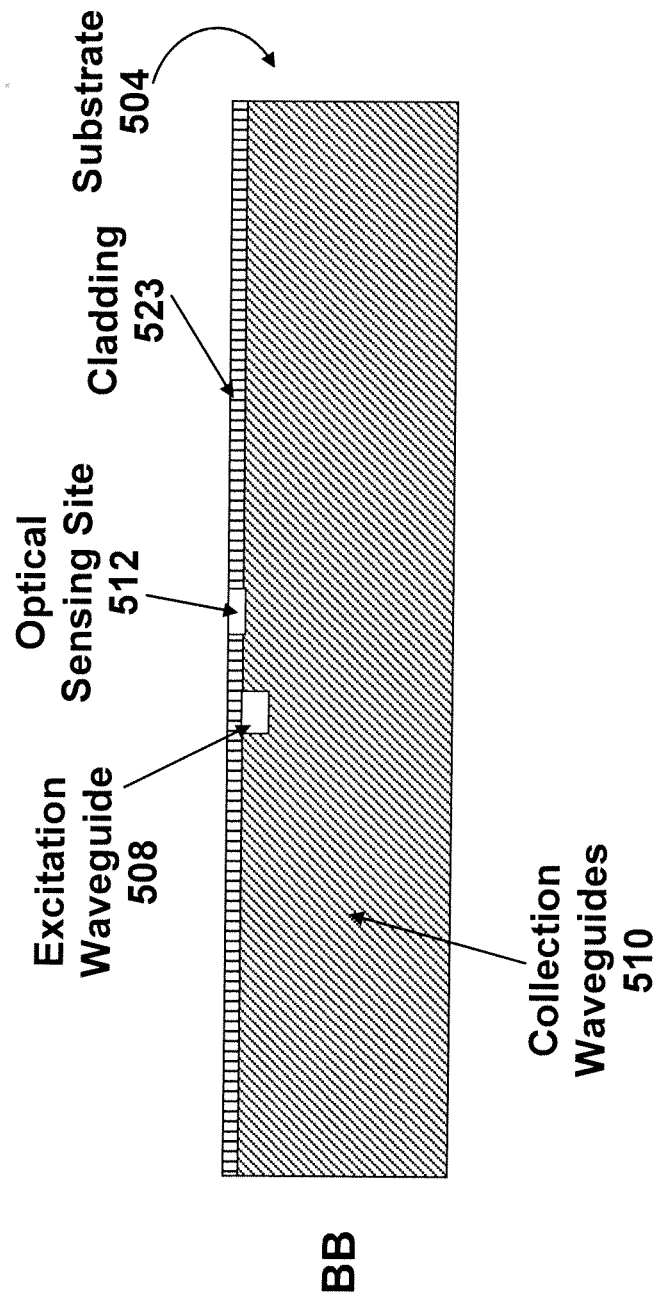
FIG. 5D is a schematic of a cross-sectional view in a plane (BB) of the substrate according to one embodiment.

In the embodiment shown in FIG. 5A, the substrate 504 can be made up of several waveguide layers (e.g., three waveguide layers). Such a configuration can be useful, for example, to optimize excitation and fluorescence collection while minimizing loss and crosstalk. FIGS. 5C and 5D are schematic cross-section views of the substrate 504 through planes at (AA) and (BB) respectively as indicated in FIG. 5B.

In one embodiment the substrate consists of three waveguide layers having core refractive index of 1.7 and clad reflective index of 1.4. Useful core refractive index values range from about 1.45 to 2.2, and useful clad refractive index values range from about 1.4 to 2.

As shown in FIGS. 5C and 5D, in one embodiment where the substrate 504 includes three waveguide layers, a first bottom layer can be about 10 µm thick and include the collection waveguides 510. In the embodiment illustrated in FIG. 5A, the collection waveguides 510 can be 30 µm wide, multimode and traverse the substrate 510 from substantially edge to edge. A second middle waveguide layer can be 0.1 µm to 1 µm thick and include coupling waveguide branches 521 (see FIGS. 5A and 5B). The branches 521 can couple excited light into the optical sensing sites, which can be wells. A third top layer can be 2 µm thick and include single-mode excitation waveguides 508 and traverse the substrate substantially from edge to edge.

A range of dimensions for the various features described herein include: waveguides thickness—20 nm to 50 µm; waveguide width—1 µm to 500 µm; waveguide length—1 mm to 100 mm; optical sensing site length—1 µm to 100 mm; optical sensing site width—1 µm to 500 µm; optical sensing site depth—0 to 20 µm; waveguide pitch—10 µm to 10 mm; substrate thickness—100 µm to 5 mm; upper cladding thickness—0 to 20 µm; and lower cladding thickness—0.1 µm to 20 µm.

The substrate of the scanning sensing system can made up of any of a number of well known materials suitable for use in planar lightwave circuits. For example, useful substrate materials include but are not limited to Silicon, Silica ($SiO_2$), glass, epoxy, lithium niobate and indium phosphide as well as combinations thereof. The waveguides disclosed herein can be made up of Silicon, Silica ($SiO_2$) and derivatives thereof, silicon oxynitride ($SiO_xN_y$) and derivatives thereof, silicon nitride ($Si_3N_4$) and derivatives thereof, polymers, lithium niobate and indium phosphide as well as combinations thereof. In one embodiment, UV light is used to change the refractive index of a waveguide material after deposition.

Figure 6A:
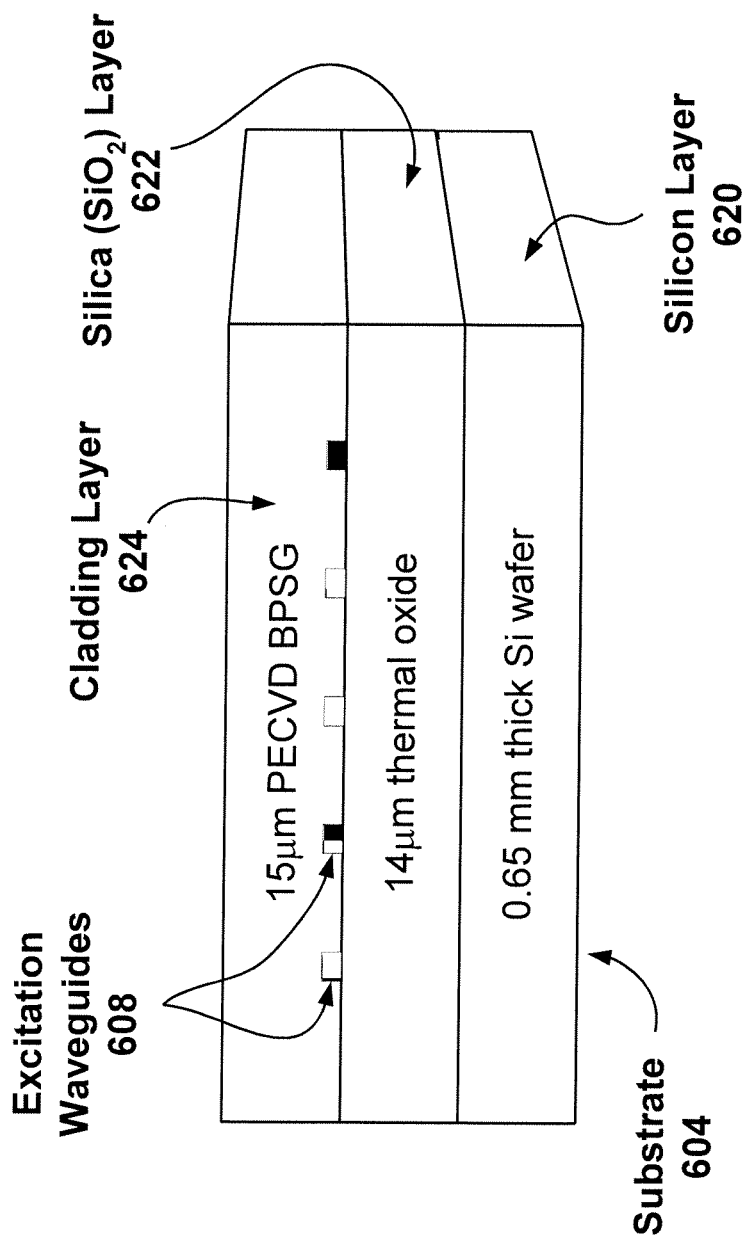
FIG. 6A is a schematic of a general substrate including typical layers and waveguides representative of those of the current invention.

FIG. 6A illustrates an exemplary silicon layer 620 of the substrate 604. For example, the silicon layer 620 can be made up of a silicon wafer having a thickness from about 0.1 mm to 2 mm. In another example the silicon wafer can have a thickness from about 0.3 to 1 mm. In a particular example as illustrated in FIG. 6A, the silicon wafer has a thickness of 0.65 mm. As shown in FIG. 6A in one embodiment, the silica ($SiO_2$) layer 622 is a 14 µm thermal oxide layer of Silica ($SiO_2$) created by placing the Silicon in an oxygen-rich environment inside a furnace at high temperature. The top Silicon layer oxidizes over time (several hours) creating a $SiO_2$ layer. Additionally, as shown in FIG. 6A, in one embodiment, the cladding layer 624 is 15 µm thick and deposited by a PECVD (Plasma-Enhanced Chemical Vapor Deposition) process after etching to produce the waveguides 608.

It is envisioned that the various layers of the substrate can include different refraction index properties. For example, a waveguide layer (e.g. $Si_3N_4$) has a higher refraction index than a cladding layer of silica deposited thereon.

Figure 6B:
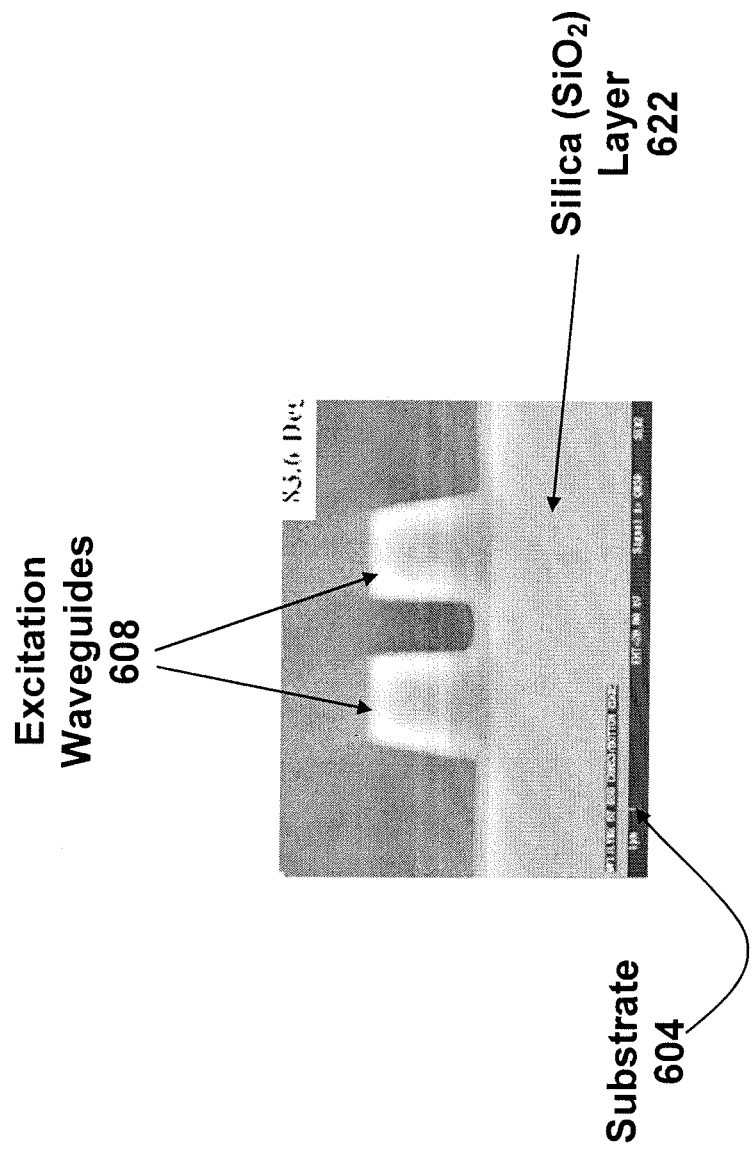
FIG. 6B is a photomicrograph image of waveguides representative of those of the invention and a silica layer.
Figure 6C:
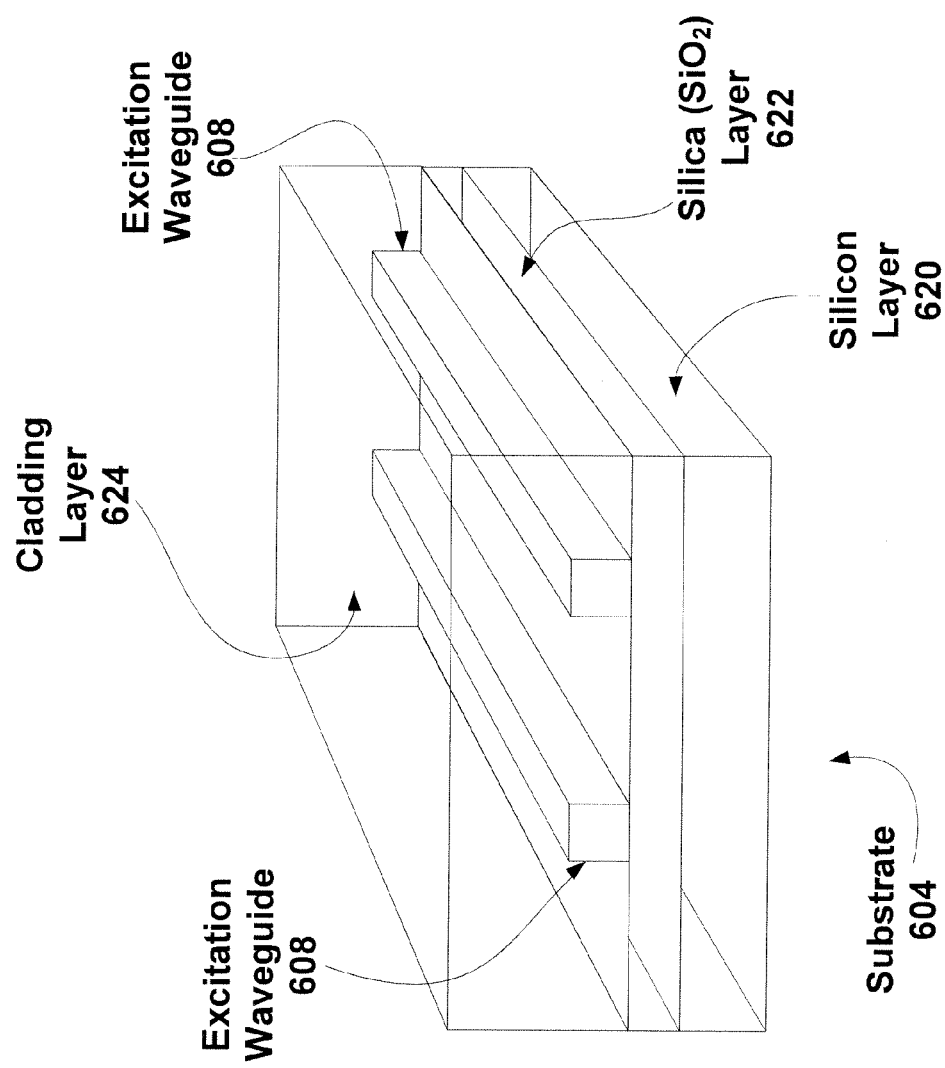
FIG. 6C is a perspective view of waveguides and associated substrate layers.

As shown in FIG. 6B (illustrated with a photomicrograph prior to deposition of a cladding layer), in some embodiments, the substrate 604 can include two waveguides 608 arranged for light wave coupling on a silica ($SiO_2$) layer 622. Alternatively, as shown in FIG. 6C, two waveguides 608 can be arranged for guiding uncoupled light waves on a silica ($SiO_2$) layer 622 and over-clad with a cladding layer 624.

Figure 7A:
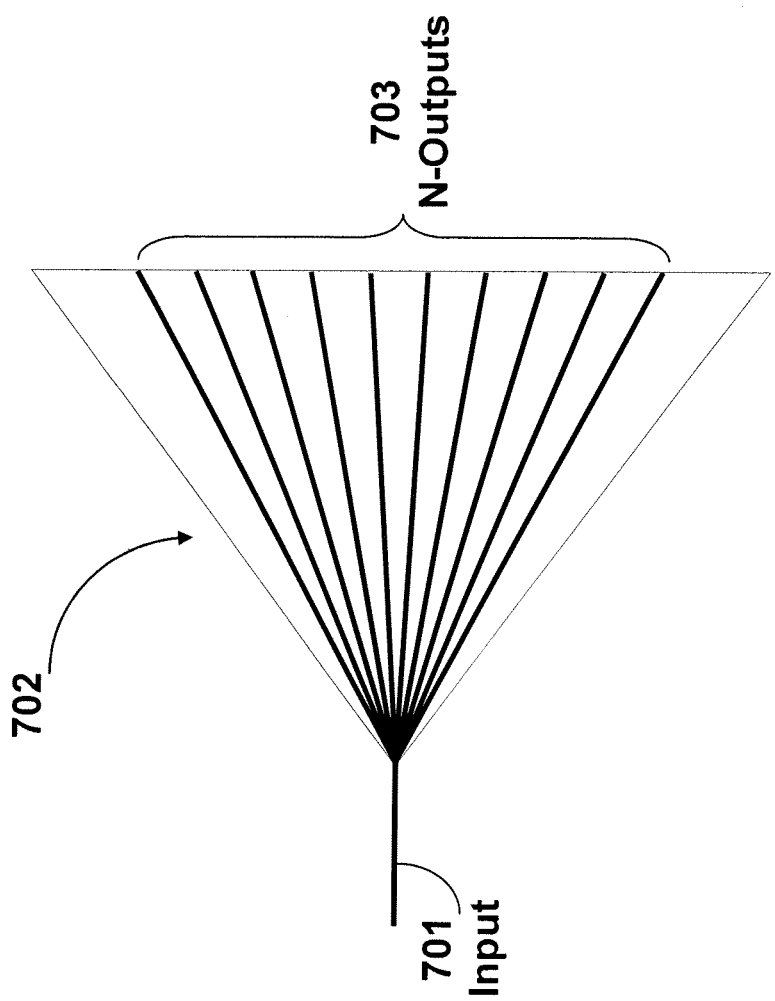
FIG. 7A is a schematic of a switchable light source of the invention including inputs and outputs.

FIG. 7A illustrates an exemplary switchable light source 702 of the system of the invention, including one or more inputs 701 as a primary source of light for coupling to a light generator. The light generator can be any source of electromagnetic radiation emitting one or more discrete spectral-lines or a continuous spectrum (not shown). In one embodiment the light generator is a laser source emitting in one or more well defined wavelengths. In a second embodiment the light generator is a tunable laser that can be tuned to emit light in one wavelength within a predefined range. As illustrated, switchable light source 702 further includes a plurality of outputs 703 shown in FIG. 7A as N-Outputs. The number of outputs 703 included in switchable light source 702 can be variable based on the intended use. For example, in certain applications the number of outputs 703 can be greater than 10 outputs. In one embodiment the number of outputs 703 can be great than 100 outputs. In a further embodiment the number of outputs 703 can be greater than 1,000 outputs. In another embodiment the number of outputs 703 ranges from about 50 to 500.

The switchable light source can be a passive 1×N splitter with N being for example, between 1 and 1,000. It is further envisioned that N can be greater than 1,000, greater than 10,000 or greater than 100,000. Such an arrangement is advantageous in that is allows for simultaneous (e.g. parallel) excitation in waveguides of the system as described herein.

Figure 7B:
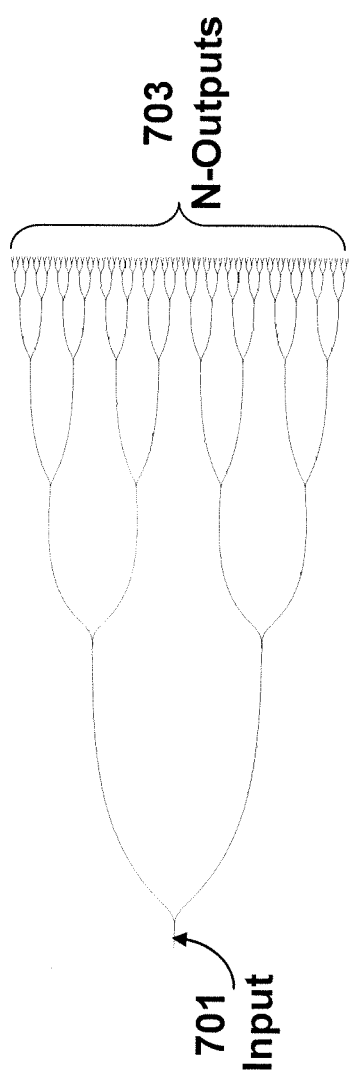
FIG. 7B is a schematic of a branched architecture between the inputs and outputs of a switchable light source of the invention.

In a particular embodiment, the number of outputs 703 is about 128. As shown in FIG. 7A, in one embodiment, the switchable light source includes outputs 703 that fan out from an input 701 equally splitting the light at input 701 to all outputs 703. As illustrated in FIG. 7B, in one embodiment a branched architecture stemming from the input 701 to the outputs 703 can be used. Although only one input is shown in FIGS. 7A and 7B, it is envisioned that multiple inputs 701 can be used.

Figure 7C:
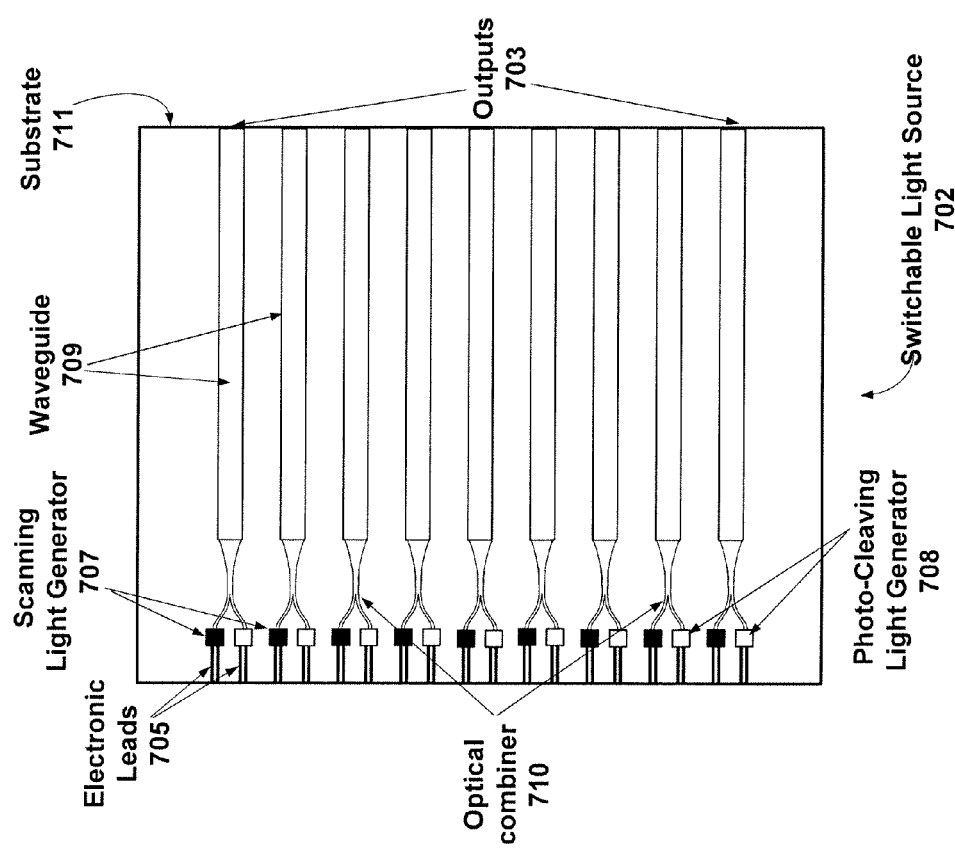
FIG. 7C is a schematic of another embodiment of the switchable light source of the invention including light generators and waveguides.

FIG. 7C illustrates another exemplary switchable light source 702 of the system of the invention including multiple outputs. In this embodiment switchable light source 702 includes a plurality of waveguides 709, scanning light generators 707, photo-cleaving light generators 708 and electronic leads 705. As shown in FIG. 7C in one non-limiting example, waveguides 709 can be arranged in parallel across substrate 711. In other embodiments waveguides are arranged in a non-parallel fashion (not shown). Waveguides 709 can terminate in outputs 703 as described herein.

As shown in FIG. 7C, a plurality of scanning light generators 707 and photo-cleaving light generators 708 can be coupled into waveguides 709 through an optical combiner 710. As further shown in FIG. 7C, light generators 707 and 708 can be in electrical communication with electronic leads 705. Electronic leads can in turn be in electrical communication with any of a number of apparatus including but not limited to a power supply or an electronic driving circuit (not shown).

It is envisioned that the switchable light source can be a dynamic light source allowing for selective and programmed generation of the primary light wave through one or more individual output. In one embodiment the switchable light source is an optical switch, for example, a planar optical switch. The switchable light source can be a light manipulating device for switching light from a given input to any given output. Moreover, the switchable light source can multicast an input light to several outputs all at the same time. In one embodiment, switchable light source is an optical switch coupled to a light generator through one or more optical fiber (not shown). In a particular embodiment, the light generator is coupled to one or more of the inputs of the switchable light source. By way of non-limiting examples, the light generator can provide variable wavelengths of light. In one embodiment, the light generator is a broad-band source. In another embodiment, the light generator is a tunable source.

The switchable light source can include K (=1, 2, 3 ...) inputs and N output.

In some embodiments, the number of outputs will be equal to the number of excitation waveguides in the sensing substrate of the system. In a particular embodiment, the interface between a light generating source and the switchable light source inputs includes optical fibers. The interface between the switchable light source outputs should match, in terms of pitch, the excitation waveguides in the sensing substrate to allow these two elements to butt-couple and transfer light from the switchable light source to the excitation waveguides of the sensing substrate.

In one embodiment the optical switch includes individual switching elements based on Mach Zehnder interferometers.

The switchable light source input can include an array of light generator elements. In one implementation, the light generator elements are light emitting diodes (LED). In another implementation the light generator elements are laser chips. Each individual light generator element is separately controlled and can be turned on or off as desired. In one implementation the switchable light source input includes 10 or more light generator elements. In another implementation the switchable light source input includes 100 or more light generator elements. In yet another implementation the switchable light source input includes 1000 or more light generator elements. In a particular implementation the switchable light source input includes between 10 and 100 light generator elements.

The detector array can include an array of detector elements. In one implementation, the detector elements are PIN diodes. In another implementation the detector elements are Avalanche Photo-Diodes (APD). Each individual detector element is separately controlled and read. In one implementation the detector array includes 10 or more detector elements. In another implementation the detector array includes 100 or more detector elements. In yet another implementation the detector array includes 1000 or more detector elements. In a particular implementation the detector array includes between 10 and 100 detector elements.

The switchable light source and detector array can include light manipulating elements such as dispersive elements, filters, switches, modulators, splitters, combiners, mirrors and circulators.

The control of the switchable light source and detector array can be either integrated on the same chip as the light generator elements, detector elements and waveguides or alternatively can be external to the chip. The switchable light source input and detector array can have an electrical interface to an external driver or external controller or logic interface to an external control system. The control of the switchable light source and detector array allows driving each light generator element and detector array separately. It further allows control of the other features present on the switchable light source and detector array such as, for example, the modulators and switches.

The switchable light source and detector array can couple to the substrate in several different ways. In one implementation the coupling is done by bringing the ends of the waveguides on two chips (the switchable light source and the substrate) in close proximity and allowing the light to couple directly from one waveguide to the other. In another implementation, a portion of the waveguides on both chips are aligned on top of each other, parallel and in close proximity to each other, thus coupling light from one waveguide to the other through the evanescent electromagnetic field.

Additional elements useful in planar lightwave circuits, including but are not limited to dispersive elements, couplers, filters, mirrors, circulators, splitters, modulators, switches and trenches are envisioned as part of the system described herein (not shown). Such elements when integrated into the substrate or into the switchable light source and detector array can serve to manipulate the incoming first light waves in the in-coupling waveguides or outgoing second light waves in the out-coupling waveguides.

In one non-limiting example, the detector is a detector array having a spectral range of between 400 to 1000 nm, a photosensitivity (A/W) of >0.3, an active area per element of $0.005$ $mm^2$, 128 elements, and a pitch of <0.1 mm.

In one embodiment, the detector is a silicon photodiode (PN, PIN or APD) array. An example of a suitable detector array is the Hamamatsu S8550 4×8 Silicon APD array.

In general, in one aspect a scanning sensor system for sequencing a nucleic acid is provided. The system includes a substrate (e.g., as illustrated in FIG. 1) that includes a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection region at each crossing; a plurality of optical sensing sites arranged in optical communication with the intersection regions; one or more switchable light sources coupled to and in optical communication with the excitation waveguides of the substrate, and including a scanning light source input and a photo-cleaving light source input; a light dispersive module coupled to and in optical communication with the collection waveguides of the substrate, and including an array of elements; a detector coupled to and in optical communication with the light dispersive module.

In one embodiment the scanning light source is coupled to a first switchable light source coupled to and in optical communication with the excitation waveguides at a first side of the substrate and a photo-cleaving light source coupled to a second switchable light source coupled to and in optical communication with the excitation waveguides at a second side of the substrate.

In general, in a further aspect a scanning sensor system for sequencing a nucleic acid includes a substrate including a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection region at each crossing; a plurality of optical sensing sites arranged in optical communication with the intersection regions; a switchable light source in optical communication with the excitation waveguides, and including a scanning light source input; a photo-cleaving light source and light delivery system arranged external to the substrate (e.g., as illustrated in FIG. 2C); a light dispersive module coupled to and in optical communication with the collection waveguides of the substrate, and comprising an array of elements; a detector coupled to and in optical communication with the light dispersive module.

The light delivery system can include a photo-cleaving light source input.

The dispersive module can be configured to disperse light from one or more of the collection waveguides to a plurality of elements in the detector. In one embodiment the dispersive module is configured to disperse light from a given collection waveguide to four or more elements in the detector. In a particular embodiment the dispersive module disperses light to four elements in the detector. In a different embodiment, the dispersive module disperses light five or more elements in the detector.

Light dispersed from the dispersive module can include a plurality of light wavelengths. In one embodiment the plurality of wavelengths includes four or more light wavelengths. In another embodiment the plurality of wavelengths includes five or more wavelengths.

The photo-cleaving light source can emit light having a wavelength ranging between 400 nm and 2000 nm. The photo-cleaving light source input can be coupled to an ultra-violet light source. In one embodiment the ultra-violet light source emits light having a wavelength ranging between 100 nm and 400 nm.

Control System

A control system for managing the different steps of operating the scanning sensing system is envisioned.

The control system can manage steps such as alignment of the light source, dispersive module, and detector array, and sensing substrate, in addition to switching the light in the switchable light source, reading the detector array and reporting the results detected. The control system which can include a logic device, can also manage and control the sample delivery system and other fluidic or mechanical features used in conjunction with the scanning sensing system as described herein.

Sequencing by Phased Synthesis

Using the optical scanning sensing systems described herein methods for sequencing nucleic acids are enabled.

Following manufacture of the substrate of the scanning sensing system as shown, for example in FIG. 1, either nucleic acid, template, primers, sequencing adaptors, and/or polymerase can be immobilized to the optical sensing sites of the substrate.

Figure 8A:
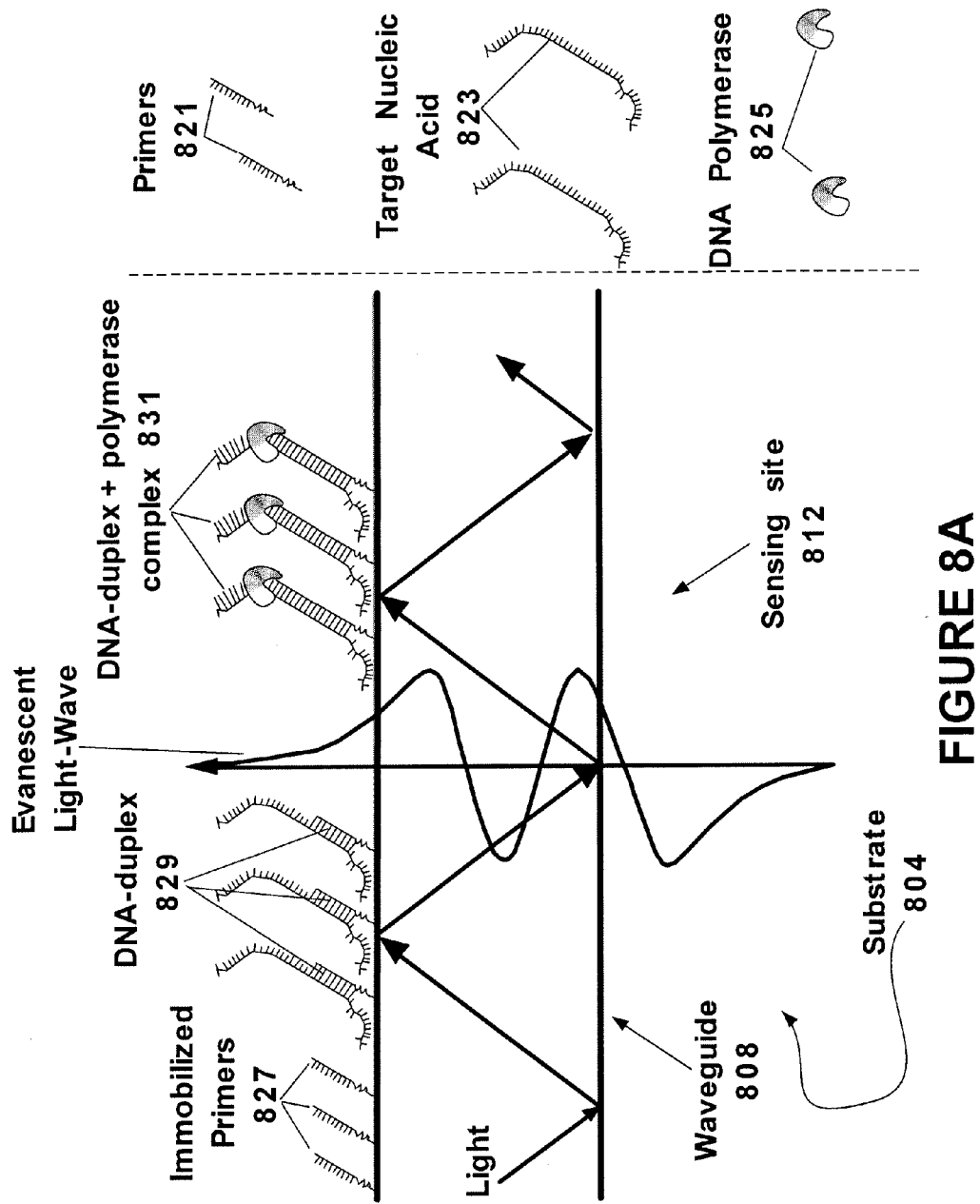
FIG. 8A is an illustration of nucleic acid sequencing by phased synthesis according to one embodiment of the invention including a substrate with immobilized primers at a sensing site of a waveguide, DNA duplex and DNA duplex+polymerase complex.

In one embodiment, depicted in FIG. 8A, DNA primers 821 are immobilized via their 5' end to one or more of the sensing sites 812 of substrate 804 by a covalent immobilization method including, but not limited to, using (3-glycidyloxypropyl)trimethoxysilane (GOPTS), (3-aminopropyl)triethoxysilane, or (3-mercaptopropyl)trimethoxysilane. As an example, substrate 804 can be first coated with GOPTS and deoxyoligonucleotides are covalently coupled to the GOPTS epoxy group via a primary amino group located at the 5' end of the deoxyoligonucleotide. In a particular embodiment, the amino group is spaced 0.5 to 5 nm from the 5' phosphate group of said deoxyoligonucleotide using a spacer arm. Prior to the sequencing process, one or more nucleic acid targets 823 (either RNA or DNA) complementary to one or more of the immobilized DNA primers 827 is added to substrate 804, along with a polymerase enzyme 825 such as reverse transcriptase or DNA polymerase. Target and primer are allowed to hybridize, thereby creating a duplex 829 either ahead of time or just prior to the sequencing process. The polymerase 825 can be added at the same time as the target nucleic acid or just before sequencing. Multiple targets can be sequenced on a single substrate by immobilizing a unique target-specific primer sequence to each of two or more different sensing sites. Immobilizing unique and different target-specific primers to one or more sensing site 812 can be accomplished via the use a high resolution spotting device based on technologies such as microfluidics and pin-spotting or by synthesizing the primers on the spot.

Neutravidin or strepavidin can be immobilized to the sensing site 812 in some embodiments either by physical adsorption, covalent coupling, for example, to a GOPTS coated sensing site, or non-covalent coupling with a biotin-spacer-amine (e.g. Pierce's EZ-link Amine-PEO-biotin or pentylamine-biotin). Primers can then be 5' biotinylated via the same sort of spacer arm discussed above.

Figure 8B:
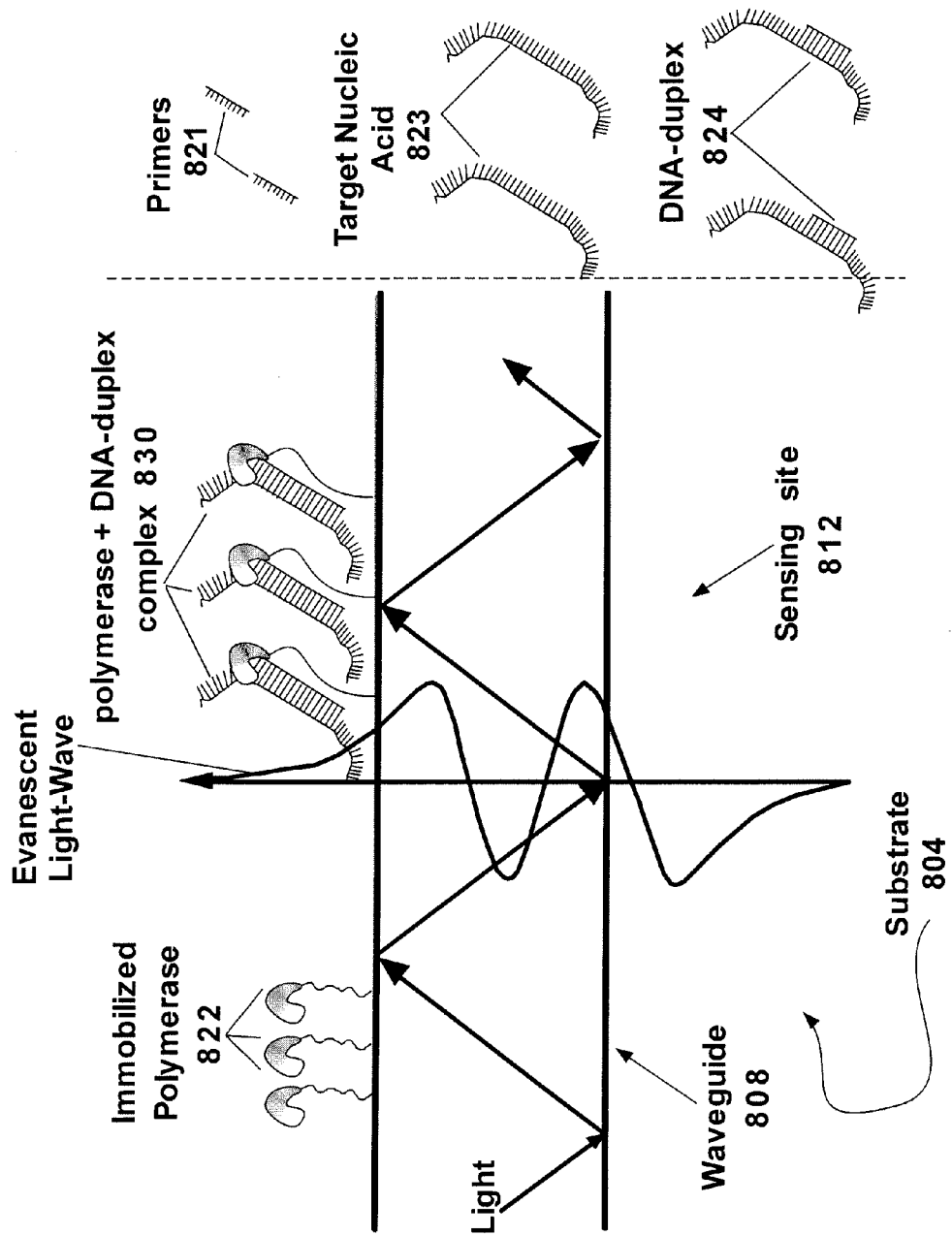
FIG. 8B is an illustration of nucleic acid sequencing by phased synthesis according to another embodiment of the invention including a substrate with immobilized polymerase at a sensing site of a waveguide, DNA duplex and polymerase+DNA duplex complex.

In another embodiment, schematically shown in FIG. 8B, the polymerase enzyme 822 is immobilized at sensing sites 812 of substrate 804. Immobilization can be arranged ahead of time or just before the sequencing process. The DNA primers 821 and the target nucleic acids can be hybridized as a DNA duplex 824 before being added to substrate 804, or they can be added separately to substrate 804 and allowed to hybridize on a surface of substrate 804 (e.g., at sensing site 812). The DNA duplex 824 can then complex with immobilized polymerase 822 at one or more sensing site 12 as a polymerase and DNA duplex complex 830.

Figure 8C:
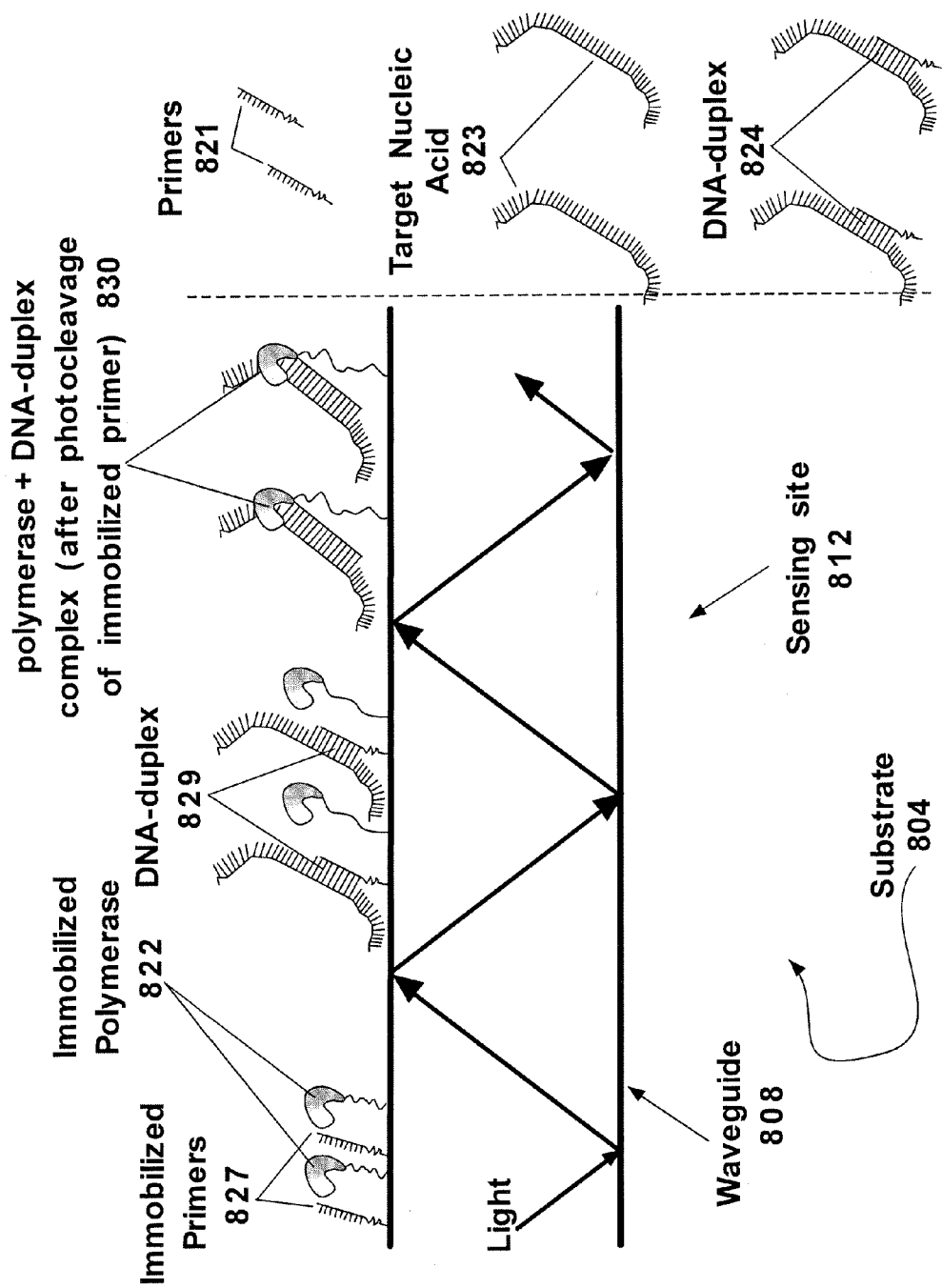
FIG. 8C is an illustration of nucleic acid sequencing by phased synthesis according to another embodiment of the invention including a substrate with immobilized polymerase and immobilized primers at a sensing site of a waveguide, DNA duplex and polymerase+DNA duplex complex after photocleavage of immobilized primer.

In yet another embodiment, depicted in FIG. 8C, multiple targets can be sequenced on a single substrate 804 by a unique target-specific immobilized primers 827 at each of two or more different sensing sites 812. Immobilized primers 827 can be attached to a sensing site 812 via a photocleavable linker. Immobilizing unique and different target-specific primers to one or more sensing site 812 can be accomplished using a high resolution spotting device based on technologies such as microfluidics and pin-spotting or by synthesizing them on the spot. Next, the polymerase enzyme 822 can be immobilized to one or more sensing site 812 proximally to the target-specific immobilized primers 827. Target nucleic acids 823 can then be added to a surface of the substrate 804 and allowed to hybridize and create nucleic acid duplexes 829 with the different immobilized primers 827. Immediately before sequencing, a pulse of light from the photo-cleaving source is delivered to all sensing sites to release the DNA duplexes from the substrate, enabling them to bind to the immobilized polymerase, at one or more sensing sites (not shown).

U.S. Pat. No. 7,145,019 to Olejnik et al. discloses a family of photocleavable linkers that can be incorporated into synthetic nucleotides depicted in FIG. 8C. As disclosed by Olejnik et al., useful linkers (photoreactive groups) for the present methods can include a chemical group (e.g., biotin or an amino group) capable of forming one or more covalent bonds with a substrate which can be cleaved with electromagnetic radiation. These bonds may be formed with a chemical group on the substrate such as, for example, an amine, phenol, imidazole, aldehyde, carboxylic acid or thiol. The photoreactive agent can be a substituted aromatic ring containing at least one polyatomic group and, optionally, one or more monoatomic groups. The aromatic ring in one embodiment is a five or six-membered ring. The substitutions comprise the polyatomic and optional monoatomic groups. The polyatomic group imparts electron channeling properties to attract or repel electrons to certain locations within the chemical structure, thereby creating or establishing the conditions to create the selectively cleavable covalent bonds. Some monoatomic groups such as halides can adjust the frequency or wavelength of the electromagnetic radiation which will induce cleavage. As such, monoatomic groups fine tune the cleavage event to sensitize conjugates to predetermined frequencies or intensities of radiation.

It should be noted that even though the following sequencing process is described for a single target/primer hybrid, it applies to any number of identical or distinct nucleic acid strands bound and sequenced at a single sensing site or at multiple sensing sites. The number of target/primer hybrids per sensing site can be anything between 1 and $>10^9$. Suitable polymerases include those described herein regarding nucleic acid amplification (e.g., DNA polymerase and reverse transcriptase).

The next step in the sequencing process includes delivering a 'master mix' containing all reagents needed for the polymerase enzyme to extend the nucleic acid primers of DNA duplexes 829 immobilized at sensing sites 812. Said delivery can be done using one of the sample delivery systems described above. This 'master mix' includes predetermined concentrations of the four nucleotides (dNTP) each type labeled with a different fluorescent tag emitting light at a different wavelength. All fluorescent tags are attached to the corresponding nucleotide through a photo-cleavable chemical bond, so that the tag can be released and washed away after each new added base is identified ("called"), thereby preventing the accumulation of multicolored tags at the sensing site during sequencing.

The sequencing reaction can also be synchronized using a photocleavage event.

In one embodiment, the fluorescent tags are designed to be large enough to inhibit further extension once added by the polymerase enzyme to the nucleic acid primer. In another embodiment, the fluorescent tags are a standard fluorescent dye, too small to inhibit the polymerase, but the 3' OH group of each of the fluorescently labeled dNTPs is blocked with a photocleavable cage also referred to herein as a "blocking group". Caged nucleotides have a cage structure at their 3' OH group. The cage structure is a removable blocking group which prevents the 3' OH group from participating in nucleotide addition reactions. Caged nucleotides are useful in primers and probes for use in sequencing reactions as described herein. Many cage structures are known. Exemplary of cage structures are photolabile structures which allow their removal by exposure to light. Particular cage structures useful for reversibly blocking the 3' OH group are described in U.S. Pat. No. 6,632,609; Metzker et al., *Nucleic Acids Res.* 22:4259-4267 (1994); Burgess and Jacutin, *Am. Chem. Soc.* Abstracts volume 221, abstract 281 (1996); Zehavi et al., *J. Organic Chem.* 37:2281-2288 (1972); Kaplan et al., *Biochecm.* 17:1929-1035 (1978); McCray et al., *Proc. Natl. Acad. Sci. USA* 77:7237-7241 (1980); and Pillai, *Synthesis* 1-26 (1980). Useful examples of photo-cleavable cage structures include 2'-deoxy-3'-O-(2-nitrobenzyl) derivatives, 2'deoxy-3'-O-(2-aminobenzoyl) derivatives, 2'deoxy-3'-O-(4-nitrobenzoyl) derivatives (Metzker et al., *Nucleic Acids Res.* 22:4259-4267 (1994)).

Useful cage structures include those based using nitrophenyl groups. Several different nitrophenyl derivatives that can be useful cages are described in U.S. Pat. No. 5,872,243 to Gee et al. For example, Gee et al. describe a caging group that is a derivative of o-nitroarylmethine having the formula:

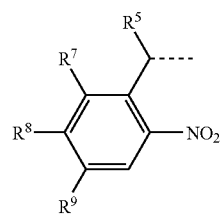

where $R^5$ is one of H, $CH_3$, or $CO_2R^6$, where $R^6$ is H, an alpha-acyloxyalkyl ester having 3-6 carbons, a t-butyl group or an alkali metal. $R^7$ is one of H or $NO_2$. $R^8$ and $R^9$ are independently H, alkoxy having 1-6 carbons, $-O(CH_2)_n$ $CO_2R^{10}$ (where n=1-18 and $R^{10}$ is H or alkyl having 1-6 carbons) or $R^8$ taken in combination with $R^9$ is methylenedioxy ($-O-CH_2-O-$). Caging moieties that are alpha-carboxy nitroarylmethines (compounds wherein $R^5$ is $CO_2R^6$) have been previously described in U.S. Pat. No. 5,635,608 to Haugland et al. (1997). Gee et al. further disclosed that alternatively $R^5$ is $CH_3$ and $R^7$ is H. Additionally, $R^8$ and $R^9$ can each be methoxy.

Gee et al. also disclosed that the photolabile caging group can be a 2-methoxy-5-nitrophenyl having the formula:

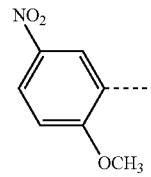

Additionally, Gee et al. disclosed that the photolabile caging group can be a derivative of desyl having the formula:

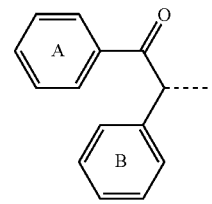

Aromatic rings A and B are optionally and independently substituted one or more times by halogen, $-NO_2$, $-OR^{11}$, and $-NR^{12}R^{13}$ where $R^{11}$, $R^{12}$ and $R^{13}$ are independently alkyl groups having 1-6 carbons. Preferably there are no more than two non-hydrogen substituents on each of rings A and B. It is envisioned that any one or more of the cage structures described by Gee et al. can be used in conjunction with the systems and methods described herein.

Synchronization of the first primer extension event is probably the most critical because it involves independent formation of several different molecular complexes including the primer/target duplex, the duplex/polymerase complex, and the fluorescently labeled dNTP/polymerase complex, while only the last of these is required for synchronization of subsequent extension events. In one embodiment, signal from the first extension event is monitored until it reaches steady-state in the plurality of sensing sites, at which time a pulse of light from the photo-cleaving source is delivered to all sensing sites to initiate the second extension event. In another embodiment, the first initiation event is synchronized by jumping temperature above the "melting temperatures" of the aforementioned complexes, followed immediately by a "snap cool" to 40-65° C. The timing of the temperature jump and snap cool can be controlled to limit diffusion of primer, target, polymerase, and fluorescently labeled dNTPs to within a given sensing site. This will both limit crosstalk between sensing sites, and also ensure that the aforementioned complexes will reform rapidly. As in the previous embodiment, signal from the first extension event is monitored until it reaches steady-state in the plurality of sensing sites, at which time a pulse of light from the photo-cleaving source is delivered to all sensing sites to initiate the second extension event.

In another embodiment, all phased sequencing strategies described herein are performed using adaptors instead of conventional primers (Hutchison, *Nucleic Acids Res.* 35:6227-6237 (2007)). Here, the target nucleic acid is fragmented into smaller pieces using a nuclease. Next, the adaptor molecule is ligated to the 5' end of the fragments. The adaptor molecules have one or more sequences that are recognized by complementary capture probes in the sensing sites on the substrate, thus permitting the capture of the fragments. The captured fragments are then amplified in the sensing sites before sequencing in order to give enough identical target fragments for phased sequencing. By way of a non-limiting example, the method of amplification can be by bridge amplification. The target fragments are then sequenced by phased sequencing by any of the strategies described herein.

Figure 9:
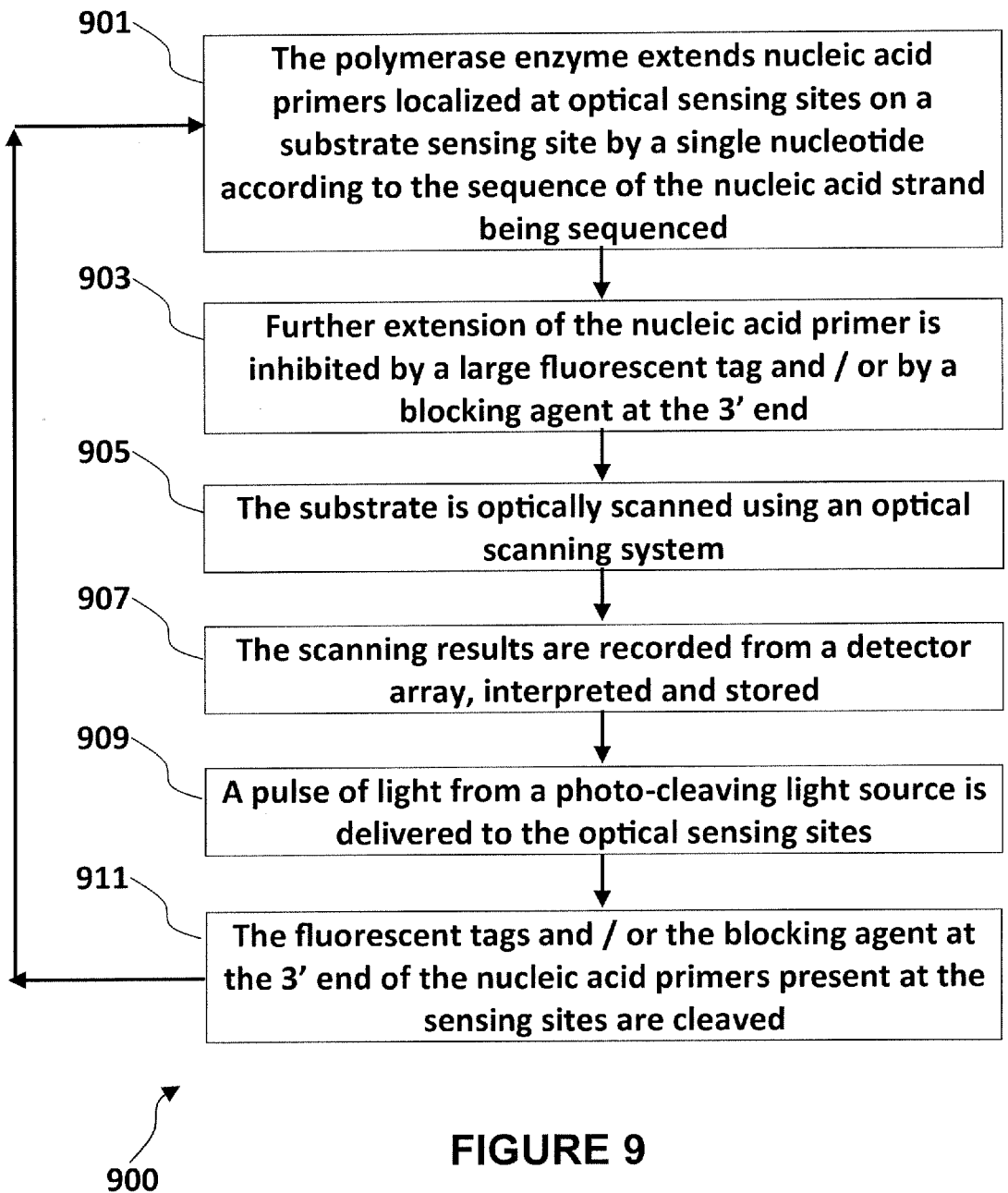
FIG. 9 is a flow chart illustrating of one embodiment of the sequencing by phased synthesis process of the invention.

The sequencing process is summarized in the flow chart of FIG. 9. As indicated, algorithm 900 represents a cyclic process for obtaining a nucleic acid sequence. In step 901, the polymerase enzyme extends nucleic acid primers localized at optical sensing sites on a substrate by a single nucleotide according to the sequence of the nucleic acid strand being sequenced. As shown in step 903, further extension of the nucleic acid primer is inhibited by a fluorescent tag (e.g., a large bead with multiple fluorescent tags or a bulky or large molecule like BODIPY® fluorophores (U.S. Pat. No. 5,614,386 and U.S. Pat. No. 5,728,529)) attached to the base (e.g. via a photocleavable amino allyl linkage (U.S. Pat. No. 7,057,031) or by a photocleavable blocking agent at the 3' end of the nucleic acid strand being extended. Next, as shown in step 905, the substrate is optically scanned using an optical scanning system. In step 907 the scanning results are recorded from a detector array, interpreted and stored. In step 909, a pulse of light from a photo-cleaving light source is delivered to the optical sensing sites. Next, in step 911 the fluorescent tags and/or the blocking agent at the 3' end of the nucleic acid primers present at the optical sensing sites are cleaved. As shown, next the process can cycle back to step 901. The process can be repeated in a cycle repeatedly as needed to complete the desired sequencing of the nucleic acid strand. In each such round, the nucleic acid primer can be extended by a single base.

In one embodiment, one or more sensing site includes multiple copies of the same nucleic acid primer. Thus each copy will be adding the same nucleotide on the same round. The scanning sensing system reveals the newly added base by the color of the read at each sensing site. Four different dye colors, each corresponding to a different dNTP can be mapped by the dispersive module and the N collection waveguides into the 1D or 2D (e.g. 4×N) detector array. The rate (K) of adding dye-labeled dNTPs to the nucleic acid primer depends mainly on the binding rate of the polymerase enzyme and the photocleavage rate of fluorescent tag and/or the blocking group, for example, a 3' caged OH group, and can reach a thousand or more nucleotides per second. In a non-limiting example, K can be 1 or more, 5 or more, 10 or more, 20 or more, 50 or more, 75 or more 100 or more, 200 or more, 250 or more, 500 or more and even 1000 or more nucleotides per second.

By binding different nucleic acid primers to each of the L sensing sites a total of K*L nucleotides can be sequenced per second per chip. The sequencing process can proceed as long as a 'large enough number' of the sequenced nucleic acid complexes remains in phase with each other. It is envisioned that this 'large enough number' can be about 25% of the total number of nucleic acid complexes in a given sensing site.

In another embodiment, a single nucleic acid primer is immobilized at a given sensing site. Using the single molecule detection capabilities of the system it will be possible to detect the signal from a given sensing site and use four color dNTP coding for inferring the sequence of the synthesized nucleic acid at the site. Read lengths of 1 or more, 5 or more, 10 or more, 20 or more, 30 or more, 40 or more, 50 or more, 60 or more, 70 or more, 80 or more, 90 or more, 100 or more, 200 or more, 300 or more, 500 or more, 600 or more, 700 or more, 800 or more, 900 or more, and even 1 kb or more bases are envisioned.

A number of polymerase blocking strategies to achieve phase sequencing are envisioned. Tcherkassov in U.S. patent application Ser. No. 10/491,557 (published as US 2005/0227231 on Oct. 13, 2005) disclosed using a fluorescent dye attached to a dNTP (via the base) as both a tag and a stearic blocking group to stall the polymerase during a sequencing reaction. The systems and methods of some embodiments of the present invention optionally follow a similar approach wherein a fluorescent dye is used to stall a polymerase. Accordingly, the fluorescent dye itself can be attached to the nucleotide base via a photocleavable linkage as described herein.

Alternatively, a dendrimer containing multiple fluorescent dyes attached to the nucleotide base via a photocleavable linkage can be used to stall a polymerase. In another embodiment a bead containing multiple fluorophores attached to the nucleotide base via a photocleavable linkage can be used. In a further embodiment a quantum dot can be attached to the nucleotide base via a photocleavable linkage.

Sample Delivery System

Delivery of the sample containing the nucleic acid strands to be sequenced and all other required reagents to the sequencing platform can be achieved in a number of different ways. In one embodiment a flow-cell can be attached to the substrate from above. The flow-cell can include inlet and outlet tubes connected thereto and optionally an external pump can be used to deliver the sample or reagents to the flow-cell and across the substrate (not shown).

In another embodiment a microfluidic system is built into the substrate or externally attached on top of the substrate, for example, as described in U.S. Patent Application Ser. No. 60/971,878 filed Sep. 12, 2007.

In yet another advantageous embodiment, an open gasket can be attached to the top of the substrate and the sample and reagents can be injected into the gasket (not shown). Suitable gasket materials include, but are not limited to, neoprene, nitrile, and silicone rubber. A further embodiment is a water-tight reaction chamber formed by a gasket sandwiched between the substrate and a chemically inert, water resistant material such as, but not limited to, black-anodized aluminum, thermoplastics (e.g., polystyrene, polycarbonate, etc), glass, etc.

In general, in one aspect a method of sequencing a nucleic acid by detecting the identity of a fluorescent nucleotide analogue incorporated at the 3' end of a growing nucleic acid strand is provided. The method includes the steps of (a) immobilizing a plurality of complexes comprising a template nucleic acid, a primer configured to hybridize to the template and a polymerase, at a plurality of optical sensing sites of a substrate, wherein the substrate is part of a waveguide-based optical scanning system; (b) extending the primer by a single nucleotide with the polymerase and one or more fluorescent nucleotide analogues using a polymerase extension reaction, wherein each type of fluorescent nucleotide analogue includes a unique fluorescent tag optionally configured to inhibit further primer extension and/or a blocking agent at the 3' end and wherein incorporation of the fluorescent nucleotide analogue reversibly terminates the polymerase extension reaction; (c) detecting the unique tag of the fluorescent nucleotide analogue by optically scanning the substrate using the optical scanning system to identify the fluorescent nucleotide analogue incorporated by the polymerase reaction; (d) recording the results of the optical scanning of the substrate; (e) reversing the termination of the polymerase extension reaction by providing a photo-cleaving pulse of light to one or more of the optical sensing sites of the substrate to cleave the fluorescent tag or the blocking agent; and (f) repeating steps (b) through (e).

The primer in one embodiment is immobilized at the plurality of optical sensing sites prior to formation and immobilization of the plurality of complexes. In a particular embodiment the primers are covalently immobilized at the optical sensing sites. In another embodiment the primers are immobilized using a photo-cleavable linker at the optical sensing sites.

The polymerase in one embodiment is immobilized at the plurality of optical sensing sites prior to formation and immobilization of the plurality of complexes. In a specific embodiment the polymerases are covalently immobilized at the optical sensing sites prior to immobilizing the plurality of complexes.

In one embodiment of the method step (b) is performed before step (c) without a washing step between steps (b) and (c). In another embodiment of the method step (f) further includes performing step (e) before repeating step (b) without a washing step between steps (e) and (b).

The nucleic acid being sequenced can be DNA.

In one embodiment the primers are immobilized using a photo-cleavable linker at the optical sensing sites and the polymerases are covalently immobilized at the optical sensing sites prior to formation and immobilization of the plurality of complexes. In a related embodiment prior to step (b) immobilized primer and template duplexes are formed, and a photo-cleaving pulse of light is provided to cleave the photo-cleavable linker and release the duplexes, wherein the released duplexes subsequently bind to the immobilized polymerases and form the immobilized plurality of complexes.

The fluorescent nucleotide analogs can include four different dNTPs, wherein each dNTP is labeled with a different fluorescent tag. In a particular embodiment the fluorescent tags are attached to the dNTPs through a photo-cleavable chemical bond.

In general, in another aspect a method of sequencing a single nucleic acid molecule by detecting the identity of a fluorescent nucleotide analogue after the nucleotide analogue is incorporated into a growing nucleic acid strand is provided. The method includes the steps of (a) immobilizing a complex comprising a template nucleic acid, a primer configured to hybridize to the template and a polymerase, at an optical sensing sites of a substrate, wherein the substrate is part of a waveguide-based optical scanning system; (b) extending the primer by a single nucleotide with the polymerase and one or more fluorescent nucleotide analogues using a polymerase extension reaction, wherein each fluorescent nucleotide analogue comprises a fluorescent tag optionally configured to inhibit further primer extension and/or a blocking agent at the 3' end of the nucleotide analog and wherein incorporation of the fluorescent nucleotide analogue terminates the polymerase extension reaction; (c) detecting the unique label attached to the fluorescent nucleotide analogue by optically scanning the substrate using the optical scanning system to identify the fluorescent nucleotide analogue incorporated by the polymerase reaction; (d) recording the results of the optical scanning of the substrate; (e) providing a photo-cleaving pulse of light to one or more of the optical sensing sites of the substrate to cleave the fluorescent tag and/or the blocking agent; and (f) repeating steps (b) through (e).

The primer can be immobilized at the plurality of optical sensing sites prior to formation and immobilization of the complex. In a particular embodiment the primer is covalently immobilized at the optical sensing sites. In another embodiment the primer is immobilized using a photo-cleavable linker at the optical sensing sites.

The polymerase can be immobilized at the plurality of optical sensing sites prior to formation and immobilization of the complex. In one embodiment the polymerase is covalently immobilized at the optical sensing sites prior to immobilizing the complex.

In one embodiment of the method step (b) is performed before step (c) without a washing step between steps (b) and (c). In another embodiment of the method step (f) further includes performing step (e) before repeating step (b) without a washing step between steps (e) and (b).

The nucleic acid being sequenced can be DNA.

In a particular embodiment of the method the primer is immobilized using a photo-cleavable linker at the optical sensing sites and polymerase is covalently immobilized at the optical sensing sites prior to formation and immobilization of the complex. In one embodiment prior to step (b) immobilized primer and template duplexes are formed, and a photo-cleaving pulse of light is provided to cleave the photo-cleavable linker and release the duplexes, wherein the released duplexes subsequently bind to the immobilized polymerase and form the immobilized complex.

The fluorescent nucleotide analogs can include four different dNTPs, wherein each is labeled with a different fluorescent tag. In one embodiment the fluorescent tags are attached to the dNTPs through a photo-cleavable chemical bond.

In practicing the methods of the present invention, many conventional techniques in molecular biology are optionally utilized. These techniques are well known and are explained in, for example, Ausubel et al. (Eds.) *Current Protocols in Molecular Biology, Volumes I, II, and III*, (1997), Ausubel et al. (Eds.), *Short Protocols in Molecular Biology: A Compendium of Methods from Current Protocols in Molecular Biology*, 5th Ed., John Wiley & Sons, Inc. (2002), Sambrook et al., *Molecular Cloning: A Laboratory Manual*, 3rd Ed., Cold Spring Harbor Laboratory Press (2000), and Innis et al. (Eds.) *PCR Protocols: A Guide to Methods and Applications, Elsevier Science & Technology Books* (1990), all of which are incorporated herein by reference.

Sample preparation suitable for use with the system and methods described herein can include any of a number of well know methods for collection and analysis of biological and/or environmental samples. In the case of biological samples the sample can be, for example, manipulated, treated, or extracted to any desired level of purity for a target of interest.

The sample can be bodily fluids suspected to contain a target nucleic acid. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

It is anticipated that the systems described herein can be used for screening for example, nucleic acid templates from a large variety of samples. In the case where the investigated subject is a living creature, the sample may originate from body fluids as discussed. Methods of obtaining samples include but are not limited to cheek swabbing, nose swabbing, rectal swabbing, skin fat extraction or other collection strategies for obtaining a biological or chemical substance. When the tested subject is a non-living or environmental body, the sample may originate from any substance in a solid phase, liquid phase or gaseous phase. The sample may be collected and placed onto the sensing substrate or the sensing substrate may be directly exposed to the investigated sample source (e.g. water reservoir, free air) and interact with it.

In some embodiments, the bodily fluids are used as a source of nucleic acids present therein. Where desired, the bodily fluids can be pre-treated before performing the analysis with the subject scanning sensing devices. The choice of pre-treatments will depend on the type of bodily fluid used and/or the nature of the nucleic acid under investigation. For instance, where the target nucleic acid is present at low level in a sample of bodily fluid, the sample can be concentrated via any conventional means to enrich the target nucleic acid. Methods of concentrating a target nucleic acid include but are not limited to drying, evaporation, centrifugation, sedimentation, precipitation, concentration with magnetic beads, and amplification. The target nucleic acid can also be extracted using various lytic enzymes or chemical solutions according to the procedures set forth in Sambrook et al. ("Molecular Cloning: A Laboratory Manual"), or using nucleic acid binding resins following the accompanying instructions provided by manufactures.

In some embodiments, pretreatment can include diluting and/or mixing the sample, and filtering the sample to remove, e.g., red blood cells from a blood sample.

In one embodiment, the target is a nucleic acid that is DNA, for example, cDNA. In a related embodiment, the DNA target is produced via an amplification reaction, for example, by polymerase chain reaction (PCR).

The target nucleic acid can be single-stranded, double-stranded, or higher order, and can be linear or circular. Exemplary single-stranded target nucleic acids include mRNA, rRNA, tRNA, hnRNA, miRNA, ssRNA or ssDNA viral genomes, although these nucleic acids may contain internally complementary sequences and significant secondary structure. Exemplary double-stranded target nucleic acids include genomic DNA, mitochondrial DNA, chloroplast DNA, dsRNA or dsDNA viral genomes, plasmids, phage, and viroids. The target nucleic acid can be prepared synthetically or purified from a biological source. The target nucleic acid may be purified to remove or diminish one or more undesired components of the sample or to concentrate the target nucleic acids. Conversely, where the target nucleic acid is too concentrated for the particular assay, the target nucleic acid may be diluted.

Following sample collection and optional nucleic acid extraction, the nucleic acid portion of the sample comprising the target nucleic acid can be subjected to one or more preparative reactions. These preparative reactions can include in vitro transcription (IVT), labeling, fragmentation, amplification and other reactions, such as a pre-processing step before amplification for the amplification and detection of miRNA (e.g., use of the Ambion's mirVana™ miRNA Isolation Kit). mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target nucleic acid. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target nucleic acid is single-stranded, the first cycle of amplification forms a primer extension product complementary to the target nucleic acid. If the target nucleic acid is single stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment.

The target nucleic acid can be amplified by contacting one or more strands of the target nucleic acid with a primer and a polymerase having suitable activity to extend the primer and copy the target nucleic acid to produce a full length complementary nucleic acid or a smaller portion thereof. Any enzyme having a polymerase activity that can copy the target nucleic acid can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB D DNA polymerases; RNA polymerases such as *E. coli*, SP6, T3 and T7 RNA polymerases; and reverse transcriptases such as AMV, M MuLV, MMLV, RNAse H MMLV (Superscript®), Superscript® II, ThermoScript®, HIV 1, and RAV2 reverse transcriptases. All of these enzymes are commercially available. Exemplary polymerases with multiple specificities include RAV2 and Tli (exo) polymerases. Exemplary thermostable polymerases include Tub, Taq, Tth, Pfx, Pfu, Tsp, Tfl, Tli and *Pyrococcus* sp. GB D DNA polymerases.

Suitable reaction conditions are chosen to permit amplification of the target nucleic acid, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot start techniques, use of nested primers, or designing PCR primers so that they form stem-loop structures in the event of primer-dimer formation and thus are not amplified. Techniques to accelerate PCR can be used, for example, centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target nucleic acids or different regions of a particular target nucleic acid within the sample.

Amplified target nucleic acids may be subjected to post amplification treatments. For example, in some cases, it may be desirable to fragment the target nucleic acid prior to hybridization in order to provide segments which are more readily accessible. Fragmentation of the nucleic acids can be carried out by any method producing fragments of a size useful in the assay being performed; suitable physical, chemical and enzymatic methods are known in the art.

A wide diversity of labels are available in the art that can be employed for conducting the subject assays (e.g., sequencing). In some embodiments labels are detectable by spectroscopic, photochemical, biochemical, immunochemical, or chemical means. For example, useful nucleic acid labels include fluorescent dyes, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include enzymes, substrates, cofactors, inhibitors, fluorescent moieties, chemiluminescent moieties, or bioluminescent labels. Labeling agents optionally include, for example, monoclonal antibodies, polyclonal antibodies, proteins, or other polymers such as affinity matrices, carbohydrates or lipids. Detection proceeds by any of the methods described herein, for example, by detecting an optical signal in an optical waveguide. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Preferred labels include labels that produce an optical signal. Thus, a label includes without limitation any composition detectable by spectroscopic, photochemical, biochemical, immunochemical, electrical, optical, thermal, or chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule is covalently bound to a polymer. The ligand then binds to an anti ligand molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include luciferin, and 2,3-dihydrophthalazinediones, such as luminol.

Methods of detecting labels are well known to those of skill in the art. Thus, for example, where the label is a fluorescent label, it may be detected by exciting the fluorochrome with the appropriate wavelength of light and detecting the resulting fluorescence by, for example, a scanning sensor system as described herein. Similarly, enzymatic labels are detected by providing appropriate substrates for the enzyme and detecting the resulting reaction product (e.g., a reaction product capable of producing a detectable optical signal).

In some embodiments the detectable signal may be provided by luminescence sources. Luminescence is the emission of light from a substance for any reason other than a rise in its temperature. In general, atoms or molecules emit photons of electromagnetic energy (e.g., light) when they move from an excited or higher energy state to a lower energy state (usually the ground state); this process is often referred to as radioactive decay. There are many causes of excitation. If the exciting cause is a photon, the luminescence process is referred to as photoluminescence. If the exciting cause is an electron, the luminescence process is referred to as electroluminescence. More specifically, electroluminescence results from the direct injection and removal of electrons to form an electron-hole pair, and subsequent recombination of the electron-hole pair to emit a photon. Chemiluminescence is luminescence which results from a chemical reaction. Bioluminescence is luminescence produced by a living organism. Fluorescence is photoluminescence which is the result of a spin allowed transition (e.g., a singlet-singlet transition, triplet-triplet transition). Typically, fluorescence emissions do not persist after the exciting cause is removed as a result of short-lived excited states which may rapidly relax through such spin allowed transitions. Phosphorescence is a photoluminescence which is the result of a spin forbidden transition (e.g., a triplet-singlet transition). Typically, phosphorescence emissions persist long after the exciting cause is removed as a result of long-lived excited states which may relax only through such spin-forbidden transitions. A luminescent label may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,4-phthalazinedione. A frequently used compound is luminol, which is a 5-amino compound. Other members of the family include the 5-amino-6, 7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

In one embodiment, all in-coupling waveguides are provided with a first light wave and simultaneous detection of second light waves at each out-coupling waveguide is achieved using a detector that is a photodetector array.

By switching light between waveguides, each waveguide can be individually addressed with a first light wave. The order of addressing the waveguides can be sequential, staggered, random or in any order desired. Rapid scanning of the entire array of optical sensing sites can be achieved with the aid of the photodetector array since any second light wave associated with each out-coupling waveguide can be simultaneously detected.

In another embodiment, a single excitation waveguide is provided with a first light wave and simultaneous detection of second light waves at each collection waveguide is achieved using a detector that is a photodetector array. By switching light between excitation waveguides, each individual excitation waveguide can be individually addressed with a first light wave. The order of addressing the excitation waveguides can be sequential, staggered, random or in any order desired. Rapid scanning of the entire two-dimensional array of optical sensing sites can be achieved with the aid of the photodetector array since any second light wave associated with each collection waveguide can be simultaneously detected. For example, where the two-dimensional array is configured as an array of 128 excitation waveguides and 128 collection waveguides, then it would be possible to simultaneously detect second light waves (if any) generated from 128 optical sensor sites after providing a single first lightwave in a first excitation waveguide. Thus, 128 optical sensing sites can be interrogated for presence or absence of target simultaneously. Next, a second excitation waveguide can be excited thereby triggering the interrogation of a second set of 128 optical sensing sites. The process can rapidly be repeated until every excitation waveguide has been excited and the entire array of optical sensing sites have been interrogated.

In various embodiments the method of using the scanning sensing system involves the detection of a substance, including but not limited to a nucleic acid sequence. In a particular embodiment, a single base can be identified in a sequencing process. In another embodiment a single nucleotide polymorphism (SNP) is detected in the target nucleic acid. In one embodiment expression of a gene is detected upon detection of the target nucleic acid.

Fluorescence imaging is sensitive to speed, sensitivity, noise and resolution, and each may be optimized for use in the invention, for example, speed may be decreased to increase assay times. Base extension may be detected using a CCD camera, a streak camera, spectrofluorometers, fluorescence scanners, or other known fluorescence detection devices, which generally comprise four elements, an excitation source, a fluorophore, a filter to separate emission and excitation photons, and a detector to register emission photons and produce a recordable output, typically an electrical or photographic output.

Polymerase enzymes useful in the invention are known in the art and include, but are not limited to, thermostable polymerases, such as pfu, Taq, Bst, Tfl, Tgo and Tth polymerase, DNA Polymerase I, Klenow fragment, and/or T4 DNA Polymerase. The polymerase may be a DNA-dependent DNA polymerase, a DNA-dependent RNA polymerase, a RNA-dependent RNA polymerase, a RNA-dependent DNA polymerase or a mixture thereof, depending on the template, primer and NTP used. The polymerase may or may not have proofreading activity (3' exonuclease activity) and/or 5' exonuclease activity.

The capture molecule and/or the nucleic acid molecule of the invention may be any nucleic acid, including, but not limited to, DNA and/or RNA and modifications thereto known in the art, and may incorporate 5'-O-(1-thio)nucleoside analog triphosphates, .alpha.-thiotriphosphate, 7-Deaza-.alpha.-thiotriphosphate, N6-Me-.alpha.-thiotriphosphate, 2'-O-Methyl-triphosphates, morpholino, PNA, aminoalkyl analogs, and/or phosphorothioate.

It is envisioned that a variety of instrumentation relating to biological or environmental sample preparation, handling and analysis can be used in conjunction with the system and methods described herein. Examples of such instrumentation include but are not limited to a cell sorter, a DNA amplification thermal cycler, or a chromatography machine (e.g., GC or HPLC). Such instrumentation is well known to those skilled in the art. It is envisioned that a robotic interface could be used between the scanning sensing system of the present invention and various instrumentation relating to biological or environmental sample preparation, handling and analysis.

Manufacturing

In general, in another aspect methods of manufacturing a scanning sensing system for sequencing by phased synthesis are provided. In one embodiment the system is a planar lightwave circuit (PLC).

The starting material or substrate for manufacturing PLC devices is a wafer usually made of Silicon (Si) or Silica ($SiO_2$). The most common wafer diameters in use are 4", 6" and 8". The manufacturing process for PLC devices involves two basic processes namely, deposition and etching. A short description of each of them is given below.

In certain embodiments the methods of manufacturing the systems described herein can include, but are not limited to laser writing, UV writing and photonic band-gap waveguide methods. The manufacturing process in some embodiments includes one or more steps of deposition, masking and etching.

Deposition:

In the deposition step a layer of well defined material having well controlled thickness is deposited across the entire wafer. The most common material used for waveguide layer deposition is Silica ($SiO_2$) also known as glass. The optical properties of the Silica (mainly its refractive index) is controlled by the amount of doping (Ge, P, and B etc.) introduced during the deposition. Other materials such as silicon, Silicon Nitride ($Si_3N_4$), glass, epoxy, lithium niobate, indium phosphide and $SiO_xN_y$ (Silicon OxyNitride) and its derivatives are also used. For the cladding layer, materials can include but are not limited to silicon, silica ($SiO_2$), glass, epoxy, lithium niobate and indium phosphide The deposition step is done using several technologies such as PECVD (Plasma-Enhanced Chemical Vapor Deposition), LPCVD (Low Pressure CVD), APCVD (Atmospheric pressure CVD), FHD (Flame Hydrolysis Deposition) and others well known in the art.

Figure 10A:
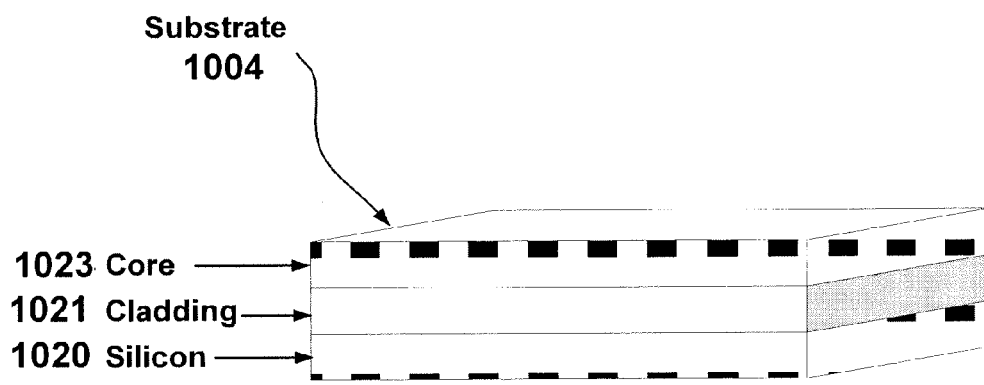
FIGS. 10A-D are schematics illustrating a representative manufacturing process for the substrate and waveguides of the invention.

FIG. 10A illustrates an exemplary substrate 1004 as a schematic structure created after two consecutive deposition steps of a cladding 1021 layer and a core 1023 layer over a silicon 1020 layer, which can be a wafer. As mentioned above, these two layers differ in the refraction index which is achieved by using different levels of doping. Typical thicknesses for the different layers are: Cladding up to about 20 μm and core up to 6 μm. The thickness of the silicon 1020 wafer can range from about 0.5 mm to 1 mm.

Figure 10B:
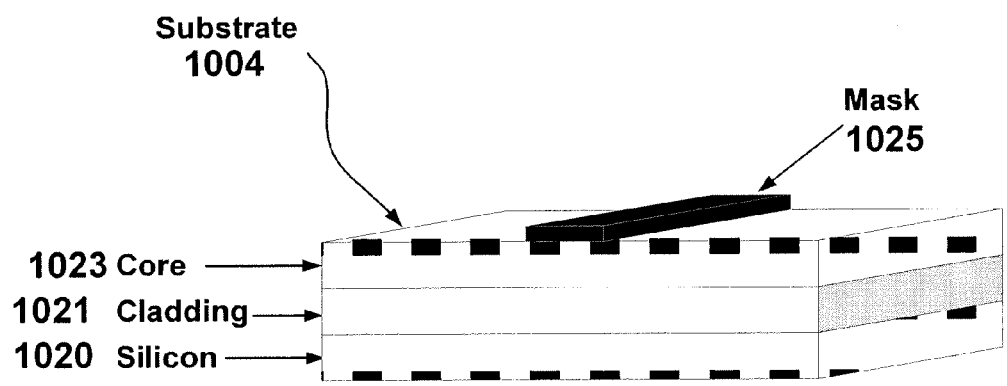

Masking:

Following the deposition and before the etching step, the desired two-dimensional structure of the PLC device is transferred to the deposited wafer by masking the areas not to be etched away. The masking is done in several steps involving covering the wafer with light sensitive material, exposing it to light through lithographic masks and removing the exposed material leaving in place the mask. The result of such steps is shown in FIG. 10B where a mask 1025 is shown on top of the core 1023 layer of the substrate 1004.

Figure 10C:
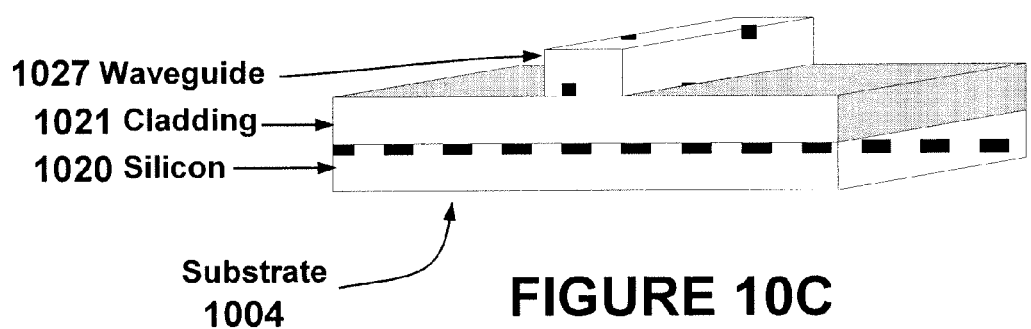

Etching:

In the etching step, material at the un-masked areas is removed from the top core 1023 layer of the substrate (see FIG. 10C). The etching rate is a known parameter, therefore the etching depth can be controlled by time. The two most common techniques for etching are wet-etching and Reactive-Ion-Etching (RIO). FIG. 10C shows the results of the etching step which results in a waveguide 1027.

Figure 10D:
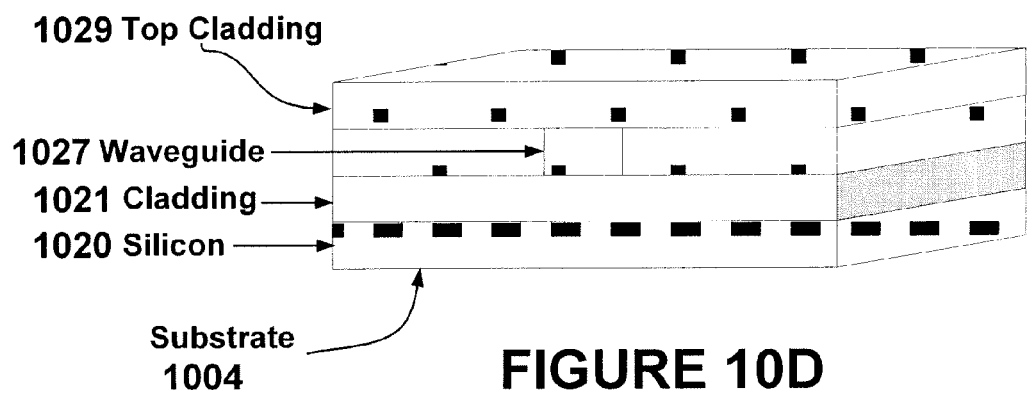

After the etching step, an over-cladding or top cladding 1029 layer is created using a deposition step similar to the one described above. The results are shown in FIG. 10D. As shown in FIG. 10D, the resulting waveguide 1027 can be surrounded by a top cladding 1029 and a cladding 1021 over a silicon 1020 layer.

The above steps can be repeated to create several waveguide layers one on top of the other. In this case, a planarization step may be required between one waveguide layer and the other. This is done using a technique known as Chemical Mechanical Planarization (CMP).

Figure 11:
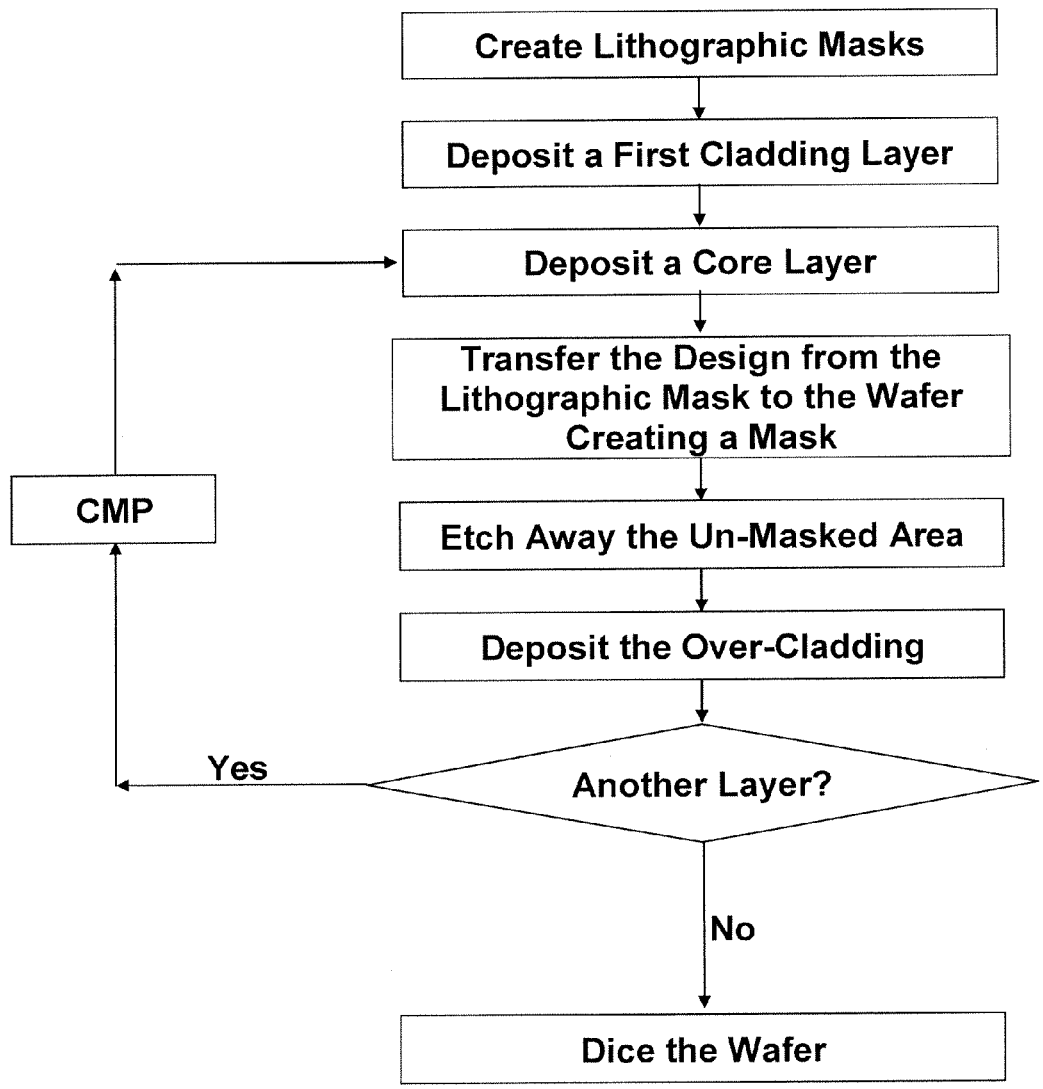
FIG. 11 is a flow chart showing a representative manufacturing process for the substrate.

When the wafer processing is completed, it can be diced into the individual chips. An exemplary simplified flow-chart of the manufacturing process is shown in FIG. 11.

Business Methods

The system and methods described herein may be used in a range of applications including biomedical and genetic research as well as clinical diagnostics. Arrays of polymers such as nucleic acids may be screened for sequence information.

Other applications include chip based genotyping, species identification and phenotypic characterization, as described in U.S. Pat. No. 6,228,575. Still other applications including diagnosing a cancerous condition or diagnosing viral, bacterial, and other pathological or nonpathological infections, are described in U.S. Pat. No. 5,800,992. A further application includes chip based single nucleotide polymorphism (SNP) detection as described in U.S. Pat. No. 6,361,947.

The working system described here can also be a subsystem within a much larger bio-analysis system. The bio-analysis system could include all the aspects of sample preparation prior to the optical scanning, the post processing of data collected in the optical scanning phase and finally decision making based on these results. Sample preparation may include steps such as: extraction of the sample from the tested subject (human, animal, plant environment etc.); separation of different parts of the sample to achieve higher concentration and purity of the molecules under investigation; sample amplification (e.g. through PCR); attachment of fluorescence tags or markers to different parts of the sample; and spotting of the sample into the sensing chip. The post processing of the collected data may include: normalization; background and noise reduction; and statistical analysis such as averaging over repeated tests or correlation between different tests. The decision making may include: testing against a predefined set of rules and comparison to information stored in external data-bases.

The applications and uses of the scanning sensing systems described herein can produce one or more result useful to diagnose a disease state of an individual, for example, a patient. In one embodiment, a method of diagnosing a disease comprises reviewing or analyzing data relating to the presence of a nucleic acid sequence in a sample. A conclusion based review or analysis of the data can be provided to a patient, a health care provider or a health care manager. In one embodiment the conclusion is based on the review or analysis of data regarding a disease diagnosis. It is envisioned that in another embodiment that providing a conclusion to a patient, a health care provider or a health care manager includes transmission of the data over a network.

Accordingly, business systems and methods using the scanning sensing systems and methods described herein are provided.

One aspect of the invention is a business method comprising screening patient test samples for the presence or absence of a nucleic acid sequence to produce data regarding the nucleic acid sequence, collecting the nucleic acid sequence data, providing the nucleic acid sequence data to a patient, a health care provider or a health care manager for making a conclusion based on review or analysis of the data regarding a disease diagnosis. In one embodiment the conclusion is provided to a patient, a health care provider or a health care manager includes transmission of the data over a network.

Figure 12:
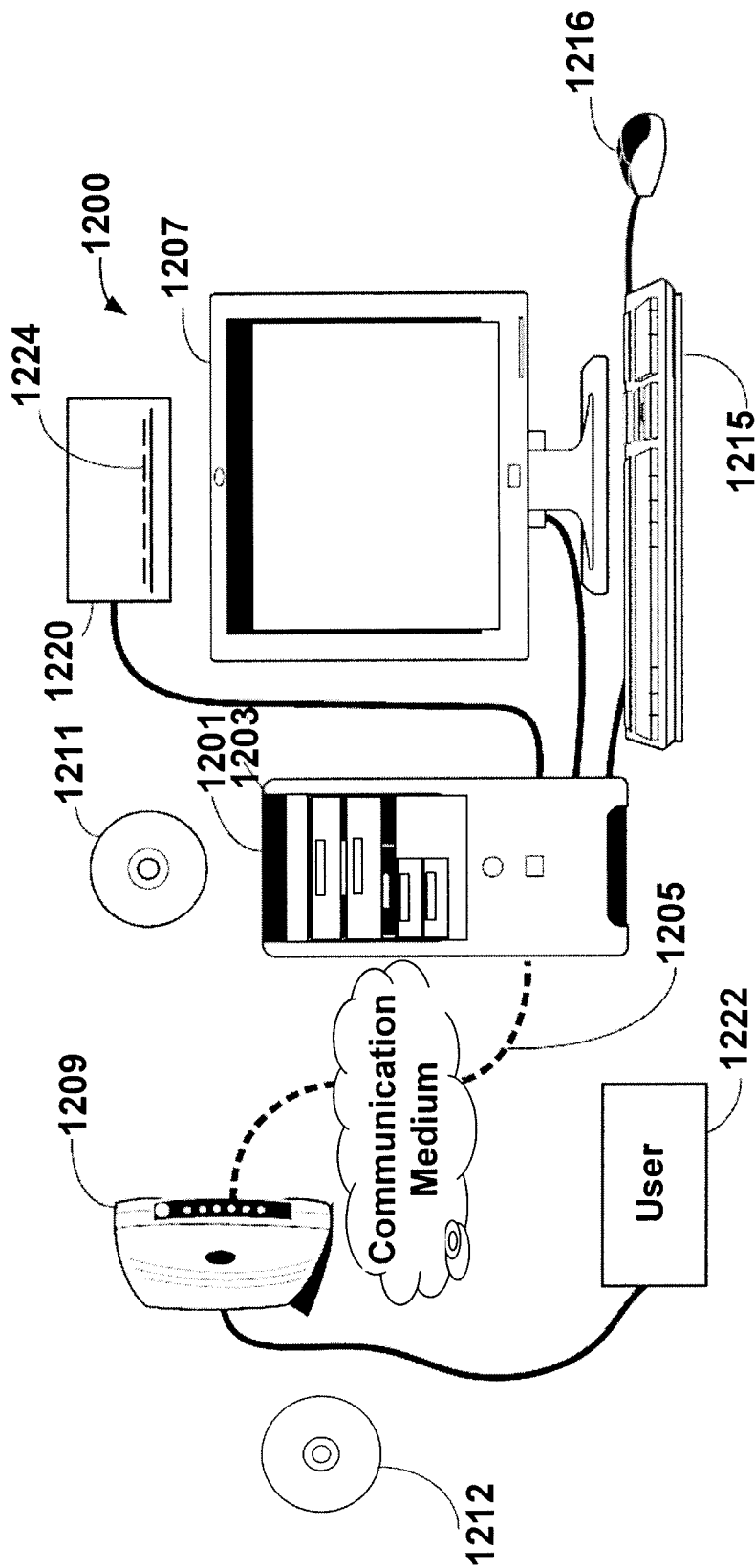
FIG. 12 is a block diagram showing a representative example logic device in communication with an apparatus for use with the scanning sensing system of the invention.

Accordingly FIG. 12 is a block diagram showing a representative example logic device through which reviewing or analyzing data relating to the present invention can be achieved. Such data can be in relation to a disease, disorder or condition in an individual. FIG. 12 shows a computer system (or digital device) 1200 connected to an apparatus 1220 for use with the scanning sensing system 1224 to, for example, produce a result. The computer system 1200 may be understood as a logical apparatus that can read instructions from media 1211 and/or network port 1205, which can optionally be connected to server 1209 having fixed media 1212. The system shown in FIG. 12 includes CPU 1201, disk drives 1203, optional input devices such as keyboard 1215 and/or mouse 1216 and optional monitor 1207. Data communication can be achieved through the indicated communication medium to a server 1209 at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present invention can be transmitted over such networks or connections for reception and/or review by a party 1222. The receiving party 1222 can be but is not limited to a patient, a health care provider or a health care manager.

In one embodiment, a computer-readable medium includes a medium suitable for transmission of a result of an analysis of an environmental or biological sample. The medium can include a result regarding a disease condition or state of a subject, wherein such a result is derived using the methods described herein.

Kits

Kits comprising reagents useful for performing the methods described herein are also provided.

In some embodiments, a kit comprises scanning sensing system as described herein and reagents for detecting a target in the sample. The kit may optionally contain one or more of the following: primer, fluorescently labeled and/or 3'-OH blocked d-NTPs, and DNA polymerase. Optionally the kit may include reagents for nucleic acid extraction and/or processing.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for sequencing of one or more different target nucleic acids.

Figure 13:
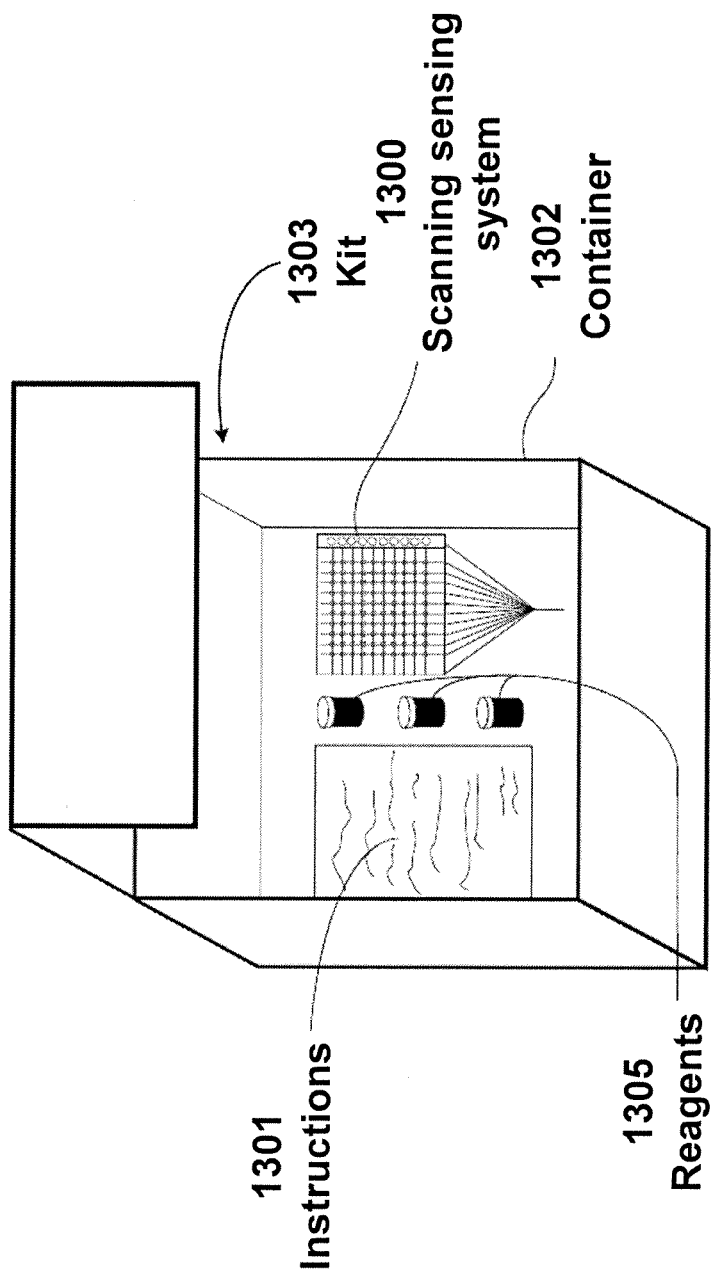
FIG. 13 is a block diagram showing a representative example of a kit.

As described herein and shown in an illustrative example in FIG. 13, in certain embodiments a kit 1303 can include a housing or container 1302 for housing various components. As shown in FIG. 13, and described herein, the kit 1303 can optionally include instructions 1301 and reagents 1305, for example, DNA sequencing reagents. Other embodiments of the kit 1303 are envisioned wherein the components include various additional features described herein.

In one embodiment, a kit for sequencing by phased synthesis includes a scanning sensor system including a switchable light source, a detector, and a substrate. The substrate can include a plurality of excitation waveguides and a plurality of collection waveguides as described herein. The excitation waveguides and collection waveguides of the substrate cross or intersect to form intersection regions and a two-dimensional array. The system further includes a plurality of optical sensing sites. The optical sensing sites are in optical communication with one or more excitation waveguides and one or more collection waveguides. A photo-cleaving source is also provided as described herein. The kit further includes packaging and instructions for use of the system.

In another embodiment, the kit includes a substrate wherein the crossing of the excitation waveguides and collection waveguides is substantially perpendicular.

In one embodiment, the kit includes a scanning sensor system that is a planar lightwave circuit (PLC).

Prophetic Example

Sequencing by phased synthesis of DNA templates from target DNA amplification reactions will be achieved using the scanning sensing system described herein and illustrated in FIG. 2A.

Optical sensing sites of the substrate of the system are first coated with GOPTS. Oligonucleotide primers designed to be complementary to the DNA templates are delivered by a microfluidic system externally attached on top of the substrate of the scanning sensing system and are covalently coupled to the GOPTS epoxy group via a primary amino group located at the 5' end of the primer. On average about $4 \times 10^8$ primer molecules are immobilized at each optical sensing site.

Double DNA templates are next delivered in a fluid at a range of concentrations (1 pM to 1,000 pM) to selected optical sensing sites. Using a thermal transfer element of the system, the target DNA is denatured in a heating step (95° C. for 2 minutes) to produce single stranded target DNA. The formation of DNA duplexes through annealing between the single stranded target DNA and the primers is promoted by lowering the temperature at the optical sensing sites (48° C. for 10 minutes) thus forming DNA duplexes. The unbound DNA strands are then washed.

DNA Polymerase is added to the chip and allowed to bind to the primer/target duplex for 10 minutes at a temperature of 48° C.

A master mix for sequencing by a phased sequencing approach is prepared and delivered to the optical sensing sites again using the sample delivery system. The mix includes the four fluorescent nucleotide analogs (based on dATP, dTTP, dCTP and cGTP) in a buffered solution. Each fluorescent nucleotide analog is labeled with a different fluorescent tag emitting at a different wavelength. All fluorescent tags are attached to the corresponding nucleotide through a photo-cleavable chemical bond consisting of a photo-cleavable amino allyl linkage. Additionally, the 3' OH group of each of the fluorescent nucleotide analogs is blocked with a nitrobenzyl group, i.e., a photo-cleavable cage.

While the temperature is maintained at 48° C., a first extension of the DNA duplex by the polymerase occurs when a complementary nucleotide analog is incorporated at the 3'-OH of the primer. Since the fluorescent nucleotide analogs include 3'-OH blocking groups, further polymerization is inhibited after the incorporation.

A scanning light source of the scanning sensing system provides excitation light, containing one or more different wavelengths required to excite all different fluorescent tags, through the excitation waveguides of the substrate to each of the optical sensing sites in a scanning fashion. The excitation light when directed to the particular optical sensing site will produce a fluorescent light output that is collected and transmitted by the collection waveguides of the substrate to the dispersive module.

The dispersive module diverts the fluorescent light output from each collection waveguide to one of four wavelength dedicated elements of a detector array depending on the wavelength. The detector array used is a modified version of a Hamamatsu S8550 4×8 Silicon APD array that includes a 4×10 array of elements for detecting fluorescent signal. Detected fluorescent signal from the optical sensing sites is recorded and analyzed by a control system to identify the base added in the first extension in each and every one of the sensing sites.

Next, a pulse of light from a photo-cleaving light source is delivered to all sensing sites to initiate the second extension event. The photo-cleaving light source is a StockerYale Lasiris PureBeam laser coupled to the photo-cleaving light source input of the system. The photo-cleaving light source generates a 10 m Watts of light at a wavelength of 380 nm and can be modulated to generate short (micro-second) pulses. The photo-cleaving light pulse delivered to the optical sensing sites serves to photo-cleave both the fluorescent tag and blocking group of the fluorescent nucleotide analog that was incorporated during the first extension event.

After photo-cleaving the released fluorescent tags and blocking groups are washed away by the sample delivery system which keeps circulating the master mix providing constant flow of fresh reagents to the sequencing cycle.

A second extension event is initiated and the process described above is repeated for a 100 cycles of incorporation, detection, photo-cleavage and washing to achieve a 100 base sequencing read of the DNA templates.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A scanning sensor system for sequencing a nucleic acid comprising:
  a substrate comprising a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide evanescent optical communication with an optical sensing site adjacent each crossing;
  wherein each optical sensing site is adjacent to and in optical communication with one of the excitation waveguides and one of the collection waveguides at the intersection regions, so that the excitation waveguides couple into the optical sensing site through an evanescent electromagnetic field and the collection waveguides couple into the optical sensing sites through an evanescent electromagnetic field;
  one or more switchable light sources, comprising a scanning light source input and a photo-cleaving light source input, coupled to and in optical communication with the excitation waveguides of the substrate;
a light dispersive module coupled to and in optical communication with the collection waveguides of the substrate, and comprising an array of elements; and
a detector coupled to and in optical communication with the light dispersive module.

2. The system of claim 1, wherein a scanning light source is coupled to a first switchable light source coupled to and in optical communication with the excitation waveguides at a first side of the substrate and a photo-cleaving light source is coupled to a second switchable light source coupled to and in optical communication with the excitation waveguides at a second side of the substrate.

3. The system of claim 1 or claim 2, wherein the dispersive module is configured to disperse light from one or more of the collection waveguides to a plurality of elements in the detector.

4. The system of claim 3, wherein the dispersive module is configured to disperse light from a given collection waveguide to four or more elements in the detector.

5. The system of claim 4, wherein the light dispersed from the dispersive module comprises a plurality of light wavelengths.

6. The system of claim 5, wherein the plurality of wavelengths comprises four or more light wavelengths.

7. The system of claim 1 or claim 2, wherein the photo-cleaving light source emits light having a wavelength ranging between 400 nm and 2000 nm.

8. The system of claim 7, wherein the photo-cleaving light source input is coupled to an ultra-violet light source.

9. The system of claim 8, wherein the ultra-violet light source emits light having a wavelength ranging between 100 nm and 400 nm.

10. A scanning sensor system for sequencing a nucleic acid comprising:
a substrate comprising a plurality of excitation waveguides and a plurality of collection waveguides, the excitation waveguides and collection waveguides arranged in a lateral plane so that the excitation waveguides and collection waveguides cross to form a two-dimensional array of intersection regions where the crossing of each excitation waveguide and collection waveguide provides evanescent optical communication with an optical sensing site adjacent to one of the excitation waveguides and one of the collection waveguides at each crossing, further wherein the excitation waveguides are single-mode in a vertical dimension and multimode in a lateral dimension;
wherein the plurality of optical sensing sites are each in optical communication with the excitation waveguide and collection waveguide so that the excitation waveguides couple into the optical sensing sites through an evanescent electromagnetic field and the collection wave guides couple into the optical sensing sites through an evanescent electromagnetic field;
one or more switchable light sources, comprising a scanning light source input and a photo-cleaving light source input, coupled to and in optical communication with the excitation waveguides of the substrate;
a light dispersive module coupled to and in optical communication with the collection waveguides of the substrate, and comprising an array of elements; and
a detector coupled to and in optical communication with the light dispersive module.

11. A scanning sensor system for sequencing a nucleic acid comprising:
a substrate comprising a plurality of excitation waveguides, and a plurality of collection waveguides, the excitation waveguides and collection waveguides crossing to form a two-dimensional array of intersection regions where an excitation waveguide and a collection waveguide cross and provide evanescent optical communication with an optical sensing site;
a plurality of optical sensing sites wherein each optical sensing site is adjacent to and in optical communication with one of the excitation waveguides and one of the collection waveguides, so that the excitation waveguides couple into the optical sensing sites through an evanescent electromagnetic field and the collection waveguides couple into the optical sensing sites through an evanescent electromagnetic field;
one or more switchable light sources, comprising a scanning light source input and a photo-cleaving light source input, coupled to and in optical communication with the excitation waveguides of the substrate;
a light dispersive module coupled to and in optical communication with the collection waveguides of the substrate, and comprising an array of elements; and
a detector coupled to and in optical communication with the light dispersive module.

12. The system of claim 1, wherein the optical sensing site is a well.

13. The system of claim 1, wherein the optical sensing site is above the collection waveguide and the excitation waveguide.

14. The system of claim 1, wherein the optical sensing site is in a different layer than the collection waveguide and the excitation waveguide.

* * * * *